US011426460B2

(12) United States Patent
Deng et al.

(10) Patent No.: US 11,426,460 B2
(45) Date of Patent: *Aug. 30, 2022

(54) USE OF INACTIVATED NONREPLICATING MODIFIED VACCINIA VIRUS ANKARA (MVA) AS MONOIMMUNOTHERAPY OR IN COMBINATION WITH IMMUNE CHECKPOINT BLOCKING AGENTS FOR SOLID TUMORS

(71) Applicant: Memorial Sloan Kettering Cancer Center, New York, NY (US)

(72) Inventors: Liang Deng, New York, NY (US); Stewart Shuman, New York, NY (US); Jedd D. Wolchok, New York, NY (US); Taha Merghoub, New York, NY (US); Peihong Dai, New York, NY (US); Weiyi Wang, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 81 days.

This patent is subject to a terminal disclaimer.

(21) Appl. No.: 16/779,174

(22) Filed: Jan. 31, 2020

(65) Prior Publication Data
US 2020/0237902 A1    Jul. 30, 2020

Related U.S. Application Data

(63) Continuation of application No. 15/553,222, filed as application No. PCT/US2016/019663 on Feb. 25, 2016, now Pat. No. 10,639,366.
(Continued)

(51) Int. Cl.
*A61K 39/285* (2006.01)
*A61K 39/12* (2006.01)
(Continued)

(52) U.S. Cl.
CPC .......... *A61K 39/285* (2013.01); *A61K 39/12* (2013.01); *A61K 39/39541* (2013.01);
(Continued)

(58) Field of Classification Search
None
See application file for complete search history.

(56) References Cited

U.S. PATENT DOCUMENTS 5,494,807 A    2/1996   Paoletti et al.
5,762,938 A    6/1998   Paoletti et al.
(Continued)

FOREIGN PATENT DOCUMENTS

CA    2435967 A1    1/2005
CA    2436196 A1    1/2005
(Continued)

OTHER PUBLICATIONS

Melief CJ. Cancer immunotherapy by dendritic cells. Immunity. Sep. 19, 2008;29(3):372-83. doi: 10.1016/j.immuni.2008.08.004. PMID: 18799145 (Year: 2008).*
(Continued)

*Primary Examiner* — Michelle S Horning
(74) *Attorney, Agent, or Firm* — Foley & Lardner LLP

(57) ABSTRACT

The present disclosure relates to infection-competent, but nonreplicative inactivated modified vaccinia Ankara (MVA) and its use as immunotherapy, alone, or in combination with immune checkpoint blocking agents for the treatment of malignant solid tumors. Particular embodiments relate to inducing an immune response in a subject diagnosed with a solid malignant tumor.

20 Claims, 22 Drawing Sheets

Specification includes a Sequence Listing.

Related U.S. Application Data

(60) Provisional application No. 62/120,862, filed on Feb. 25, 2015.

(51) Int. Cl.
  *A61K 39/395* (2006.01)
  *C07K 16/28* (2006.01)
  *A61K 45/06* (2006.01)
  *A61K 39/00* (2006.01)

(52) U.S. Cl.
  CPC ........ *A61K 39/39558* (2013.01); *A61K 45/06* (2013.01); *C07K 16/2818* (2013.01); *C07K 16/2827* (2013.01); *A61K 2039/505* (2013.01); *A61K 2039/5252* (2013.01); *A61K 2039/54* (2013.01); *A61K 2039/585* (2013.01); *C07K 2317/76* (2013.01); *C12N 2710/24132* (2013.01); *C12N 2710/24134* (2013.01)

(56) References Cited

U.S. PATENT DOCUMENTS

| | | |
|---|---|---|
| 5,766,882 A | 6/1998 | Falkner et al. |
| 6,004,777 A | 12/1999 | Tartaglia et al. |
| 6,265,189 B1 | 7/2001 | Paoletti |
| 6,372,455 B1 | 4/2002 | Jacobs et al. |
| 6,475,999 B1 | 11/2002 | Mastrangelo et al. |
| 6,548,068 B1 | 4/2003 | Schlom et al. |
| 6,750,043 B2 | 6/2004 | Jacobs et al. |
| 6,761,893 B2 | 7/2004 | Chaplin et al. |
| 6,846,652 B2 | 1/2005 | Jacobs et al. |
| 6,942,855 B2 | 9/2005 | Jacobs et al. |
| 7,001,718 B2 | 2/2006 | Jacobs et al. |
| 7,049,145 B2 | 5/2006 | Erfle et al. |
| 7,208,313 B2 | 4/2007 | McCart et al. |
| 7,252,817 B2 | 8/2007 | Coffey et al. |
| 7,256,037 B2 | 8/2007 | Ellenhorn et al. |
| 7,306,902 B2 | 12/2007 | Thompson et al. |
| 7,431,929 B2 | 10/2008 | Jacobs et al. |
| 7,550,147 B2 | 6/2009 | Howley et al. |
| 7,588,767 B2 | 9/2009 | Szalay et al. |
| 7,807,146 B2 | 10/2010 | Delcayre et al. |
| 8,052,968 B2 | 11/2011 | Chen et al. |
| 8,105,578 B2 | 1/2012 | Roberts et al. |
| 8,377,688 B2 | 2/2013 | Delcayre et al. |
| 8,506,947 B2 | 8/2013 | McCart et al. |
| 8,679,509 B2 | 3/2014 | Evans et al. |
| 8,747,837 B2 | 6/2014 | Kirn et al. |
| 8,778,328 B2 | 7/2014 | Erbs et al. |
| 8,852,927 B2 | 10/2014 | Szalay et al. |
| 8,859,256 B2 | 10/2014 | Szalay et al. |
| 8,865,153 B2 | 10/2014 | Szalay et al. |
| 8,871,219 B2 | 10/2014 | Heeney et al. |
| 9,101,658 B2 | 8/2015 | Contag et al. |
| 9,175,057 B2 | 11/2015 | Schlom et al. |
| 9,180,150 B2 | 11/2015 | Erbs et al. |
| 9,234,197 B2 | 1/2016 | Chaput et al. |
| 9,273,327 B2 | 3/2016 | Cottingham |
| 9,670,506 B2 | 6/2017 | Pantaleo et al. |
| 9,879,281 B2 | 1/2018 | Son et al. |
| 9,919,062 B2 | 3/2018 | Kirn |
| 10,548,930 B2 | 2/2020 | Deng et al. |
| 10,639,366 B2 * | 5/2020 | Deng ................. C07K 16/2818 |
| 10,736,962 B2 | 8/2020 | Deng et al. |
| 2002/0061298 A1 | 5/2002 | Coffey et al. |
| 2002/0155529 A1 | 10/2002 | Jacobs et al. |
| 2003/0113919 A1 | 6/2003 | Emtage et al. |
| 2004/0091995 A1 | 5/2004 | Schlom et al. |
| 2004/0208850 A1 | 10/2004 | Ellenhorn et al. |
| 2005/0287162 A1 | 12/2005 | Baier et al. |
| 2006/0088909 A1 | 4/2006 | Compans et al. |
| 2006/0099181 A1 | 5/2006 | Jacobs et al. |
| 2006/0216312 A1 | 9/2006 | Jacobs |
| 2007/0036758 A1 | 2/2007 | Jacobs et al. |
| 2007/0178065 A1 | 8/2007 | Lattime et al. |
| 2007/0275010 A1 | 11/2007 | Feinberg et al. |
| 2008/0075694 A1 | 3/2008 | Drexler et al. |
| 2008/0181870 A1 | 7/2008 | Lowenstein et al. |
| 2009/0162288 A1 | 6/2009 | Chen et al. |
| 2010/0247622 A1 | 9/2010 | Coffey et al. |
| 2010/0316609 A1 | 12/2010 | Dewhurst et al. |
| 2011/0064650 A1 | 3/2011 | Szalay |
| 2011/0142874 A1 | 6/2011 | Jacobs et al. |
| 2011/0206640 A1 | 8/2011 | Bell et al. |
| 2012/0308484 A1 | 12/2012 | Szalay et al. |
| 2012/0328649 A1 | 12/2012 | Falkner et al. |
| 2013/0195912 A1 | 8/2013 | Cottingham |
| 2013/0243813 A1 | 9/2013 | Howley et al. |
| 2013/0295675 A1 | 11/2013 | Jacobs et al. |
| 2014/0086976 A1 | 3/2014 | Szalay et al. |
| 2014/0087362 A1 | 3/2014 | Szalay et al. |
| 2014/0193859 A1 | 7/2014 | Jacobs et al. |
| 2014/0271549 A1 | 9/2014 | Szalay |
| 2014/0377870 A1 | 12/2014 | Jacobs et al. |
| 2015/0037355 A1 | 2/2015 | Kirn et al. |
| 2015/0202272 A1 | 7/2015 | Lauterbach et al. |
| 2015/0240246 A1 | 8/2015 | Jacobs et al. |
| 2015/0250837 A1 | 9/2015 | Nolin et al. |
| 2015/0250869 A1 | 9/2015 | Sene et al. |
| 2015/0283220 A1 | 10/2015 | Mandl et al. |
| 2016/0130564 A1 | 5/2016 | Marais et al. |
| 2016/0185875 A1 | 6/2016 | Cheng et al. |
| 2016/0235793 A1 | 8/2016 | Thorne |
| 2016/0271239 A1 | 9/2016 | Foy et al. |
| 2016/0339090 A1 | 11/2016 | Hacohen et al. |
| 2017/0020938 A1 | 1/2017 | Wang et al. |
| 2017/0021009 A1 | 1/2017 | Jacobs et al. |
| 2017/0106065 A1 | 4/2017 | Foy et al. |
| 2017/0143780 A1 | 5/2017 | Zitvogel et al. |
| 2017/0157188 A1 | 6/2017 | Silvestre et al. |
| 2017/0246280 A1 | 8/2017 | Pantaleo et al. |
| 2017/0266270 A1 | 9/2017 | Foy et al. |
| 2017/0340687 A1 | 11/2017 | Nakao et al. |

FOREIGN PATENT DOCUMENTS

| | | |
|---|---|---|
| CN | 1842602 A | 10/2006 |
| CN | 105039269 A | 11/2015 |
| CN | 106456747 A | 2/2017 |
| CN | 107735103 A | 2/2018 |
| CN | 109152827 A | 1/2019 |
| DE | 10144664.9 A1 | 6/2005 |
| EP | 2 771 465 A1 | 5/2013 |
| EP | 2 136 633 B1 | 10/2015 |
| EP | 3 142 690 A2 | 4/2017 |
| EP | 3 850 103 A1 | 7/2021 |
| JP | 2005-502360 A | 1/2005 |
| JP | 2006-512097 A | 4/2006 |
| WO | WO-03/023040 A2 | 3/2003 |
| WO | WO-2004/024756 A2 | 3/2004 |
| WO | WO-2004/058801 A2 | 7/2004 |
| WO | WO-2004/003987 A1 | 8/2004 |
| WO | WO-2006/120474 A2 | 11/2006 |
| WO | WO-2007/119895 A1 | 10/2007 |
| WO | WO-2008/045346 A2 | 4/2008 |
| WO | WO-2008/113078 A1 | 9/2008 |
| WO | WO-2009/152179 A1 | 12/2009 |
| WO | WO-2011/156470 A1 | 12/2011 |
| WO | WO-2012/009644 A2 | 1/2012 |
| WO | WO-2013/038066 A1 | 3/2013 |
| WO | WO-2014/081976 A1 | 5/2014 |
| WO | WO-2014/036412 A2 | 6/2014 |
| WO | WO-2015/066715 A1 | 5/2015 |
| WO | WO-2015/069571 A1 | 5/2015 |
| WO | WO-2015/084897 A2 | 6/2015 |
| WO | WO-2015/138741 A1 | 9/2015 |
| WO | WO-2016/046357 A1 | 3/2016 |
| WO | WO-2016/128542 A1 | 8/2016 |
| WO | WO-2016/144564 A1 | 9/2016 |
| WO | WO-2016/144564 A2 | 9/2016 |
| WO | WO-2016/168862 A1 | 10/2016 |
| WO | WO-2016/205429 A1 | 12/2016 |
| WO | WO-2017/024000 A1 | 2/2017 |
| WO | WO-2017/037523 A1 | 3/2017 |

(56) References Cited

FOREIGN PATENT DOCUMENTS

| WO | WO-2017/043815 A1 | 3/2017 |
|---|---|---|
| WO | WO-2017/044780 A1 | 3/2017 |
| WO | WO-2017/075570 A1 | 5/2017 |
| WO | WO-2017/103291 A1 | 6/2017 |
| WO | WO-2017/129765 A1 | 8/2017 |
| WO | WO-2017/147553 A2 | 8/2017 |
| WO | WO-2017/147554 A1 | 8/2017 |
| WO | WO-2017/147554 A2 | 8/2017 |
| WO | WO-2017/156349 A1 | 9/2017 |
| WO | WO-2017/205674 A1 | 11/2017 |
| WO | WO-2018/016917 A1 | 1/2018 |
| WO | WO-2018/017747 A2 | 1/2018 |
| WO | WO-2018/031694 A1 | 1/2018 |
| WO | WO-2018/049248 A1 | 3/2018 |
| WO | WO-2018/057755 A1 | 3/2018 |
| WO | WO-2018/058258 A1 | 4/2018 |

OTHER PUBLICATIONS

Espenschied J et al, "CTL-4 blockade enhances the therapeutic effect of an attenuated poxvirus vaccine targeting p53 in in established murine tumor model", Journal of Immunology, vol. 170, Issue 6, pp. 3401-3407.

Kreiter et al., "Mutant MHC class II epitopes drive therapeutic immune responses to cancer." Nature. Apr. 22, 2015, vol. 520, No. 7549, pp. 692-696.

McCart et al., "Systemic Cancer Therapy with a Tumor-selective Vaccinia Virus Mutant Lacking Thymidine Kinase and Vaccinia Growth Factor Genes.", Cancer Res., (2001), 61, [24], p. 8751-8757.

Alharbi, et al., "ChAdOx1 and MVA based vaccine candidates against MERS-CoV elicit neutralising antibodies and cellular immune responses in mice," Vaccine, vol. 35, pp. 3780-3788 (Jun. 27, 2017).

Angell et al., "From the immune contexture to the Immunoscore: the role of prognostic and predictive immune markers in cancer," Curr. Opin. Immunol., 25, pp. 261-267 (2013).

Antoine et al., "The complete genomic sequence of the modified vaccinia Ankara strain: comparison with other orthopoxviruses", Virology, 244, pp. 365-396 (1998).

Arsenio et al., "Antagonizing activity of vaccinia virus E3L against human interferons in Huh7 cells," Journal of Virology, vol. 377, No. 1, p. 124-132 (Jul. 20, 2008).

Backes et al., "Viral host-range factor C7 or K1 is essential for modified vaccinia virus Ankara late gene expression in human and murine cells, irrespective of their capacity to inhibit protein kinase R-mediated phosphorylation of eukaryotic translation initiation factor 2a," J. of General Virology, vol. 91, pp. 470-482 (Feb. 1, 2010).

Barber, "Innate immune DNA sensing pathways: STING, AIMII and the regulation of interferon production and inflammatory responses", Curr. Opin. Immunol., 23, pp. 10-20 (2011).

Bisht et al., "Severe acute respiratory syndrome coronavirus spike protein expressed by attenuated vaccinia virus protectively immunizes mice," PNAS, vol. 101, pp. 6641-6646 (Apr. 27, 2004).

Bommareddy et al., "MEK inhibition enhances oncolytic virus immunotherapy through increased tumor cell killing and T cell activation," Science Translational Medicine, vol. 10, Issue 471 (Dec. 12, 2018).

Brandler et al., "Preclinical studies of a modified vaccinia virus Ankara-based HIV candidate vaccine: antigen presentation and antiviral effect", J. Virol., vol. 84, No. 10, pp. 5314-5328 (2010).

Brandt et al., "The N-terminal domain of the vaccinia virus E3L-protein is required for neurovirulence" Virology, vol. 333, No. 2, pp. 263-270 (Mar. 15, 2005).

Brandt, T. et al.; The N-terminal domain of the vaccinia virus E3L-protein is required for neurovirulence, but not induction of a protective immune response. Virology. 2005, 333, No. 2, 263-270.

Breitbach et al., "Targeted and armed oncolytic poxviruses for cancer: the lead example of JX-594," Current Pharmaceutical Biotechnology, 13, pp. 1768-1772 (2012).

Brinkman et al., "Fingolimod (FTY720): discovery and development of an oral drug to treat multiple sclerosis," Nature Reviews | Drug Discovery, vol. 9, pp. 883-897 (Nov. 2010).

Caisova et al., "Innate immunity based cancer immunotherapy: B16-F10 murine melanoma model," BMC Cancer, 16:940, 11 pages (2016).

Cao et al., "Innate immune response of human plasmacytoid dendritic cells to poxvirus infection is subverted by vaccinia E3 via its Z-DNA/RNA binding domain," PLOS ONE, vol. 7, No. 5, p. e36823 (May 14, 2012).

Cao, H. et al.; Innate immune response of human plasmacytoid dendritic cells to poxvirus infection is subverted by vaccinia E3 via its Z-DNA/RNA binding domain. Plos One. 2012, vol. 7, No. 5, e36823, pp. 2 and Fig. 8.

Castle et al., "Exploiting the mutanome for tumor vaccination", Cancer Res., 72, pp. 1081-1091 (2012).

Chafekar, et al., "MERS-CoV: Understanding the Latest Human Coronavirus Threat," Viruses, 10, 93, 22 pages (Feb. 24, 2018).

Chavan et al., "Expression of CCL20 and granulocyte-macrophage colony-stimulating factor, but not Flt3-L, from modified vaccinia virus Ankara enhances antiviral cellular and humoral immune responses," J. Virology, vol. 80, No. 15, pp. 7676-7687 (2006).

Chi et al., "DNA vaccine encoding Middle East respiratory syndrome coronavirus S1 protein induces protective immune responses in mice," Vaccine, vol. 35, pp. 2069-2075 (Apr. 11, 2017).

Coffey et al., "Reovirus therapy of tumors with activated Ras pathway," Science, 282, pp. 1332-1334 (1998).

Curran et al, Tumor Vaccines Expressing Flt2 Ligand Synergize with CTLA-4 Blockade to Reject Preimplanted Tumors, Cancer Research vol. 69 No. 19, Sep. 8, 2009, pp. 7747-7755.

Dai et al., "Abstract B031: Heat-inactivated modified vaccinia virus Ankara induces type I IFN and antitumor immunity via the cytosolic DNA-sensing pathway," retrieved from: http://www.cancerimmunolrres.aacrjournals.org/content/4/1_Supplement/B031 (Jun. 15, 2018).

Dai et al., "Intratumoral delivery of inactivated modified vaccinia virus Ankara (iMVA) induces systemic antitumor immunity via STING and Batf3-dependent dendritic cells" Science Immunology, vol. 2, No. 11, pp. 1-34 (May 19, 2017).

Dai, P et al, Modified Vaccinia Virus Ankara Triggers Type 1 IFN Production in Murine Conventional Dendritic Cells via a cGAS/STING-Mediated Cytosolic DNA-Sensing Pathway, PLOS Pathogens, Apr. 2014, vol. 10, pp. 1-13.

Dai, P et al, Myxoma Virus Induces Type 1 Interferon Production in Murine Plasmacytoid Dendritic Cells via a TLR9/MyD88-, IRF5/IRF7-, and IFNAR-Dependent Pathway. Journal of Virology, Oct. 2011, pp. 10814-10825.

Deng et al., "STING-Dependent Cytosolic DNA Sensing Promotes Radiation-Induced Type I Interferon-Dependent Antitumor Immunity in Immunogenic Tumors", Immunity, vol. 41, No. 5, pp. 843-852 (2014).

Deng et al., "Vaccinia virus infection attenuates innate immune responses and antigen presentation by epidermal dendritic cells", J Virol., 80, pp. 9977-9987 (2006).

Diamond et al., "Type I interferon is selectively required by dendritic cells for immune rejection of tumors", J Exp Med., vol. 208, No. 10, pp. 1989-2003 (2011).

Drexler et al., "Modified Vaccinia Virus Ankara for Delivery of Human Tyrosinase as Melanomaassociated Antigen: Induction of Tyrosinase- and Melanoma-specific Human Leukocyte Antigen A*0201-restricted Cytotoxic T Cells in Vitro and in Vivo1," Cancer Research, vol. 59, p. 4955-4963 (Oct. 1, 1999).

Drillien et al, Modified vaccination virus Ankara induces moderate activation of human dendritic cells, Journal of General Virology, Society for General Microbiology, vol. 85, No. Pt 8, Aug. 1, 2004, pp. 2167-2175.

Du et al., "The spike protein of SARS-CoV—a target for vaccine and therapeutic development," Microbiology, vol. 7, pp. 226-236 (Mar. 2009).

(56) References Cited

OTHER PUBLICATIONS

Engelmayer et al., "Vaccinia virus inhibits the maturation of human dendritic cells: a novel mechanism of immune evasion", J Immunol., 163, pp. 6762-6768 (1999).
Fishcer et al., "Modified vaccinia virus Ankara protein F1L is a novel BH3-domain-binding protein and acts together with the early viral protein E3L to block virus-associated apoptosis" Cell Death Differ., 13, pp. 109-118 (2006).
Fuertes et al., "Host type I IFN signals are required for antitumor CD8 T-cell responses through CD8{alpha} dendritic cells", J. Exp. Med., vol. 208, No. 10, 2005-2016 (2011).
Fuertes et al., "Type I interferon response and innate immune sensing of cancer," Trends Immunol., vol. 34, No. 2, pp. 67-73 (Feb. 2013).
Fung et al., "Human Coronavirus: Host-Pathogen Interaction," Annual Review of Microbiology, 73, pp. 529-557 (Jun. 21, 2019).
Gao et al., "Structure-function analysis of STING activation by c[G(2',5')pA(3',5')p] and targeting by antiviral DMXAA", Cell, 154, pp. 748-762 (2013).
Garcia et al., "Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02)", Vaccine, 29, pp. 8309-8316 (2011).
Garrido et al., "The escape of cancer from T lymphocytes: immunoselection of MHC class I loss variants harboring structural-irreversible "hard" lesions," Cancer Immunol. Immunother., 59, pp. 1601-1606 (2010).
GenBank: U94848.1 "Vaccinia virus strain Ankara, complete genomic sequence" p. 1-3 (Apr. 13, 2003).
Gerlini et al., "Metastatic melanoma secreted IL-10 down-regulates CD1 molecules on dendritic cells in metastatic tumor lesions", Am J Pathol., 165, pp. 1853-1863 (2004).
Gitlin et al., "Essential role of mda-5 in type I IFN responses to polyriboinosinic:polyribocytidylic acid and encephalomyocarditis picornavirus", Proc. Natl. Acad. Sci. U S A., vol. 103, No. 22, pp. 8459-8464 (May 30, 2006).
Goepfert et al., "Phase 1 safety and immunogenicity testing of DNA and recombinant modified vaccinia Ankara vaccines expressing HIV-1 virus-like particles", J Infect Dis., 203, pp. 610-619 (2011).
Gomez et al., "MVA and NYVAC as vaccines against emergent infectious diseases and cancer," Current Gene Therapy, vol. 11, No. 3, p. 189-217 (Jun. 2011).
Gomez et al., "The poxvirus vectors MVA and NYVAC as gene delivery systems for vaccination against infectious diseases and cancer", Curr Gene Ther., 8, pp. 97-120 (2008).
Greiner et al. "The highly attenuated vaccinia virus strain modified virus Ankara induces apoptosis in melanoma cells and allows bystander dendritic cells to generate a potent anti tumoral immunity" Clinical and Experimental Immunology vol. 146. No. 2, Nov. 1, 2006 pp. 344-353.
Guerra et al., "Distinct gene expression profiling after infection of immature human monocyte-derived dendritic cells by the attenuated poxvirus vectors MVA and NYVAC," J. of Virology, vol. 61, No. 16, pp. 8701-8721 (May 30, 2007).
Guerra et al., "Host-Range Restriction in Vaccinia Virus E3L Deletion Mutant Can Be Overcome In Vitro, but Not In Vivo, by Expression of the Influenza Virus NS1 Protein," PLoS ONE. vol. 6 No. 12, p. e28677 (2011).
Haagmans, et al., "An orthopoxvirus-based vaccine reduces virus excretion after MERS-COV infection in dromedary camels," Science, vol. 351, pp. 77-81 (Jan. 1, 2016).
Hamid et al., "Safety and Tumor Responses with Lambrolizumab (Anti-PD-1) in Melanoma", The New England journal of medicine, vol. 369, No. 2, pp. 134-144 (2013).
Hammerich et al., In situ vaccination for the treatment of cancer, Immunotherapy vol. 8, No. 3, Mar. 1, 2016, pp. 315-330.
Harrop et al., "Vaccination of Colorectal Cancer Patients with Modified Vaccinia Ankara Delivering the Tumor Antigen 5T4 (TroVax) Induces Immune Responses which Correlate with Disease Control: A Phase I/II Trial," Clinical Cancer Research, vol. 12, No. 11 Pt. 1, p. 3416-6424 (Jun. 1, 2006).
Hodge et al., "Modified Vaccinia Virus Ankara Recombinants Are as Potent as Vaccinia Recombinants in Diversified Prime and Boost Vaccine Regimens to Elicit Therapeutic Antitumor Responses," American Association for Cancer Research, vol. 63, No. 22, p. 7942-7949 (Nov. 15, 2003).
Hodi et al., "Improved survival with ipilimumab in patients with metastatic melanoma", The New England journal of medicine, 363, pp. 711-723 (2010).
Holshue et al., "First Case of 2019 Novel Coronavirus in the United States," New England Journal of Medicine, 9 pages (Jan. 31, 2020).
Hornemann et al., "Replication of Modified Vaccinia Virus Ankara in Primary Chicken Embryo Fibroblasts Requires Expression of the Interferon Resistance Gene E3L," Journal of Virology, vol. 77, No. 15, p. 8394-8407 (Aug. 2003).
Huber et al., "Regulation of effector and memory T-cell functions by type I interferon", Immunology, 132, pp. 466-474 (2011).
Inman, "Immunotherapy/Targeted Therapy Combinations Show Promise in BRAF-Mutated Melanoma," Targeted Oncology, retrieved from: https://www.targetedonc.com/conference/smr-esmo-melanoma/immunotherapytargeted-therapy-combinations-show-promise-in-brafmutated-melanoma (Oct. 20, 2017).
International Search Report and Written Opinion on PCT/US2016/028184, dated Sep. 9, 2016, 17 pages.
International Search Report and Written Opinion on PCT/US2017/019548, dated Aug. 8, 2017, 17 pages.
International Search Report and Written Opinion on PCT/US2017/019549, dated Aug. 14, 2017, 17 pages.
International Search Report and Written Opinion on PCT/US2018/032451, dated Aug. 23, 2018, 16 pages.
International Search Report and Written Opinion on PCT/US2018/059476, dated Feb. 14, 2019, 9 pages.
International Search Report and Written Opinion, PCT/US2019/021853, Memorial Sloan Kettering Cancer Center (dated Jul. 16, 2019).
International Search Report and Written Opinion, PCT/US2019/051343 (dated Feb. 7, 2020).
Ishikawa et al., "STING is an endoplasmic reticulum adaptor that facilitates innate immune signaling", Nature, 455, pp. 674-678 (2008).
Jacobs et al., Vaccinia virus vaccines: Past, present and future, Antiviral Research, Elsevier BV, NL vol. 84, No. 1, Oct. 1, 2009 pp. 1-13.
Jenne et al., "Poxvirus as a vector to transduce human dendritic cells for immunotherapy: abortive infection but reduced APC function", Gene therapy, 7, pp. 1575-1583 (2000).
Jochems et al., "Tumor-infiltrating immune cells and prognosis: the potential link between conventional cancer therapy and immunity", Exp Biol Med.(Maywood), 236, pp. 567-579 (2011).
Kibler et al., "Double-stranded RNA is a trigger for apoptosis in vaccinia virus-infected cells", J. Virol., vol. 71, No. 3, pp. 1992-2003 (1997).
Kirn et al., "Replication-selective virotherapy for cancer: Biological principles, risk management and future directions," Nat. Med., 7, pp. 781-787 (2001).
Kirn et al., "Targeted and armed oncolytic poxviruses: a novel multi-mechanistic therapeutic class for cancer," Nature Reviews—Cancer, 9, pp. 64-71 (2009).
Kirn et al., "Targeting of interferon-beta to produce a specific, multi-mechanistic oncolytic vaccinia virus", PLoS Med., vol. 4, No. 12, pp. 2001-2012 (2007).
Kuzu et al., "Current State of Animal (Mouse) Modeling in Melanoma Research," Cancer Growth and Metastasis, 8(S1):81-94 (2015).
Lacy et al., "Immunotherapy for Melanoma," Expert Rev. Dermatol., 7, pp. 51-68 (2012).
Langland et al., "Inhibition of PKR by vaccinia virus: role of the N- and C-terminal domains of E3L," Journal of Virology, vol. 324, No. 2, p. 419-429 (Jul. 1, 2004).
Leach et al., "Enhancement of antitumor immunity by CTLA-4 blockade," Science, 271, pp. 1734-1736 (1996).

(56) References Cited

OTHER PUBLICATIONS

Lee et al., "The interferon-induced double-stranded RNA-activated protein kinase induces apoptosis," Journal of Virology, vol. 199, No. 2, p. 491-496 (Mar. 1994).
Lee et al., "Effect of resveratrol on the metastasis of 4T1 mouse breast cancer cells in vitro and in vivo," Nutrition Res. and Practice, vol. 6, No. 4, pp. 294-300 (2012).
Li et al., "Angiotensin-converting enzyme 2 is a functional receptor for the SARS coronavirus," Nature, vol. 426, pp. 450-454 (Nov. 27, 2003).
Li et al., "Disruption of MHC class II-restricted antigen presentation by vaccinia virus," J. Immunol., 175, pp. 6481-6488 (2005).
Li et al., "Early Transmission Dynamics in Wuhan, China, of Novel Coronavirus—Infected Pneumonia," New England Journal of Medicine, 9 pages (Jan. 29, 2020).
Li et al., "Pivotal roles of cGAS-cGAMP signaling in antiviral defense and immune adjuvant effects", Science, 341, pp. 1390-1394 (2013).
Li et al., "Structure of SARS Coronavirus Spike Receptor-Binding Domain Complexed with Receptor," Science, vol. 309, pp. 1864-1868 (Sep. 16, 2005).
Liu et al., "Deletion of C7L and K1L genes leads to significantly decreased virulence of recombinant vaccinia cirus TianTian," PLoS One, vol. 8, No. 7:e68115, pp. 1-13 (Jul. 1, 2013).
Liu, "Cancer-killing virus plus PD-1 and MEK inhibitors make for a 3-pronged attack on melanoma," retrieved from: https://www.fiercebiotech.com/research/pd-1-mek-inhibitor-and-anti-cancer-virus-a-3-pronged-attack-melanoma, 2 pages (Dec. 12, 2018).
Ludwig et al., "Role of Viral Factor E3L in Modified Vaccinia Virus Ankara Infection of Human HeLa Cells: Regulation of the Virus Life Cycle and Identification of Differentially Expressed Host Genes," Journal of Virology, vol. 79, No. 4, p. 2584-2596 (Feb. 2005).
Mandl, SJ et al, Immunotherapy With MVA-BN-HER2 Induces HER-2-specific Th1 Immunity and Alters the Intratumoral Balance of Effector and Regulatory T cells. Cancer Immunol Immunother, 2012, vol. 61, pp. 19-29.
Mayr et al., English-language translation of Abstract of: "[The smallpox vaccination strain MVA: marker, genetic structure, experience gained with the parenteral vaccination and behavior in organisms with a debilitated defence mechanism (author's transl)]," Zentralbl Bakteriol, Orig. B, 167, pp. 375-390 (1978).
Mayr et al., English-language translation of Abstract of: "Passage history, properties, and applicability of the attenuated vaccinia virus strain MVA," Infection, 3, pp. 6-14 (1975).
McIntyre et al., "Mouse models of colorectal cancer as preclinical models," Bioessays, 37(8), pp. 909-920 (Aug. 2015).
Mellman et al., "Cancer immunotherapy comes of age", Nature, 480, pp. 480-489 (2011).
Meng et al., "C7L Family of Poxvirus Host Range Genes Inhibits Antiviral Activities Induced by Type I Interferons and Interferon Regulatory Factor 1", J. Virol., vol. 86, No. 8, pp. 538-4547 (2012).
Meng et al., "Vaccinia Virus K1L and C7L Inhibit Antiviral Activities Induced by Type I Interferons," Journal of Virology, vol. 83, No. 20, p. 10627-10636 (Oct. 2009).
Meyer et al., "Mapping of deletions in the genome of the highly attenuated vaccinia virus MVA and their influence on virulence", J. Gen. Virol., 72 ( Pt 5), pp. 1031-1038 (1991).
Mlecnik et al., "Tumor immunosurveillance in human cancers", Cancer Metastasis Rev, 30, pp. 5-12 (2011).
Morales et al., Genome comparison of a nonpathogenic myoxma virus field strain with its ancestor, the virulent Lausanne strain, J. Virol, vol. 83, No. 5, pp. 2397-2403 Mar. 2009.
Moss, "Poxviridae: The viruses and their replication," In Fields Virology (Lippincott Williams & Wilkins), pp. 2905-2946 (2007).
Nagaria et al., "Combined targeting of RAF and MEK synergistically inhibits tumorigenesis in triple negative breast cancer model systems," Oncotarget, vol. 8, No. 46, pp. 80804-80819 (Aug. 24, 2017).
Nagorsen et al., "Transcriptional analysis of tumor-specific T-cell responses in cancer patients," Crit. Rev. Immunol., 22, pp. 449-462 (2002).
Nakayama et al., "In vitro comparison between mouse B16 and human melanoma cell lines of the expression of ICAM-1 induced by cytokines and/or hyperthermia," J. Dermatol., 24(6), pp. 351-360 (Jun. 1997).
Nemunaitis, J., "Oncolytic viruses,". Invest. New Drugs, 17, pp. 375-386 (1999).
Oble et al., "Focus on TILs: prognostic significance of tumor infiltrating lymphocytes in human melanoma", Cancer immunity, 9, pp. 1-20 (2009).
Pardoll, "The blockade of immune checkpoints in cancer immunotherapy," Nat. Rev. Cancer, 12(4), pp. 252-264 (Mar. 22, 2012).
Park et al., "Use of a targeted oncolytic poxvirus, JX-594, in patients with refractory primary or metastatic liver cancer: a phase I trial," Lancet Oncol., 9, pp. 533-542 (May 19, 2008).
Peggs et al., "Blockade of CTLA-4 on both effector and regulatory T-cell compartments contributes to the antitumor activity of anti-CTLA-4 antibodies", J Exp Med., 206, pp. 1717-1725 (2009).
Peihong et al., "Modified Vaccinia Virus Ankara Triggers Type I IFN Production in Murine Conventional Dendritic Cells via a cGAS/STING-Mediated Cytosolic DNA-Sensing Pathway," PLOS Pathogens, vol. 10, No. 4, p. e1003989 (Apr. 17, 2014).
Peihong, "P339 Intratumoral delivery of modified vaccinia virus Ankara expressing human Flt3L as cancer immunotherapy," 31st Annual Meeting and Associated Programs of the Society for Immunotherapy of Cancer, Pt. 2, p. 1-241 (2016).
Peiris, et al., "The Severe Acute Respiratory Syndrome," New England Journal of Medicine, vol. 349, pp. 2431-2441 (Dec. 18, 2003).
Perkus et al., "Vaccinia virus host genes," Virology, 179(1), pp. 276-286 (1990).
Pramanick et al., "Excipient selection in parenteral formulation development", Pharma Times, vol. 45, No. 3, pp. 65-77 (2013).
Raj et al., "Dipeptidyl peptidase 4 is a functional receptor for the emerging human coronavirus—EMC," Nature, vol. 495, 6 pages (Mar. 13, 2013).
Reddy et al., "Influences of BRAF Inhibitors on the Immune Microenvironment and the Rationale for Combined Molecular and Immune Targeted Therapy," Curr. Oncol. Rep., 18(7)15 pages (Jul. 2016).
Robert et al., "Ipilimumab plus dacarbazine for previously untreated metastatic melanoma", The New England journal of medicine, 364, pp. 2517-2526 (2011).
Sabbatino et al., "Antitumor activity of BRAF inhibitor and IFN combination in BRAF-mutant melanoma," J. Natl. Cancer Inst., 108(7), 11 pages (Feb. 5, 2016).
Sato et al., "Distinct and essential roles of transcription factors IRF-3 and IRF-7 in response to viruses for IFN-alpha/beta gene induction", Immunity, 13, pp. 539-548 (2000).
Sauer et al., "The N-ethyl-N-nitrosourea-induced Goldenticket mouse mutant reveals an essential function of Sting in the in vivo interferon response to Listeria monocytogenes and cyclic dinucleotides", Infection and immunity, vol. 79, No. 2, pp. 688-694 (2011).
Schaedler et al., "Sequential administration of a MVA-based MUC1 cancer vaccine and the TLR9 ligand Litenimod (Li28) improves local immune defense against tumors," Vaccine, vol. 35, No. 4, p. 577-585 (Jan. 23, 2017).
Schumacher et al., "Neoantigens in cancer immunotherapy", Science, 348, pp. 69-74 (2015).
Sharma et al., "The future of immune checkpoint therapy", Science, 348, pp. 56-61 (2015).
Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBio, vol. 6, No. 4, pp. 1-9 (2015).
Song, et al., "Middle East Respiratory Syndrome Coronavirus Spike Protein Delivered by Modified Vaccinia Virus Ankara Efficiently Induces Virus-Neutralizing Antibodies," Journal of Virology, vol. 87, pp. 11950-11954 (Nov. 2013).

(56) References Cited

OTHER PUBLICATIONS

Sun et al., "Cyclic GMP-AMP synthase is a cytosolic DNA sensor that activates the type I interferon pathway", Science, 339, pp. 786-791 (2013).
Sutter et al., "Vaccinia vectors as candidate vaccines: the development of modified vaccinia virus Ankara for antigen delivery," Current Drug Targets—Infectious Disorders 3, pp. 263-271 (2003).
Tagliamonte et al., "Antigen-specific vaccines for cancer treatment", Human vaccines & immunotherapeutics, 10, pp. 3332-3346 (2014).
Takaoka et al., "New aspects of IFN-alpha/beta signalling in immunity, oncogenesis and bone metabolism", Cancer Sci., vol. 94, No. 5, pp. 405-411 (2003).
Thorne et al., "Rational strain selection and engineering creates a broad-spectrum, systemically effective oncolytic poxvirus, JX-963", J Clin Invest., vol. 117, No. 11, pp. 3350-3358 (2007).
Topalian et al., "Immune checkpoint blockade: a common denominator approach to cancer therapy", Cancer Cell, vol. 27, No. 4, pp. 450-461 (2015).
Topalian et al., "Targeting the PD-1/B7-H1(PD-L1) pathway to activate anti-tumor immunity", Curr Opin Immunol., 24, pp. 207-212 (2012).
Tormo et al., "Targeted activation of innate immunity for therapeutic induction of autophagy and apoptosis in melanoma cells", Cancer Cell, vol. 16, No. 2, pp. 103-114 (2009).
Tumeh et al., "PD-1 blockade induces responses by inhibiting adaptive immune resistance", Nature, vol. 515, No. 7258, pp. 568-571 (2014).
Verardi et al., "A vaccinia virus renaissance: new vaccine and immunotherapeutic uses after smallpox eradication", Human vaccines & immunotherapeutics, 8, pp. 961-970 (2012).
Verheust et al., "Biosafety aspects of modified vaccinia virus Ankara (MVA)-based vectors used for gene therapy or vaccination," Vaccine, 30, pp. 2623-2632 (2012).
Vijaysri et al., "Vaccinia Viruses with Mutations in the E3L Gene as Potential Replication-Competent, Attenuated Vaccines: Intra-Nasal Vaccination," Vaccine, vol. 26, No. 5, p. 664-676 (Jan. 30, 2008).
Volz, et al., "Protective Efficacy of Recombinant Modified Vaccinia Virus Ankara Delivering Middle East Respiratory Syndrome Coronavirus Spike Glycoprotein," Journal of Virology, vol. 89, pp. 8651-8656 (Aug. 2015).
Waibler et al. "Modified Vaccinia Virus Ankara Induces Tool Line Receptor Independent Type I Interferon Responses" Journal of Virology, vol. 181 No. 22, Nov. 15, 2007 pp. 12102-12110.
Waibler et al., "Modified Vaccinia Virus Ankara Induces Toll-Like Receptor-Independent Type I Interferon Responses," Journal of Virology, vol. 81, No. 22, p. 12101-12110 (Nov. 2007).
Wang et al., "034 recombinant replication competent attenuated vaccinia virus expressing human Flt3L for cancer immunotherapy," J. Invest. Derm., vol. 136, No. 5, p. S6 (May 2016).
Wang et al., Abstracts—Adaptive Immunity and Vaccination 034, Recombinant replication competent attenuated vaccinia virus expressing human Flt3L for cancer immunotherapy, Journal of Investigative Dermatology vol. 136, No. 5 May 2016 p. S6.
Wang W. et al., 034 Recombinant replication competent attenuated vaccinia virus expressing human Flt3L for cancer immunotherapy. Society for Investigative Dermatology (SID) Annual Meeting. May 14, 2016, p. S6, vol. 136, No. 034.
Weaver et al., "The identification and characterization of a monoclonal antibody to the vaccinia virus E3 protein", Virus Res., 130, pp. 269-274 (2007).
Wing et al., "CTLA-4 control over Foxp3 regulatory T-cell function", Science, 322, pp. 271-275 (2008).

Wolchok et al., "Ipilimumab monotherapy in patients with pre-treated advanced melanoma: a randomised, double-blind, multicentre, phase 2, dose-ranging study," Lancet Oncol., 11, pp. 155-164 (2010).
Wolchok et al., "Nivolumab plus ipilimumab in advanced melanoma", The New England journal of medicine, 369, pp. 122-133 (2013).
Woo et al., "STING-dependent cytosolic DNA sensing mediates innate immune recognition of immunogenic tumors", Immunity, vol. 41, No. 5, pp. 830-842 (2014).
Wu et al., "Cyclic GMP-AMP is an endogenous second messenger in innate immune signaling by cytosolic DNA", Science, 339, pp. 826-830 (2013).
Wyatt et al., "Enhanced cell surface expression, immunogenicity and genetic stability resulting from a spontaneous truncation of HIV Env expressed by a recombinant MVA", Virology, 372, pp. 260-272 (2008).
Yong, et al., "Recent Advances in the Vaccine Development Against Middle East Respiratory Syndrome-Coronavirus," Frontiers in Microbiology, vol. 10, 18 pages (Aug. 2, 2019).
Zaki, et al., "Isolation of a Novel Coronavirus from a Man with Pneumonia in Saudi Arabia," The New England Journal of Medicine, vol. 367, pp. 1814-1820 (Nov. 8, 2012).
Zamarin et al., "Localized oncolytic virotherapy overcomes systemic tumor resistance to immune checkpoint blockade immunotherapy", Science translational medicine, vol. 6, No. 226, pp. 1-12 (2014).
Zhang, et al., "A DNA vaccine induces SARS coronavirus neutralization and protective immunity in mice," Nature, vol. 428, pp. 561-564 (Apr. 2004).
Zhou, et al., "A pneumonia outbreak associated with a new coronavirus of probable bat origin," Nature, 23 pages (Feb. 3, 2020).
Zurkova et al., "The expression of the soluble isoform of hFlt3 ligand by recombinant vaccinia virus enhances immunogenicity of the vector," Oncology Reports, vol. 21, No. 5, p. 1335-1343 (Apr. 6, 2009).
Carina Riediger et al:Fms-like tyrosine kinase 3 receptor ligand (Flt3L)-based vaccination administered with an adenoviral vector prevents tumor growth of colorectal cancer in a BALB/c mouse model 11 , Journal of Cancer Research and Clinical Oncology., vol. 139, No. 12, Oct. 10, 2013 (Oct. 10, 2013), pp. 2097-2110, XP055672630, DE ISSN: 0171-5216, DOI: 10.1007/s00432-013-1532-z * Figures 6, 8 *.
Rice et al. An H PV-E6/E7 immunotherapy plus PD-1 checkpoint inhibition results in tumor regression and reduction in PD-L 1 expression. Cancer Gene Therapy (2015) 22, 454-462.
Wu, et al., "Structure and function of vaccinia virus E3L protein." Journal of Biology, No. 2, pp. 64-83, (Apr. 13, 2013).
Benci et al., "Tumor Interferon Signaling Regulates a Multigenic Resistance Program to Immune Checkpoint Blockade." Cell. Dec. 1, 2016; 167(6): 1540-1554.e12.
Kirkwood et al., "High-Dose Interferon Alfa-2b Significantly Prolongs Relapse-Free and Overall Survival Compared With the GM2-KLH/QS-21 Vaccine in Patients With Resected Stage IIB-III Melanoma: Results of Intergroup Trial E1694/S9512/C509801." Journal of Clinical Oncology 19:2370-2380, 2001, American Society of Clinical Oncology.
Medrano et al., "Immunomodulatory and antitumor effects of type I interferons and their application in cancer therapy." Oncotarget, 2017, vol. 8, (No. 41), pp. 71249-71284.
Carroll et al., "Highly attenuated modified vaccinia virus Ankara (MVA) as an effective recombinant vector:a Murine tumor model", Vaccine, 15(4), pp. 387-394, 31.
Greiner et al., "The blockade of immune checkpoints in cancer immunotherapy", Nat Rev Cancer, 12(4), pp. 252-264, Mar. 22, 2012 (Mar. 22, 2012).

\* cited by examiner

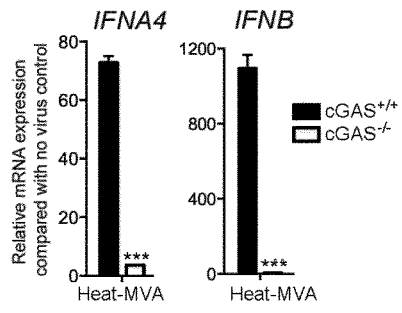
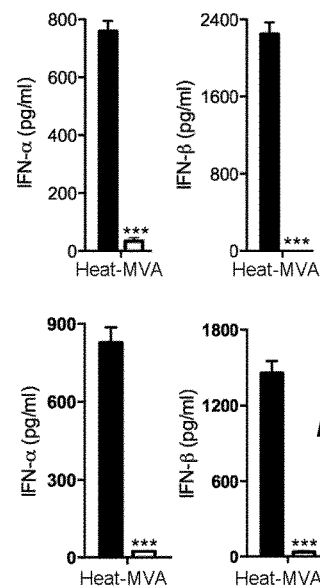
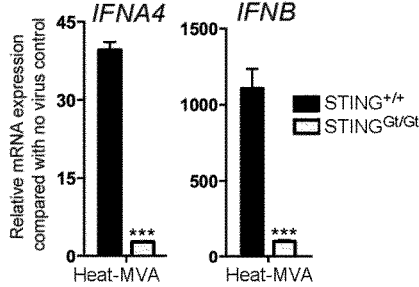
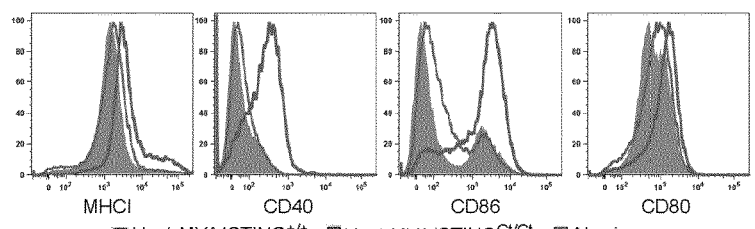
FIGURE 2G

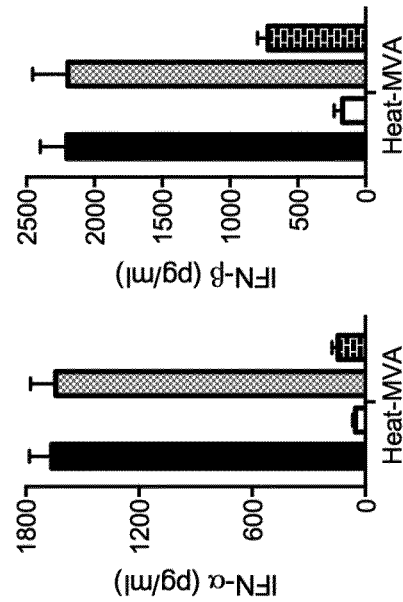
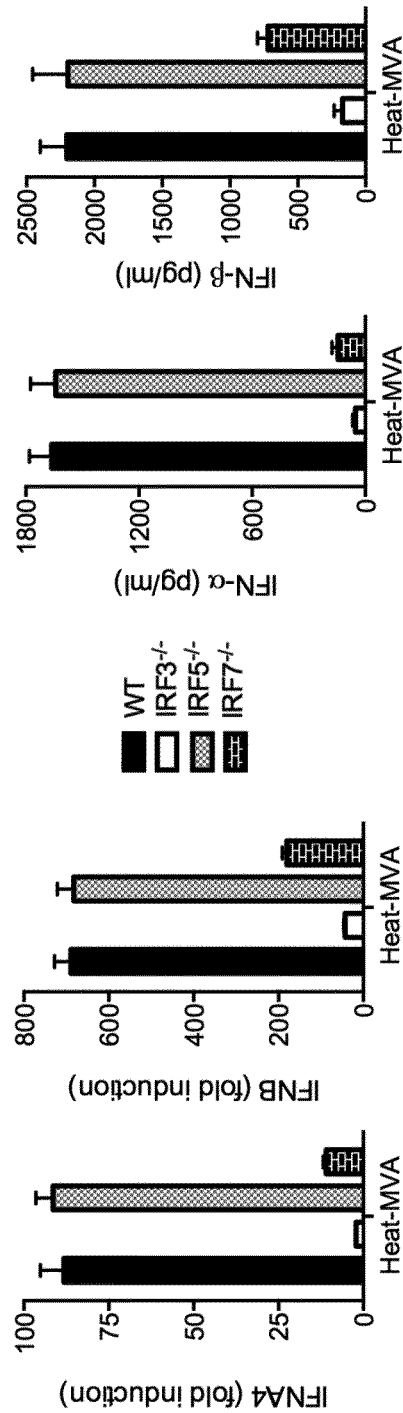
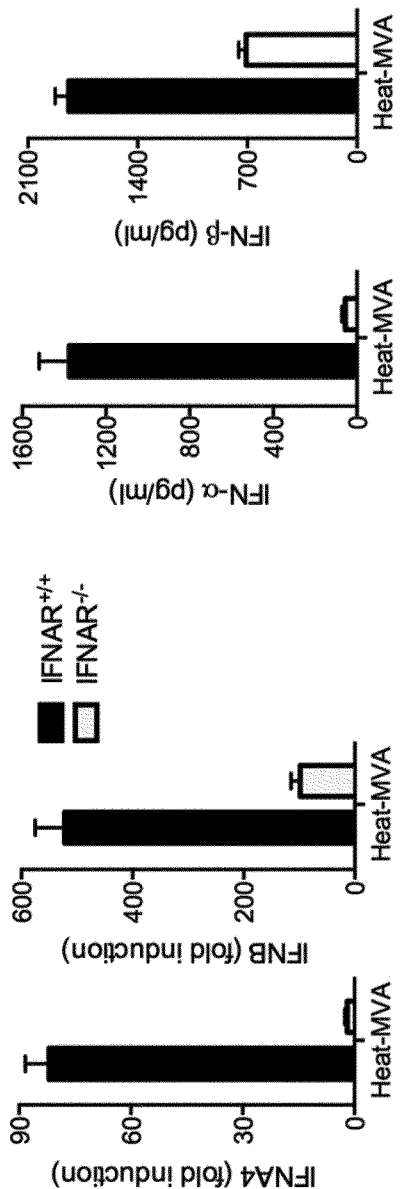

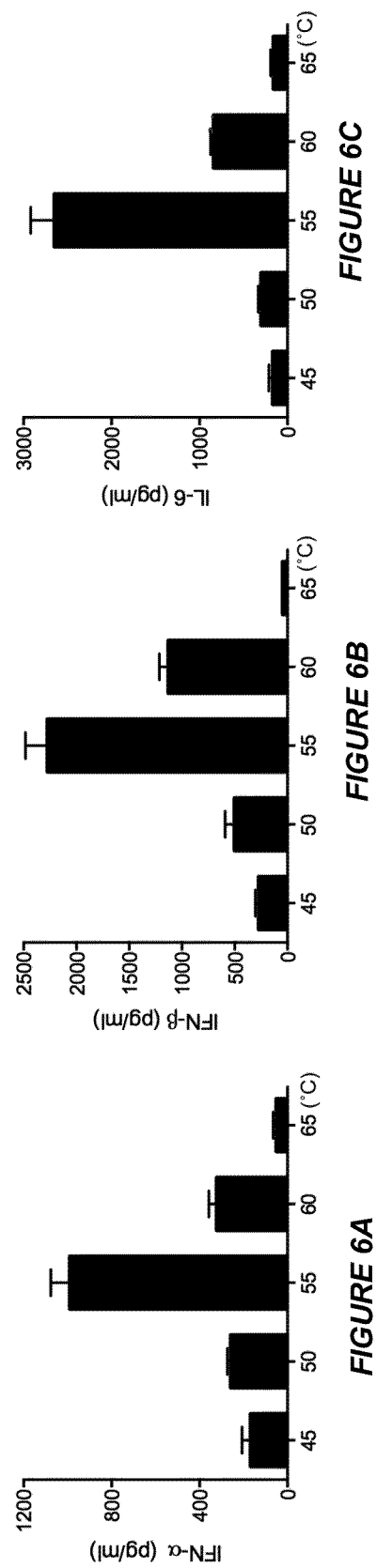

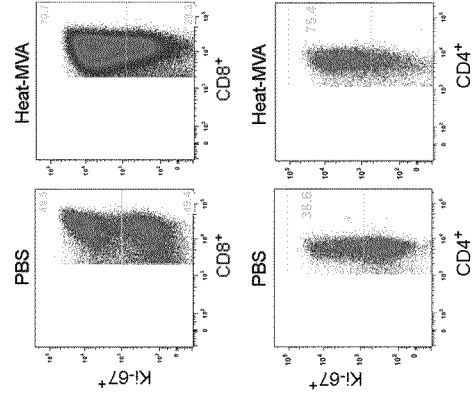
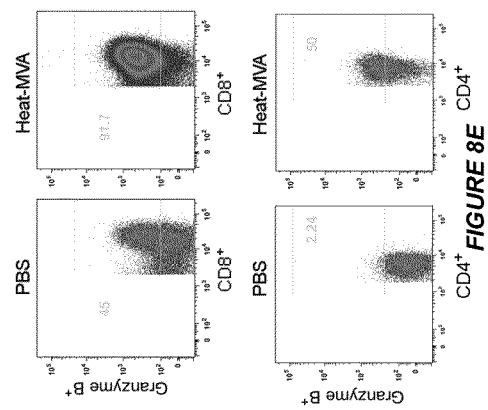
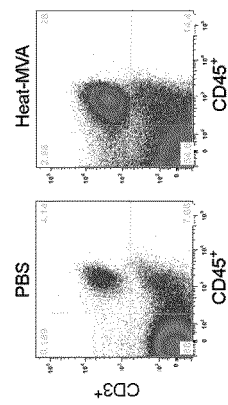
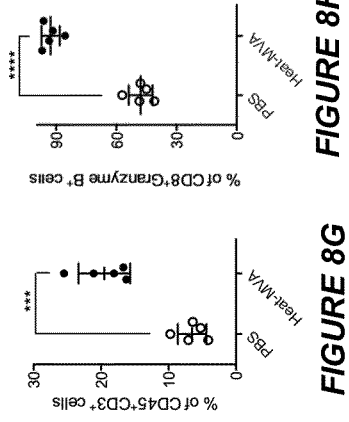

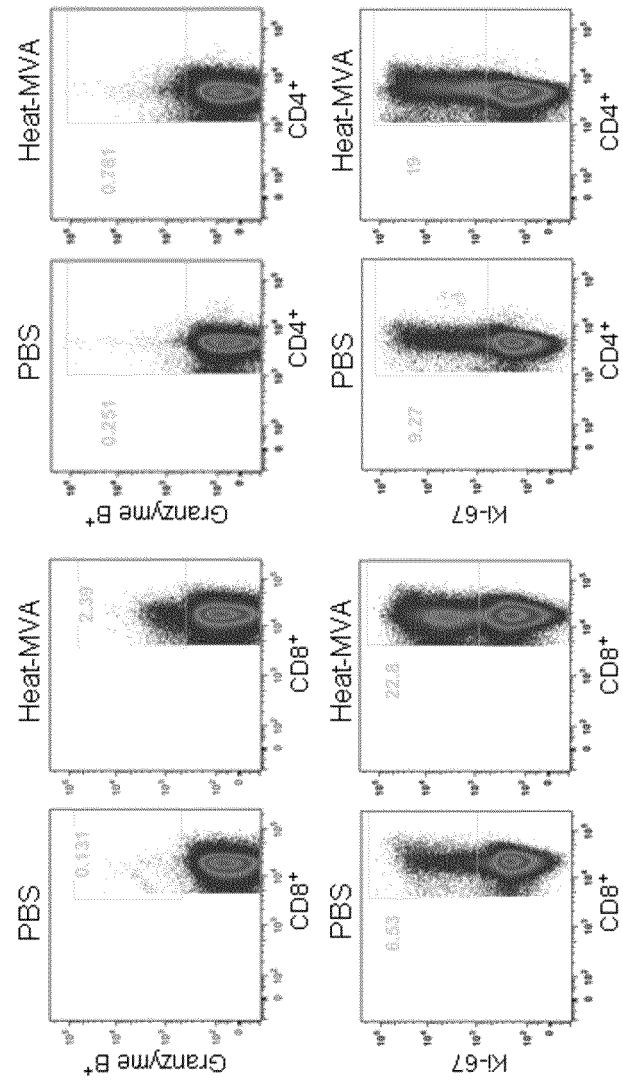

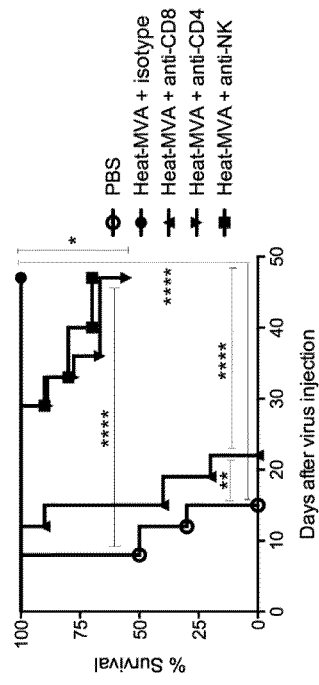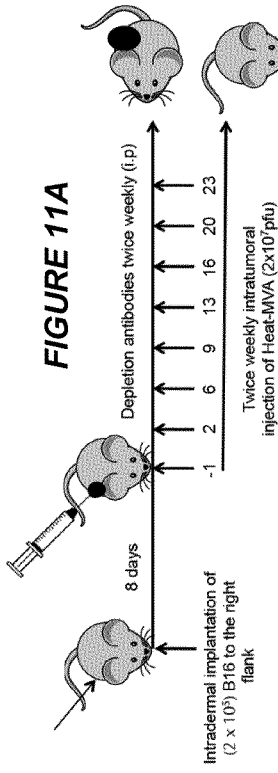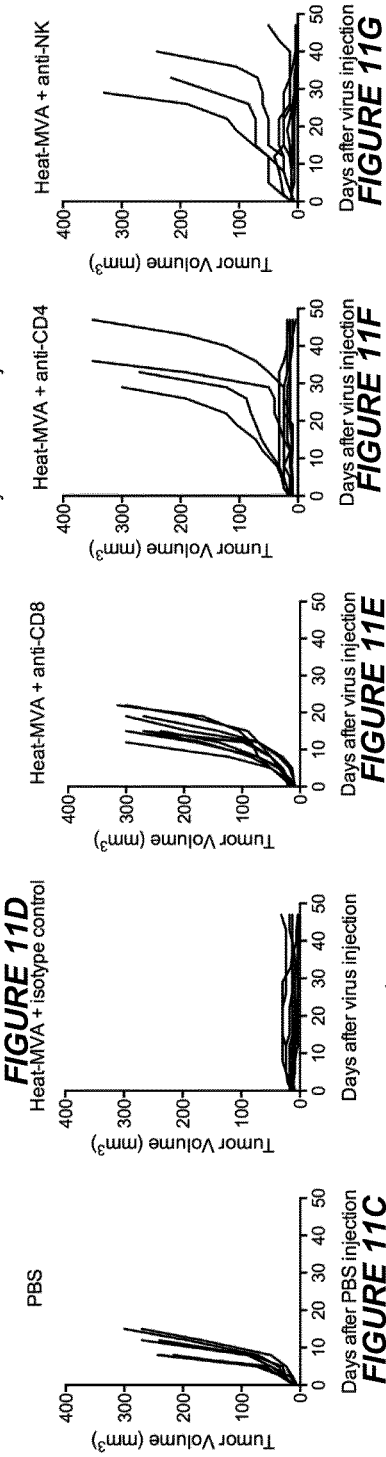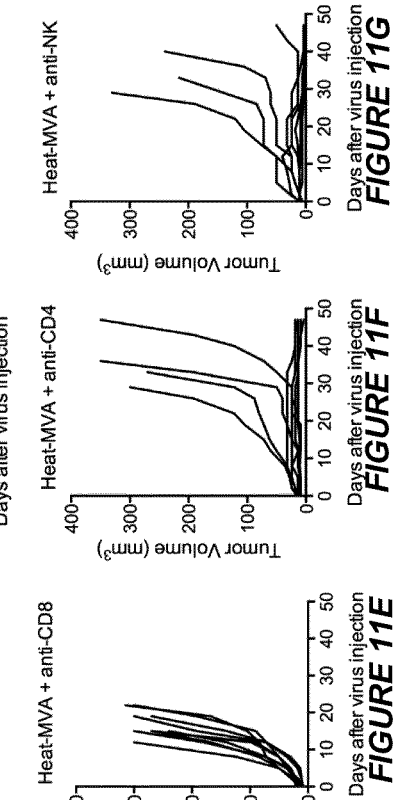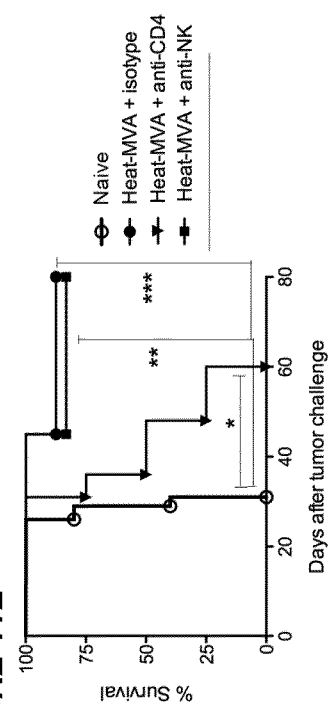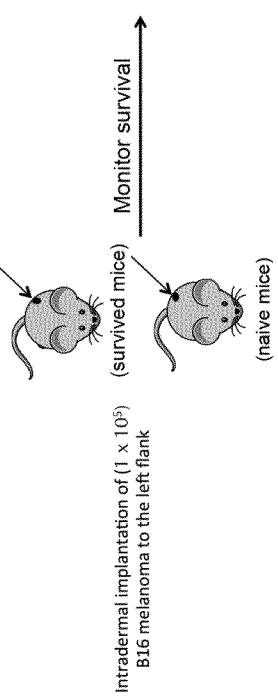

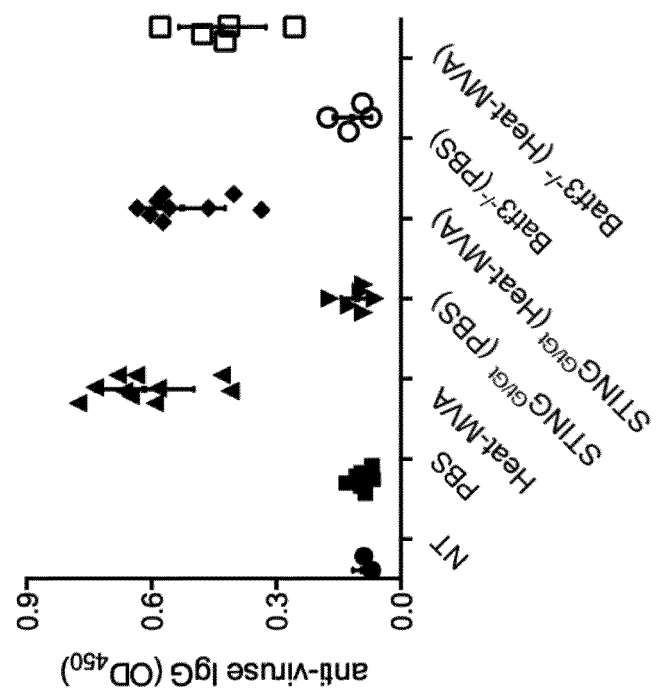
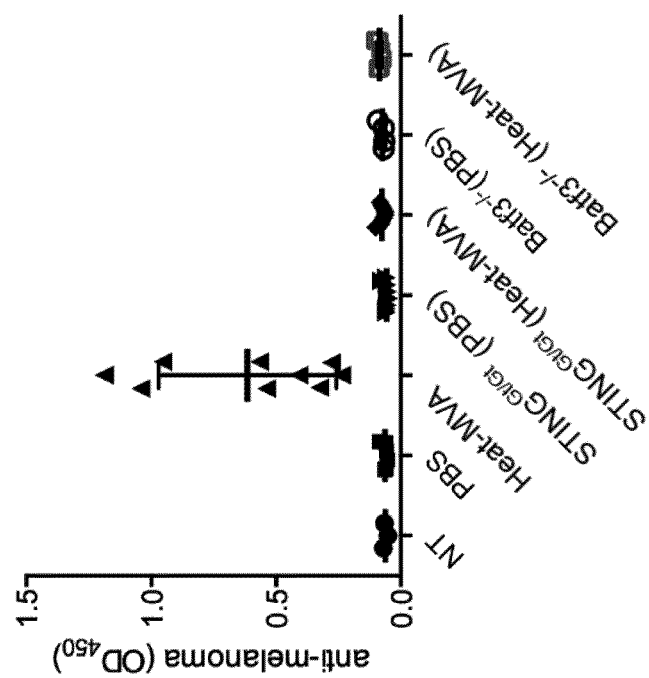
FIGURE 12A
FIGURE 12B

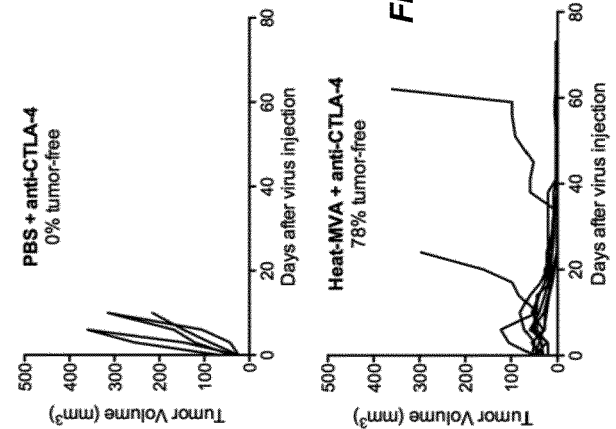
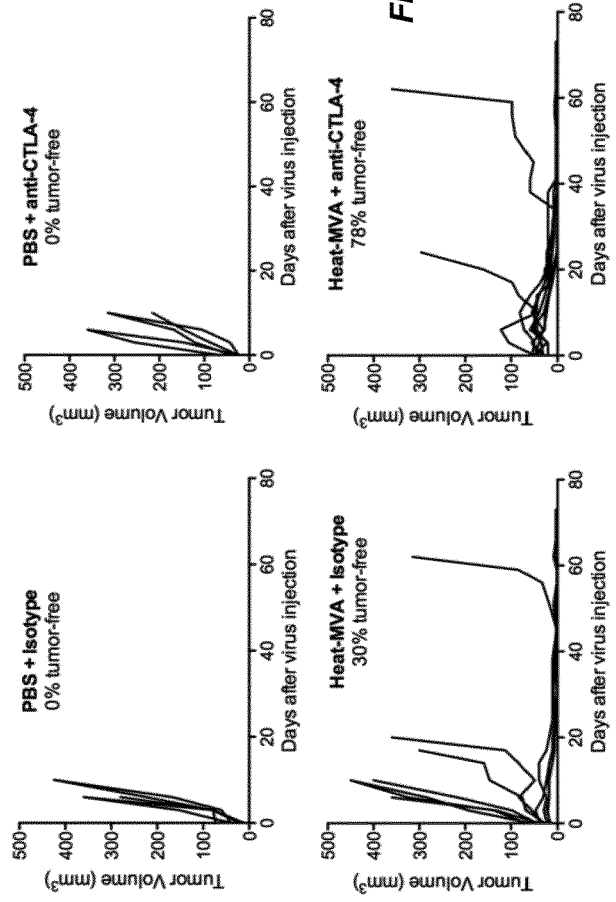
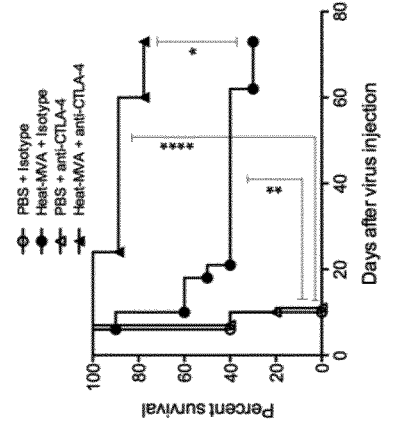
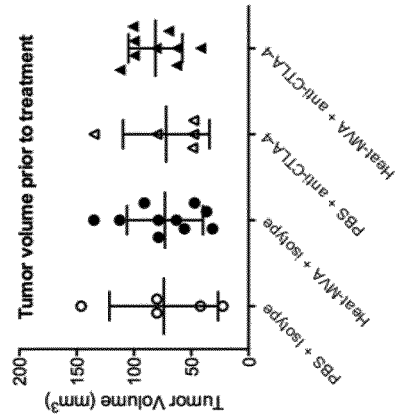

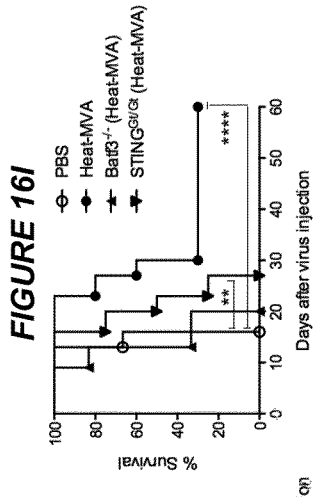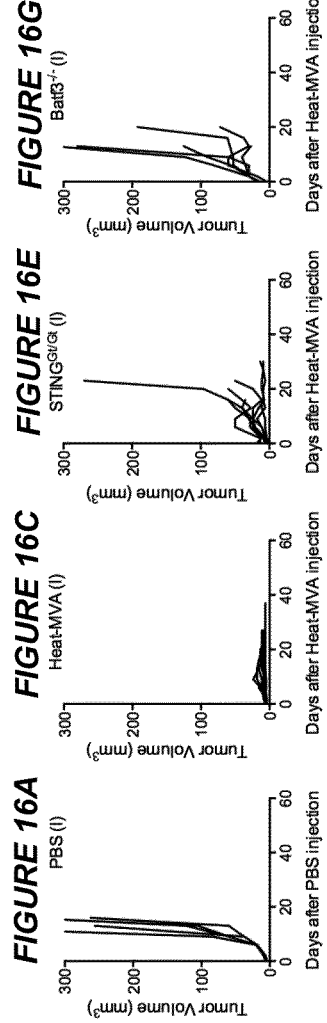

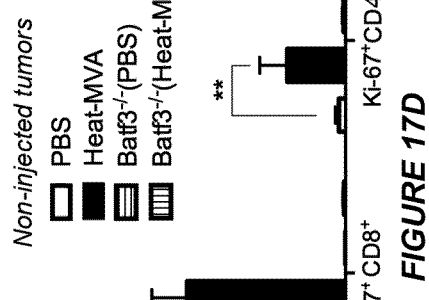
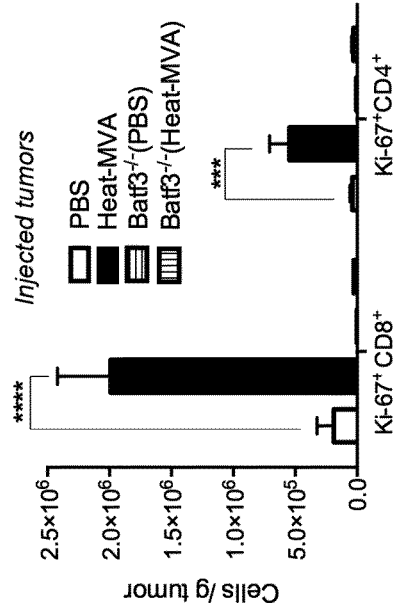
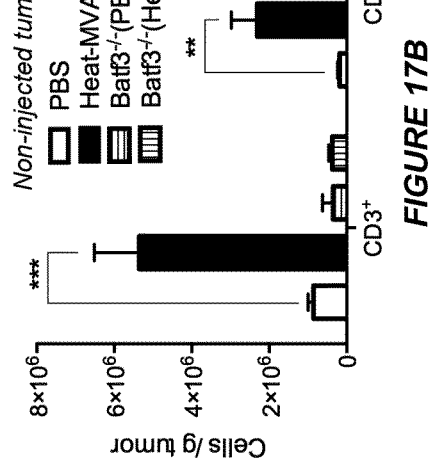
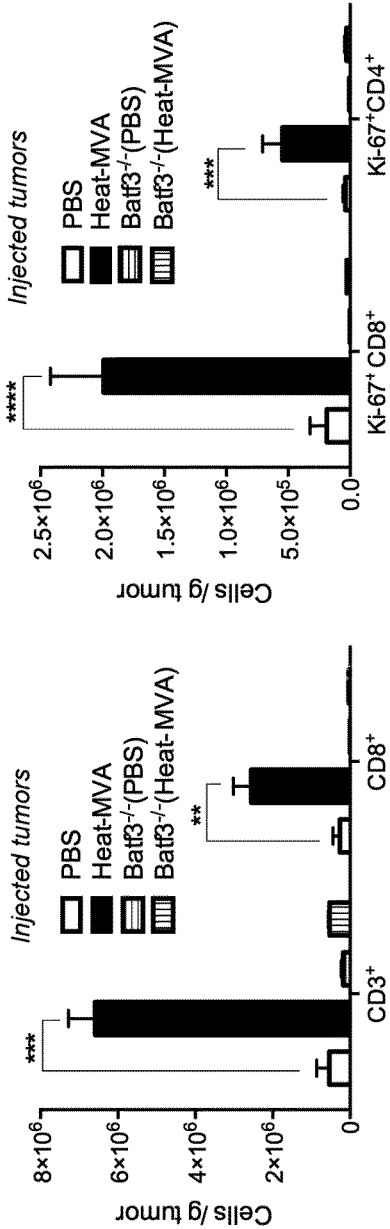

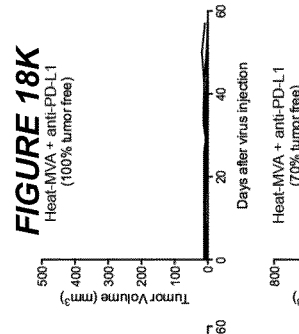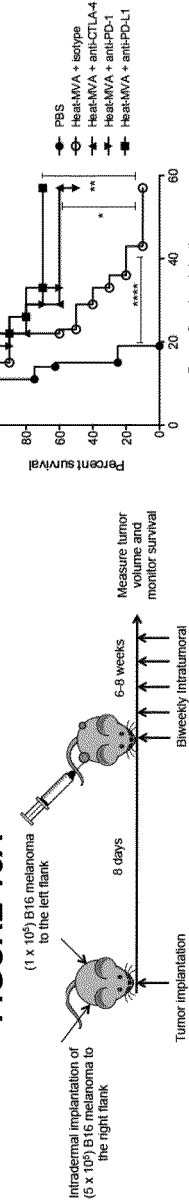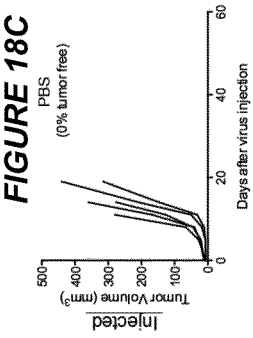
FIGURE 18A, FIGURE 18B, FIGURE 18C, FIGURE 18D, FIGURE 18E, FIGURE 18F, FIGURE 18G, FIGURE 18H, FIGURE 18I, FIGURE 18J, FIGURE 18K, FIGURE 18L

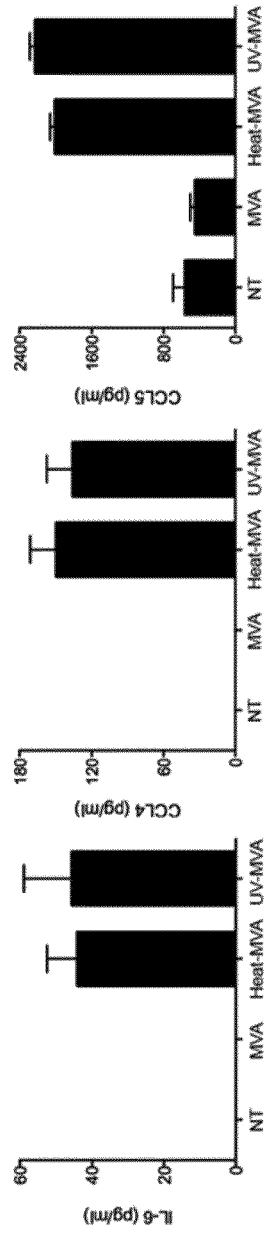
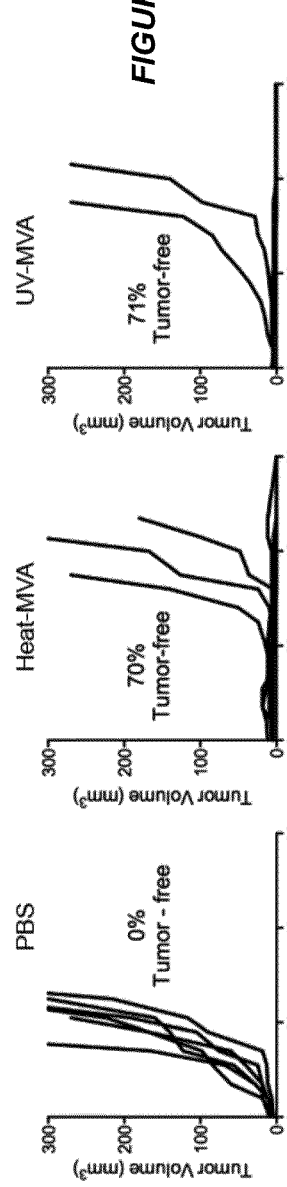
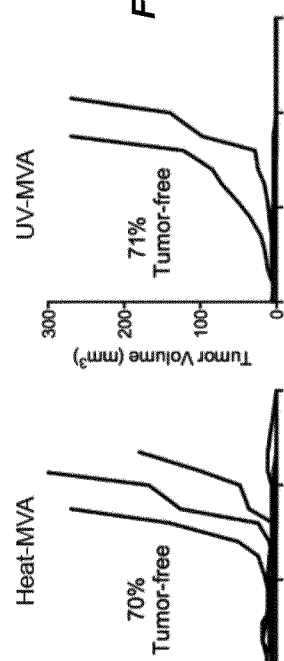
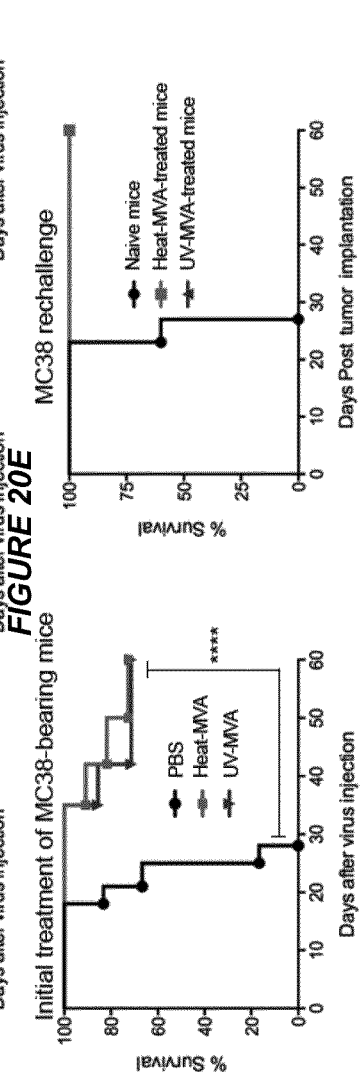

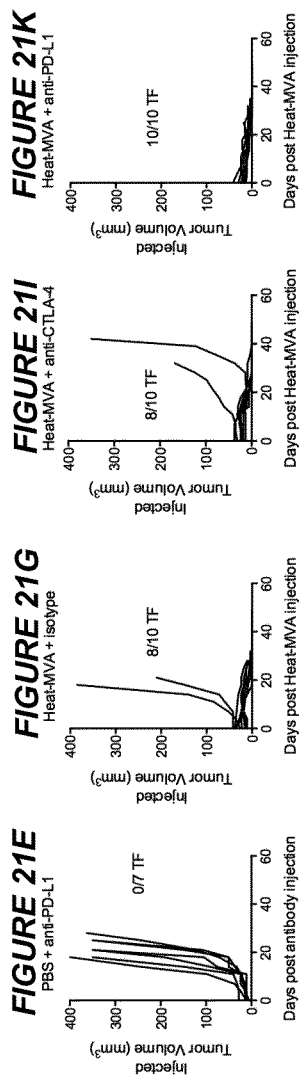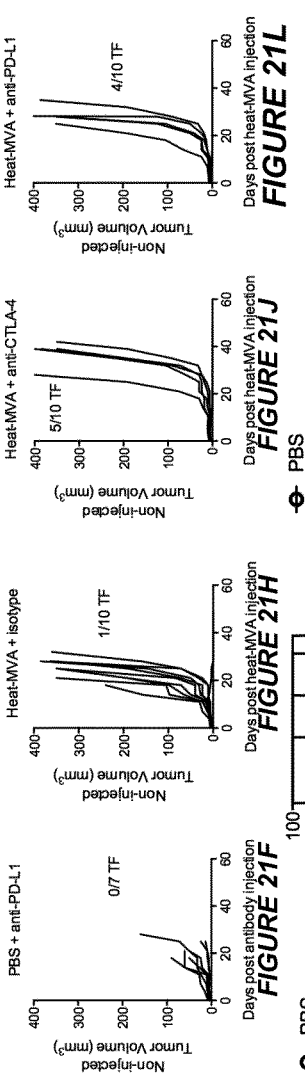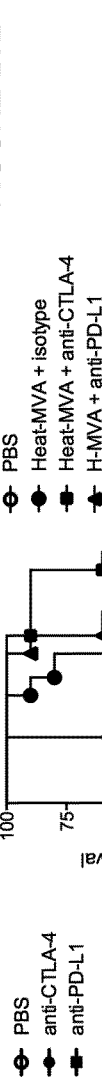

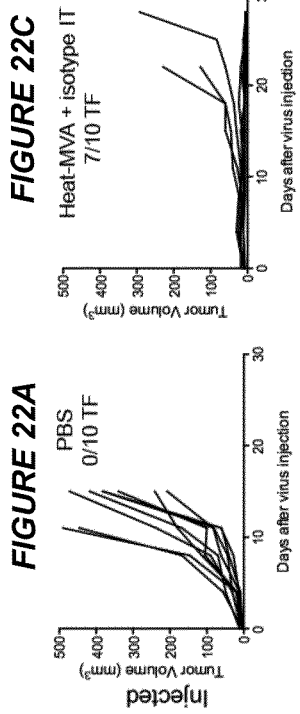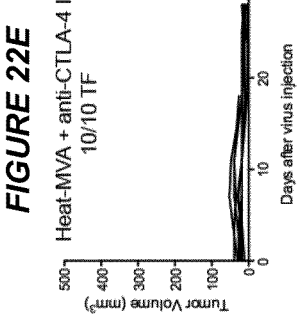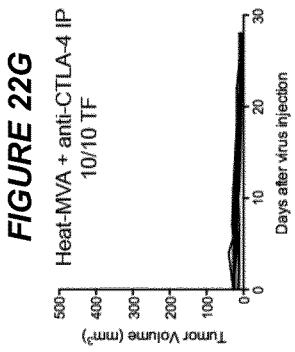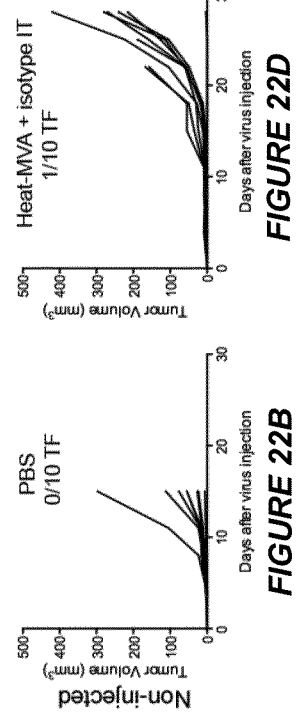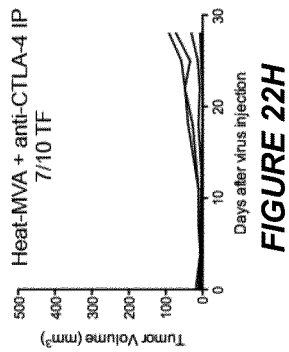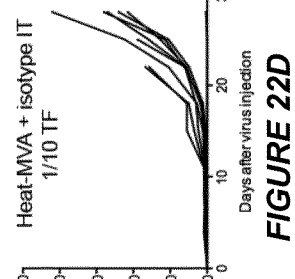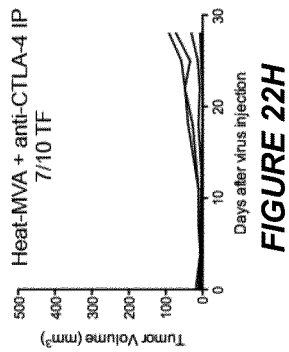

USE OF INACTIVATED NONREPLICATING MODIFIED VACCINIA VIRUS ANKARA (MVA) AS MONOIMMUNOTHERAPY OR IN COMBINATION WITH IMMUNE CHECKPOINT BLOCKING AGENTS FOR SOLID TUMORS

RELATED APPLICATIONS

This application is a continuation of U.S. patent application Ser. No. 15/553,222, filed Aug. 24, 2017, which is a U.S. National Stage Application of PCT/US2016/019663, filed Feb. 25, 2016, which claims priority from U.S. Provisional Application No. 62/120,862, filed Feb. 25, 2015, each of which are incorporated herein by reference in their entireties.

GOVERNMENT SUPPORT

This invention was made with government support under A1073736 and A1095692 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Mar. 28, 2019, is named 115872-0707_SL.txt and is 1,823 bytes in size.

FIELD OF THE INVENTION

The present invention relates generally to the fields of oncology, virology and immunotherapy. More particularly, it concerns the use of poxviruses, specifically inactivated modified vaccinia Ankara virus ("inactivated-MVA") which is infection-competent but nonreplicative and which has been further modified for example by heat or ultraviolet light (UV) irradiation. This inactivated MVA can be used as an immunotherapeutic agent for the treatment of cancer either as monotherapy or as a combination therapy in combination with immune checkpoint blockade therapies.

BACKGROUND

Immune System and Cancer

Malignant tumors are inherently resistant to conventional therapies and present significant therapeutic challenges. Immunotherapy has become an evolving area of research and an additional option for the treatment of certain types of cancers. The immunotherapy approach rests on the rationale that the immune system may be stimulated to identify tumor cells, and target them for destruction.

Numerous studies support the importance of the differential presence of immune system components in cancer progression [1]. Clinical data suggest that high densities of tumor-infiltrating lymphocytes are linked to improved clinical outcome [2]. The correlation between a robust lymphocyte infiltration and patient survival has been reported in various types of cancer, including melanoma, ovarian, head and neck, breast, urothelial, colorectal, lung, hepatocellular, gallbladder, and esophageal cancer [3]. Tumor immune infiltrates include macrophages, dendritic cells (DC), mast cells, natural killer (NK) cells, naïve and memory lymphocytes, B cells and effector T cells (T lymphocytes), primarily responsible for the recognition of antigens expressed by tumor cells and subsequent destruction of the tumor cells by T cells.

Despite presentation of antigens by cancer cells and the presence of immune cells that could potentially react against tumor cells, in many cases the immune system does not get activated. Key to this phenomenon is the ability of tumors to protect themselves from immune response by coercing cells of the immune system to inhibit other cells of the immune system. For example, $CD4^+$ T cells possess the ability to differentiate into T regulatory (Treg) cells, which have the ability to inhibit activated T cells. Additionally, cancer cells can impair $CDS^+$ T cell effector function, leading to the evasion of anti-tumor immune response. Finally, the local immunosuppressive nature of the tumor microenvironment, along with immune editing, can lead to the escape of cancer cell subpopulations that do not express the target antigens. This, finding a method to that would allow for the preservation and/or restoration of anti-tumor activities of the immune system is of paramount importance.

It has been established that type I IFN plays important roles in host antitumor immunity [4]. IFNAR1-deficent mice are more susceptible to developing tumors after implantation of tumor cells. Spontaneous tumor-specific T cell priming is also defective in IFNAR1-deficient mice [5, 6]. More recent studies have shown that the cytosolic DNA-sensing pathway is important in the recognition of tumor-derived DNA by the innate immune system. In turn, this leads to the development of antitumor $CD8^+$ T cell immunity [7]. This pathway also plays an important role in radiation-induced antitumor immunity [8].

Melanoma

Melanoma, one of the deadliest cancers, is the fastest growing cancer in the US and worldwide. Its incidence has increased by 50% among young Caucasian women since 1980, primarily due to excess sun exposure and the use of tanning beds. According to the American Cancer Society, approximately 76,380 people in the US will be diagnosed with melanoma and 10,130 people (or one person per hour) are expected to die of melanoma in 2016. In most cases, advanced melanoma is resistant to conventional therapies, including chemotherapy and radiation. As a result, people with metastatic melanoma have a very poor prognosis, with a life expectancy of only 6 to 10 months. The discovery that about 50% of melanomas have mutations in BRAF (a key tumor-promoting gene) opened the door for targeted therapy in this disease. Early clinical trials with BRAF inhibitors showed remarkable, but unfortunately not sustainable responses in patients with melanomas with BRAF mutations. Therefore, alternative treatment strategies for these patients, as well as patients with melanoma without BRAF mutations, are urgently needed.

Human pathological data indicate that the presence of T-cell infiltrates within melanoma lesions correlates positively with longer patient survival [9]. The importance of the immune system in protection against melanoma is further supported by partial success of immunotherapies, such as the immune activators IFN-α2b and IL-2 [10] as well as the unprecedented clinical responses of patients with metastatic melanoma to immune checkpoint blockade therapy, including anti-CTLA-4 and anti-PD-1/PD-L1 used either individually or in combination [11-17]. However, many patients fail to respond to immune checkpoint blockade therapy alone. The addition of virotherapy might overcome resistance to immune checkpoint blockade, which is supported by animal tumor models [18].

Poxviruses

Poxviruses, such as engineered vaccinia viruses, are in the forefront as oncolytic therapy for metastatic cancers [19]. Vaccinia viruses are large DNA viruses, which have a rapid life cycle [20]. Poxviruses are well suited as vectors to express multiple transgenes in cancer cells and thus to enhance therapeutic efficacy [21]. Preclinical studies and clinical trials have demonstrated efficacy of using oncolytic vaccinia viruses and other poxviruses for treatment of advanced cancers refractory to conventional therapy [22-24]. Poxvirus-based oncolytic therapy has the advantage of killing cancer cells through a combination of cell lysis, apoptosis, and necrosis. It also triggers the innate immune sensing pathway that facilitates the recruitment of immune cells to the tumors and the development of anti-tumor adaptive immune responses. The current oncolytic vaccinia strains in clinical trials (JX-594, for example) use wild-type vaccinia with deletion of thymidine kinase to enhance tumor selectivity, and with expression of transgenes such as granulocyte macrophage colony stimulating factor (GM-CSF) to stimulate immune responses [21]. Many studies have shown however that wild-type vaccinia has immune suppressive effects on antigen presenting cells (APCs) [25-28] and thus adds to the immunosuppressive and immunoevasive effects of the tumors themselves.

Poxviruses are extraordinarily adept at evading and antagonizing multiple innate immune signaling pathways by encoding proteins that interdict the extracellular and intracellular components of those pathways [29]. Modified vaccinia virus Ankara (MVA) is an attenuated vaccinia virus that was developed through serial passaging in chicken embryonic fibroblasts. MVA has a 31-kb deletion of the parental vaccinia genome and was used successfully as a vaccine during the WHO-sponsored smallpox eradication campaign [30-32]. MVA has been investigated intensively as a vaccine vector against HIV, tuberculosis, malaria, influenza, and coronavirus, as well as cancers [33-38].

MVA has deletions or truncations of several intracellular immunomodulatory genes including K1L, N1L, and A52R, which have been implicated in regulating innate immune responses [39-46]. On the other hand, MVA retains the E3L gene encoding a bifunctional Z-DNA/dsRNA binding protein, a key vaccinia virulence factor [47-55]. It has been shown that MVA infection of human monocyte-derived dendritic cells causes DC activation [56]. Waibler et al. [57] reported that MVA infection of murine Flt3L-DC triggered a TLR-independent type I IFN response. In addition, MVA infection of human macrophages triggers type I IFN and pro-inflammatory cytokines and chemokines via a TLR2/TLR6/MyD88 and MDA5/MAVS-dependent pathways [58].

The sensing of DNA in the cytosol triggers a cascade of events leading to the production of type I IFN and cytokines as well as cellular stress responses. STING (stimulator of IFN genes) was identified as an important adaptor for the cytosolic DNA-sensing pathway [59-61]. The nature of the DNA sensors remained elusive until the discovery of cyclic GMP-AMP synthase (cGAS) as the critical DNA sensor, and its product cyclic GMP-AMP, which contains an unanticipated 2',5' linkage at the GpA step and standard 3',5' linkage at the ApG step [62-68] Subsequent research confirmed STING as the key adaptor activated by cGAMP, thereby mediating the cascade of downstream events involving kinases and transcription factors that lead to the interferon response [66, 68, 69]. We reported that MVA infection of murine conventional dendritic cells induces type I IFN via a cytosolic DNA-sensing pathway mediated by cytosolic DNA sensor cGAS, its adaptor STING, and transcription factors IRF3 and IRF7. By contrast, wild-type vaccinia virus fails to activate this pathway. Intravenous inoculation of MVA via tail-vein injection induced type I IFN secretion in WT mice, which was diminished in STING or IRF3-deficient mice [70]. Furthermore, we showed that vaccinia virulence factors E3 and N1 play inhibitory roles in the cytosolic DNA-sensing pathway [70].

SUMMARY OF THE DISCLOSURE

In one aspect, the present disclosure provides a method for treating a subject afflicted with one or more solid malignant tumors, the method comprising delivering to cells of the tumor inactivated modified vaccinia Ankara (inactivated MVA) and thereby treating the tumor.

In another aspect, a method is provided for treating a solid malignant tumor in a subject comprising delivering to tumor cells of the subject an amount of inactivated-MVA effective to induce the immune system of the subject to mount an immune response against the tumor.

In yet another aspect, the disclosure provides a method for treating a malignant tumor in a subject, the method comprising a combination of delivering to tumor cells of the subject inactivated-MVA in an amount effective to induce the immune system of the subject to mount an immune response against the tumor and conjointly administering to the subject a second amount of an immune checkpoint blocking agent effective to block an immune checkpoint expressed by the tumor, thereby treating the tumor. As used herein, "delivering" means "administering;" the former is mostly used in connection with inactivated MVA, the latter in connection with immune checkpoint blocking agents.

It will be understood that unless stated explicitly to the contrary, the embodiments described below shall pertain to each of the foregoing aspects and that features of further or more specific embodiments may be presented individually within a particular aspect or one or more of them may be combined.

In some embodiments, the amount of inactivated MVA is effective to accomplish one or more of the following:
  a. induce the immune system of the subject to mount an immune response against the tumor;
  b. reduce the size of the tumor;
  c. eradicate the tumor;
  d. inhibit growth of the tumor;
  e. inhibit metastasis of the tumor; and
  f. reduce or eradicate metastatic tumor.

In some embodiments, the treated tumor includes tumor located at the site of inactivated MVA delivery, or tumor located both at said site and elsewhere in the body of the subject. In other words, the effect of MVA delivery is systemic even though the inactivated MVA may be delivered to only one or only a plurality of solid tumors of the subject.

In more specific embodiments, the immune response comprises on or more of the following:
  a. increase in cytotoxic CD8$^+$ T cells within the tumor and/or in tumor-draining lymph nodes;
  b. induction of maturation of dendritic cells infiltrating said tumor through induction of type I IFN;
  c. induction of activated CD4$^+$ effector T cells in the subject recognizing tumor cells within the tumors or systemically;
  d. reduction in immune suppressive (regulatory) CD4$^+$ T cells within the tumor; and e. induction of cells of the tumor to express MEW Class I on their surface and to produce one or more of Type I IFN and other inflammatory cytokines and chemokines.

In some embodiments, the tumor is primary or metastatic melanoma or primary or metastatic colon carcinoma.

In some embodiments, the subject is a human.

In some embodiments, the delivery of the inactivated MVA is repeated in spaced apart time intervals; in more specific embodiments, the repeated delivery continues for several weeks, months or years or indefinitely as long as benefits persist or a maximum tolerated dose is reached; in further embodiments, the delivery of inactivated MVA is repeated with a frequency within the range from once per month to two times per week; in some more specific embodiments, the delivery is repeated once weekly.

In some embodiments, delivery of the inactivated MVA is by parenteral route; in more specific embodiments by intratumor injection or intravenous injection.

In some embodiments, the inactivated-MVA is delivered at a dosage per administration within the range of about $10^5$-$10^{10}$ plaque-forming units (pfu); in more specific embodiments, it is delivered at a dosage per administration within the range of about $10^6$ to about $10^9$ plaque-forming units (pfu).

In some embodiments, the inactivated MVA is UV-inactivated MVA; in other embodiments, it is heat-inactivated MVA; in yet other embodiments, a combination of heat- and UV-inactivated MVA.

In some embodiments, the induction and activation of effector T cells is accompanied by a reduction of regulatory $CD4^+$ cells in said tumor; in some embodiments, the inactivated-MVA induces maturation of dendritic cells infiltrating said tumor through induction of type I IFN; in some embodiments, the inactivated MVA induces the expression of MEW Class I and the induction of one or more of type I interferon and other inflammatory cytokines and chemokines in infected tumor cells.

In some embodiments, the induced immune response effects or contributes to one or more of the following: reduction of the size of the tumor, eradication of the tumor, inhibition of tumor or metastatic growth. Again, the tumor is not confined to the tumor injected with inactivated MVA.

Specific embodiments within the third aspect mentioned above include the foregoing and additional ones as follows:

In some embodiments, the delivery of the inactivated MVA is by intratumoral injection and the administration of the immune checkpoint blocking agents by intravenous route; in other embodiments, both the delivery and the administration are by intravenous route; in yet other embodiments, both the delivery and the administration are by intratumoral injection. In some embodiments, the immune checkpoint blocking agent is selected from the group consisting of anti-PD-1 inhibitors, PD-L1, inhibitors and CTLA4 inhibitors, which in specific embodiments are antibodies In some embodiments, the inactivated MVA is delivered and the immune checkpoint blocking agents administered each according to its own administration schedule of spaced apart intervals. In some embodiments, the delivery and administration occur in parallel during the same overall period of time.

In some embodiments, a first dose of the inactivated MVA is delivered first and after a lapse of time, for example a week, a first dose of the immune checkpoint blocking agent is administered. In some embodiments, one or both of the inactivated MVA and the immune checkpoint blocking agent are respectively delivered and administered during a period of time of several weeks, months or years, or indefinitely as long as benefits persist and a maximum tolerated dose is not reached.

In some embodiments, the immune checkpoint blocking agent and the inactivated MVA are administered simultaneously; in some embodiments, they are administered in the same composition; in some embodiments, they are both delivered intratumorally. In some embodiments, simultaneous delivery permits a lower dose of the immune check point blocking agent to be employed and the combined effect of the two active agents can be synergistic.

Any feature or combination of features of any embodiment or chosen among multiple embodiments that is or are disclosed may be excluded.

BRIEF DESCRIPTION OF THE DRAWINGS

FIG. 1A are bar graphs of relative IFNA4 and IFNB mRNA expression levels compared to no virus control in cDCs (GM-CSF-cultured bone marrow derived DCs) infected with MVA at a MOI of 10 or with an equivalent amount of Heat-MVA. Data are means±SEM (n=3). A representative experiment is shown, repeated at least twice. FIG. 1B are graphs of the concentrations of secreted IFN-α and IFN-β in the medium over time following MVA or Heat-MVA infection of cDCs (***, p<0.001). Data are means±SEM (n=3). A representative experiment is shown, repeated at least twice. FIG. 1C is a scanned image of a Western Blot showing protein levels of p25 of vaccinia E3, p-IRF-3, and β-actin (as a loading control). "hpi", hours post infection. "M", mock infection control.

FIGS. 2A-G are a series of graphical representations of data showing that Heat-MVA induced type I IFN production is dependent on the cytosolic DNA-sensing pathway mediated by cGAS and STING. FIG. 2A is a bar graph of IFNA4 and IFNB relative mRNA expression compared with no virus control in cDCs generated from $cGAS^{+/+}$ and $cGAS^{-/-}$ mice and infected with Heat-MVA (*, p<0.001). Data are means±SEM (n=3). A representative experiment is shown, repeated twice. FIG. 2B is a bar graph of the concentrations of secreted IFN-α and IFN-β in the medium of cDCs generated from $cGAS^{+/+}$ and $cGAS^{-/-}$ mice and infected with Heat-MVA (*, p<0.001). Data are means±SEM (n=3). A representative experiment is shown, repeated twice. FIG. 2C is a bar graph of IFNA4 and IFNB relative mRNA expression compared with no virus control in cDCs generated from $STING^{+/+}$ and $STING^{Gt/Gt}$ mice and infected with Heat-MVA (*, p<0.001). Data are means±SEM (n=3). A representative experiment is shown, repeated at least twice. FIG. 2D is a bar graph of the concentrations of secreted IFN-α and IFN-β in the medium of cDCs generated from $STING^{+/+}$ and $STING^{Gt/Gt}$ mice and infected with Heat-MVA (*, p<0.001). Data are means±SEM (n=3). A representative experiment is shown, repeated at least twice. FIG. 2E is a scanned image of a Western Blot showing protein levels of p-IRF3 and β-actin in $cGAS^{+/+}$ and $cGAS^{-/-}$ cDCs following Heat-MVA infection. "hpi", hours post infection. "M", mock infection control. FIG. 2F is a scanned image of a Western Blot showing protein levels of p-IRF3 and β-actin in $STING^{+/+}$ and $STING^{Gt/Gt}$ cDCs following Heat-MVA infection. "hpi", hours post infection. "M", mock infection control. FIG. 2G is a series of graphs showing the expression of surface markers MHCI (MHC class I), CD40, CD86, and CD80 in Heat-MVA infected cDCs generated from STING$^{Gt/Gt}$ and WT mice. A representative experiment is shown, repeated at least twice.

FIGS. 3A-D are a series of graphs showing that Heat-MVA induced type I IFN production is dependent on transcription factors IRF3, IRF7, and IFNAR1. FIG. 3A is a graph depicting fold induction of IFNA4 and IFNB mRNA expression following Heat-MVA infection of cDCs generated from WT, IRF3$^{-/-}$, IRF5$^{-/-}$, and IRF7$^{-/-}$ mice. Data are means±SEM (n=3). A representative experiment is shown, repeated twice. FIG. 3B is a graph depicting the concentrations of secreted IFN-α and IFN-β in the medium of heat-MVA-infected cDCs generated from WT, IRF3$^{-/-}$, IRF5$^{-/-}$, and IRF7$^{-/-}$ mice Data are means±SEM (n=3). A representative experiment is shown, repeated twice. FIG. 3C is a bar graph showing fold induction of IFNA4 and IFNB mRNA following Heat-MVA infection of cDCs generated from IFNAR$^{+/+}$ and IFNR$^{-/-}$ mice Data are means±SEM (n=3). A representative experiment is shown, repeated twice. FIG. 3D is a bar graph showing the concentrations of secreted IFN-α and IFN-β in the medium of heat-MVA-infected cDCs generated from IFNAR$^{+/+}$ and IFNR$^{-/-}$ mice. Data are means±SEM (n=3). A representative experiment is shown, repeated twice.

FIG. 4A is a scatterplot of the concentrations of the secreted IFN-α and IFN-β in the serum from WT mice inoculated with MVA ($2\times10^7$ pfu) or an equivalent amount of Heat-MVA via tail vein injections. Serum was collected at 6 h post inoculation (*, p<0.001; n=5). A representative experiment is shown, repeated twice. FIG. 4B is a scatterplot of the concentrations of the secreted IFN-α and IFN-β in the serum from IFNAR$^{+/+}$ or IFNR$^{-/-}$ mice inoculated with Heat-MVA (, p<0.01; ***, p<0.001; n=5). A representative experiment is shown, repeated twice. FIG. 4C is a scatterplot of the concentrations of the secreted IFN-α and IFN-β in the serum from WT, IRF3$^{-/-}$, IRF7$^{-/-}$, or STING$^{Gt/Gt}$ mice inoculated with Heat-MVA (n=5). A representative experiment is shown, repeated twice.

FIG. 5A is a series of bar graphs showing the fold induction of mRNA levels of IFNA4, IFNB, CCL5, and IL6 following Heat-MVA or MVA infection of B16-F10 melanoma cells. Data are means±SEM (n=3). A representative experiment is shown, repeated twice. FIG. 5B is a series of bar graphs showing the concentrations of secreted IFN-α and IFN-β, CCL5, and IL-6 in the medium of B16-F10 melanoma cells following Heat-MVA or MVA infection. Data are means±SEM (n=3). A representative experiment is shown, repeated twice. FIG. 5C is a scanned image of a Western Blot showing p-IRF, IRF, and GAPDH protein levels (as a loading control) in B16-F10 cells infected with Heat-MVA or MVA. "hpi", hours post infection. FIG. 5D is a graph of WWI expression in B16-F10 cells infected with no virus control, MVA, or Heat-MVA. A representative experiment is shown, repeated twice.

FIGS. 6A-C are a series of graphical representations of data showing that MVA treated with heat-inactivation at 55° C. for 1 h induced highest levels of IFN secretion from cDCs. FIGS. 6A, 6B, and 6C are bar graphs of the concentrations respectively of secreted IFN-α (A) and IFN-β (B) and IL-6 (C) in the medium of cDCs infected with MVA heat-treated at different temperatures for 1 hour. Data are means±SEM (n=3). A representative experiment is shown, repeated twice.

FIG. 7A is a plot of tumor volume against time (days) after PBS (open circles; n=5) or Heat-MVA (filled circles; n=10) injection. A representative experiment is shown, repeated at least five times. FIG. 7B is a Kaplan-Meier survival curve of tumor-bearing mice injected with PBS (open circles; n=5) or Heat-MVA (filled circles; n=10) (**, p<0.0001). A representative experiment is shown, repeated at least five times. FIG. 7C is a Kaplan-Meier survival curve of naïve mice (open circles; n=5) and Heat-MVA-treated mice (filled circles; n=10) re-challenged at the contralateral side with a lethal dose of B16-F10 melanoma cells ($1\times10^6$ cells). A representative experiment is shown, repeated at least five times. FIG. 7D is a scatterplot of the number of tumor foci on the surface of lungs collected at 3 weeks from either naïve mice (open circles; n=9) or Heat-MVA-treated mice (filled circles; n=10) after intravenous delivery of $1\times10^6$ cells (**, p<0.0001). A representative experiment is shown, repeated at least twice.

FIGS. 8A-L are a series of graphical representations of data showing that intratumoral injection of Heat-MVA leads to immunological changes in the tumor microenvironment. FIG. 8A is the flow cytometric analysis of CD3$^+$CD45$^+$ T cells. FIGS. 8B-C are scatterplots of flow cytometric analysis of CD8$^+$ cells expressing Granzyme B$^+$ (8B) or Ki-67 (8C). FIGS. 8D-F are scatterplots of flow cytometric analysis of CD4$^+$ cells expressing FoxP3 (8D), Granzyme B (8E), or Ki-67 (8F). FIGS. 8G-L are scatterplots of percentages of CD45$^+$CD3$^+$ (8G), CD8$^+$Granzyme B$^+$ (8H), CD8$^+$Ki-67$^+$ (8I), CD4$^+$Foxp3$^+$ (8J), CD4$^+$Granzyme B$^+$ (8K), and CD4$^+$Ki67$^+$ (8L) cells within tumors of mice treated with PBS (n=5) or Heat-MVA (n=5; *, p<0.001; **, p<0.0001). A representative experiment is shown, repeated twice.

FIGS. 9A-H are a series of graphical representations of data showing that Heat-MVA induces immunological changes in the tumor draining lymph nodes (TDLNs). FIGS. 9A-D are scatterplots of flow cytometric analysis of Granzyme B$^+$CD8$^+$ (9A), Granzyme B$^+$CD4$^+$ (9B), Ki-67$^+$CD8$^+$ (9C), and Ki67$^+$CD4$^+$ (9D) cells isolated from TDLNs of PBS (n=5) or Heat-MVA (n=5) treated mice. FIGS. 9E-H are graphs depicting percentages of Granzyme B$^+$CD8$^+$ (9E), Ki67$^+$CD8$^+$ (9F), Granzyme B$^+$CD4$^+$ (9G), and Ki67$^+$CD4$^+$ (9H) cells in TDLNs (n=5; *, p<0.001; **, p<0.0001). A representative experiment is shown, repeated twice.

FIG. 10A is a graph of tumor volume v. time (days) following PBS or Heat-MVA injection in tumor-bearing WT, STING$^{Gt/Gt}$, and Batf3$^{-/-}$ mice. FIG. 10B is a Kaplan-Meier survival curve of tumor-bearing WT, STING$^{Gt/Gt}$, and Batf3$^{-/-}$ mice treated with PBS or Heat-MVA (n ranges from 5-8 for different groups; , p<0.01; **, p<0.0001). A representative experiment is shown, repeated twice.

FIGS. 11A-I are a series of graphical representations of data showing Heat-MVA-induced antitumor effects is largely mediated by CD8$^+$ T cells and CD4$^+$ T cells contribute the development of systemic immunity against tumor re-challenge. FIG. 11A is a schematic diagram of intratumoral injection of Heat-MVA in the presence or absence of depleting antibodies for CD4$^+$, CD8$^+$, and NK cells in a unilateral B16-F10 melanoma implantation model. FIG. 11B is a Kaplan-Meier survival curve of mice treated with either PBS or Heat-MVA in the presence of isotype control, CD4+, CD8+, and NK cells-depleting antibodies (n=10; *, p<0.05; , p<0.01; **, p<0.0001). FIG. 11C-G are graphs of tumor volumes plotted against days after various treatment regimens including PBS (11C), Heat-MVA+isotype control (11D), Heat-MVA+anti-CD8 (11E), Heat-MVA+anti-CD4 (11F), and Heat-MVA+anti-NK (11G). FIG. 11H is a schematic diagram of tumor re-challenge with intradermal implantation of a lethal dose of 1×10⁶ B16-F10 cells at the left flank in naïve mice and survived mice treated with Heat-MVA for the original tumor implanted at the right flank in the presence or absence of CD4+ and NK cell depletion. FIG. 11I is a Kaplan-Meier survival curve of naïve mice (closed circles, n=6), Heat-MVA-treated mice (filled circles, n=10), Heat-MVA-treated mice with NK depletion (filled squares, n=6), and Heat-MVA-treated mice with CD4+ T cell depletion (filled triangles, n=6), re-challenged at the contralateral side with a lethal dose of B16-F10 melanoma cell re-challenge (*, p<0.05; , p<0.01; **, p<0.0001). A representative experiment is shown, repeated twice.

FIGS. 12A-B are a series of graphical representations of data showing intratumoral injection of Heat-MVA-induced anti-melanoma antibody response that is dependent on STING and Batf3. FIG. 12A is a scatterplot of anti-melanoma antibody concentrations (determined by ELISA) in the serum of STING$^{Gt/Gt}$, Batf3$^{-/-}$, and age-matched WT mice treated with Heat-MVA or PBS (NT, no serum treatment control). FIG. 12B is a scatterplot of anti-vaccinia viral antibody concentrations (determined by ELISA) in the serum of STING$^{Gt/Gt}$, Batf3$^{-/-}$, and age-matched WT mice treated with Heat-MVA or PBS (NT, no serum treatment control). A representative experiment is shown, repeated twice.

FIGS. 13A-D are graphs of tumor volume plotted against time (days) after various treatment regimens including intratumoral injection of PBS plus intraperitoneal delivery of isotype antibody control (13A, n=5), intratumoral injection of PBS plus intraperitoneal delivery of anti-CTLA-4 antibody (13B, n=5), intratumoral injection of Heat-MVA plus isotype control (13C, n=10), and intratumoral injection of Heat-MVA plus intraperitoneal delivery of anti-CTLA-4 (13D, n=9). FIG. 13E is a scatterplot of tumor volumes at the start of virus injection in mice treated with PBS+isotype, Heat-MVA+Isotype, PBS+anti-CTLA-4, and Heat-MVA+anti-CTLA4 antibody. FIG. 13F is a Kaplan-Meier survival curve of tumor-bearing mice treated with PBS+Isotype, Heat-MVA+Isotype, PBS+anti-CTLA-4, and Heat-MVA+anti-CTLA4 antibody (*, p<0.05; , p<0.01; **, p<0.0001). A representative experiment is shown, repeated twice.

FIG. 14A is a scheme of treatment plan in which B16-F10 melanomas were treated with either MVA or Heat-MVA intratumorally in a bilateral intradermal tumor implantation model. FIG. 14B is a graph of replication curves of MVA in B16-F10 cells when the MOI was either 5 (open circles) or 0.05 (filled circles). FIG. 14C is a Kaplan-Meier survival curve of tumor-bearing mice treated either PBS (open circles, n=7), MVA (filled squares, n=9), or Heat-MVA (filled circles, n=9) (, p<0.01; *, p<0.001). FIG. 14D-E are graphs of injected (D) and non-injected (E) tumor volume plotted against time (days) after PBS injection.

FIG. 15A is a graph of absolute numbers of tumor infiltrating CD45+, CD103+CD11c+, CD3+ and CD8+ per gram of non-injected tumors after intratumoral injection of PBS, MVA or Heat-MVA to the contralateral tumors. FIG. 15B is a graph of absolute numbers of tumor infiltrating Granzyme B+CD8+, Ki67+CD8+, Granzyme B+CD4+, and Ki67+CD4+ cells per gram of non-injected tumors after intratumoral injection of PBS (n=5), MVA (n=5) or Heat-MVA (n=5) to the contralateral tumors. Data are means±SEM (n=5). A representative experiment is shown, repeated twice.

FIGS. 16A-I are a series of graphical representations of data showing that Heat-MVA is less effective in eradicating B16-F10 melanomas in STING-deficient mice or Batf3-deficient mice compared with wild-type controls in a bilateral tumor implantation model. FIG. 16A-B are graphs of injected (A) and non-injected (B) tumor volume plotted against time (days) after PBS injection (n=6). FIG. 16C-D are graphs of injected (C) and non-injected (D) tumor volume plotted against time (days) after Heat-MVA injection in WT mice (n=10). FIG. 16E-F are graphs of injected (E) and non-injected (F) tumor volume over days after Heat-MVA injection in STING$^{Gt/Gt}$ mice (n=8). FIG. 16G-H are graphs of injected (G) and non-injected (H) tumor volume over days after Heat-MVA injection in Batf3$^{-/-}$ mice (n=6). FIG. 16I is a Kaplan-Meier survival curve of tumor-bearing WT, STING$^{Gt/Gt}$, and Batf3$^{-/-}$ mice treated with PBS or Heat-MVA (, p<0.01; **, p<0.0001). A representative experiment is shown, repeated once.

FIGS. 17A-D are a series of graphical representations of data showing that intratumoral injection of Heat-MVA is more effective in WT mice than in Batf3−/− mice in recruiting and activating immune cells in the injected and non-injected tumors in a bilateral B16-F10 melanoma model. Tumor-bearing mice were treated with intratumoral injections of PBS or Heat-MVA as described for FIG. 14A. The non-injected tumors were harvested at day 7 post first treatment after a total of two treatments. Tumor infiltrating immune cells were analyzed by FACS. FIG. 17A-B are graphs of absolute numbers of tumor infiltrating CD3+ and CD8+ per gram of injected (A) and non-injected (B) tumors after intratumoral injection of PBS or Heat-MVA to the right flank tumors on WT and Batf3$^{-/-}$ mice. FIG. 17C-D are graphs of absolute numbers of tumor infiltrating Ki67+CD8+ and Ki67+CD4+ cells per gram of injected (C) and non-injected (D) tumors after intratumoral injection of PBS or Heat-MVA to the right flank tumors on WT and Batf3$^{-/-}$ mice (, p<0.01; *,p<0.001; ****, p<0.0001). Data are means±SEM (n=4). A representative experiment is shown, repeated twice.

FIGS. 18A-L are a series of graphical representations of data showing that the combination of intratumoral injection of Heat-MVA with systemic delivery of anti-CTLA-4, anti- PD-1, or anti-PD-L1 antibodies significantly increases the overall response and cure rates in tumor-bearing animals. FIG. 18A is a scheme of treatment plan in which B16-F10 melanomas were treated with either intratumoral delivery of PBS or Heat-MVA with or without systemic delivery of immune checkpoint blockade antibodies in a bilateral intradermal tumor implantation model. FIG. 18B is a Kaplan-Meier survival curve of tumor-bearing mice treated with PBS (n=5), Heat-MVA+isotype control (n=10), Heat-MVA+anti-CTLA4 antibody (n=10), Heat-MVA+anti-PD1 antibody (n=10), or Heat-MVA+anti-PD-L1 antibody (n=10; *, p<0.05; , p<0.01; **, p<0.0001). FIG. 18C-D are graphs of injected (C) and non-injected (D) tumor volumes over days after PBS injection. FIG. 18E-F are graphs of injected (E) and non-injected (F) tumor volumes over days after intratumoral injection of Heat-MVA and intraperitoneal delivery of isotype control. FIG. 18G-H are graphs of injected (G) and non-injected (H) tumor volumes over days after intratumoral injection of Heat-MVA and intraperitoneal delivery of anti-CTLA-4 antibody. FIG. 18I-J are graphs of injected (I) and non-injected (J) tumor volumes over days after intratumoral injection of Heat-MVA and intraperitoneal delivery of anti-PD-1 antibody. FIG. 18K-L are graphs of injected (K) and non-injected (L) tumor volumes over days after intratumoral injection of Heat-MVA and intraperitoneal delivery of anti-PD-L1 antibody. A representative experiment is shown, repeated twice.

FIG. 19A-B are graphs of the concentrations of secreted IFN-α (A) and IFN-β (B) in the medium over time following MVA (filled circles), Heat-MVA (open squares), or UV-MVA (filled squares) infection of cDCs (***, p<0.001). Data are means±SEM (n=3). A representative experiment is shown, repeated twice. FIG. 19C-D are bar graphs of the concentrations of secreted IFN-α (C) and IFN-β (D) in the medium of cDCs generated from $STING^{Gt/Gt}$, $IRF3^{-/-}$, and WT control mice and infected with UV-MVA. Data are means±SEM (n=3). A representative experiment is shown, repeated twice. FIG. 19E is a scanned image of a Western Blot showing protein levels of p-IRF3, IRF3, STING, and β-actin in $STING^{+/+}$ and $STING^{Gt/Gt}$ cDCs following UV-MVA infection (hpi, hours post infection; NT, no treatment).

FIGS. 20A-H are a series of graphical representations of data showing that UV-inactivated MVA (UV-MVA) induces inflammatory cytokines and chemokines from MC38 colon adenocarcinoma cell line, and intratumoral injection of UV-MVA leads to tumor eradication and the development of systemic antitumor immunity with similar efficacies as Heat-MVA. FIG. 20A-C are bar graphs of the concentrations of secreted IL-6 (A), CCL4 (B), and CCL5 (C) in the medium of MC38 cells infected with MVA, Heat-MVA, UV-MVA, or mock control. Data are means±SEM (n=3). A representative experiment is shown, repeated twice. FIG. 20D-F are graphs of tumor volumes v. time (days) after intratumoral injection of PBS (D), Heat-MVA (E), or UV-MVA (F). FIG. 20G is a Kaplan-Meier survival curve of tumor-bearing mice injected with PBS (filled circles, n=5), or Heat-MVA (filled squares, n=10), or UV-MVA (filled triangles, n=7). FIG. 20H is a Kaplan-Meier survival curve of naïve mice (closed circles, n=5), Heat-MVA-treated mice (filled squares, n=7), and UV-MVA-treated mice (filled triangles, n=5) re-challenged at the contralateral side with a lethal dose of MC38 colon adenocarcinoma cells. A representative experiment is shown, repeated once.

FIGS. 21A-N are a series of graphical representations of data showing that the combination of intratumoral injection of Heat-MVA with systemic delivery of anti-CTLA-4 or anti-PD-L1 antibodies significantly increases the overall response and cure rates in tumor-bearing animals. FIG. 21A-B are graphs of injected (A) and non-injected (B) tumor volume plotted against time (days) after PBS injection. FIG. 21C-D are graphs of injected (C) and non-injected (D) tumor volume plotted against time (days) after intratumoral injection of PBS and intraperitoneal delivery of anti-CTLA-4 antibody. FIG. 21E-F are graphs of injected (E) and non-injected (F) tumor volume plotted against time (days) after intratumoral injection of PBS and intraperitoneal delivery of anti-anti-PD-L1 antibody. FIG. 21G-H are graphs of injected (G) and non-injected (H) tumor volume plotted against time (days) after intratumoral injection of Heat-MVA and intraperitoneal delivery of isotype antibody control. FIG. 21I-J are graphs of injected (I) and non-injected (J) tumor volume plotted against time (days) after intratumoral injection of Heat-MVA and intraperitoneal delivery of anti-CTLA-4 antibody. FIG. 21K-L are graphs of injected (K) and non-injected (L) tumor volume plotted against time (days) after intratumoral injection of Heat-MVA and intraperitoneal delivery of anti-PD-L1 antibody. FIG. 21M is a Kaplan-Meier survival curve of tumor-bearing mice treated with PBS (n=6), anti-CTLA4 antibody (n=7), or anti-PD-L1 antibody (n=7; ***, p<0.001). FIG. 21N is a Kaplan-Meier survival curve of tumor-bearing mice treated with PBS (n=6), Heat-MVA+isotype control (n=10), Heat-MVA+anti-CTLA4 antibody (n=10), or Heat-MVA+anti-PD-L1 antibody (n=10; *, p<0.05; , p<0.01; **, p<0.0001). A representative experiment is shown, repeated once.

FIGS. 22A-H are a series of graphical representations of data showing that the co-administration of Heat-MVA and anti-CTLA-4 intratumorally significantly increases the overall response and cure rates in a bilateral B16-F10 tumor implantation model. FIG. 22A-B are graphs of injected (A) and non-injected (B) tumor volume plotted against time (days) after PBS injection (n=10). FIG. 22C-D are graphs of injected (C) and non-injected (D) tumor volume plotted against time (days) after intratumoral injection of Heat-MVA and isotype control antibody (n=10). FIG. 21E-F are graphs of injected (E) and non-injected (F) tumor volume plotted against time (days) after intratumoral co-administration of Heat-MVA and anti-CTLA-4 antibody at one tenth of the dose used for intraperitoneal delivery (n=10). FIG. 22G-H are graphs of injected (G) and non-injected (H) tumor volume plotted against time (days) after intratumoral injection of Heat-MVA and intraperitoneal delivery of anti-CTLA-4 antibody (n=10).

DETAILED DESCRIPTION

Figure 1A:
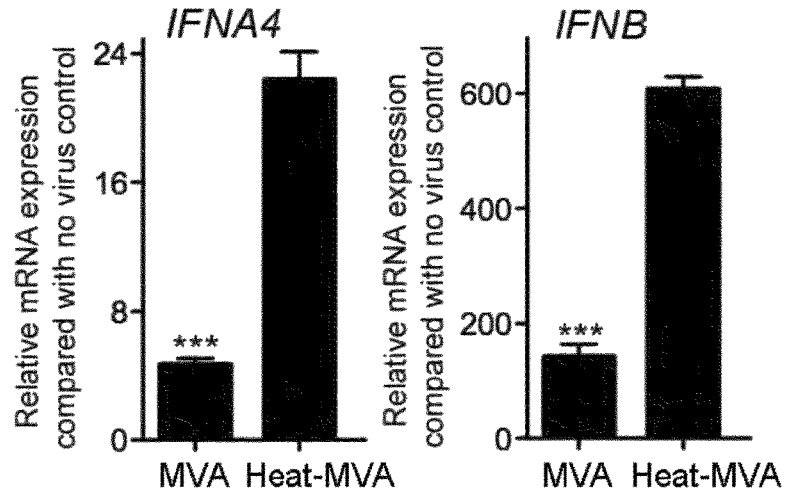
FIGS. 1A-1C are a series of graphical representations of data showing that Heat-MVA induces higher levels of type I IFN production in murine cDCs than MVA.

Definitions:

As used herein the following terms shall have the meanings ascribed to them below unless the context clearly indicates otherwise:

"Cancer" refers to a class of diseases of humans and animals characterized by uncontrolled cellular growth. Unless otherwise explicitly indicated, the term "cancer" may be used herein interchangeably with the terms "tumor," (which in turn includes both primary and metastatic tumors) "malignancy," "hyperproliferation" and "neoplasm(s);" the term "cancer cell(s)" is interchangeable with the terms "tumor cell(s)," "malignant cell(s)," "hyperproliferative cell(s)," and "neoplastic cell(s)".

"Melanoma" refers to a malignant neoplasm originating from cells that are capable of producing melanin. The term melanoma is synonymous with "malignant melanoma". Melanoma metastasizes widely, involving a patient's lymph nodes, skin, liver, lungs and brain tissues.

"Solid tumor" refers to all neoplastic cell growth and proliferation, primary or metastatic, and all pre-cancerous and cancerous cells and tissues, except for hematologic cancers such as lymphomas, leukemias and multiple myeloma. Examples of solid tumors include, but are not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Some of the most common solid tumors for which the compositions and methods of the present disclosure would be useful include: head-and-neck cancer, rectal adenocarcinoma, glioma, medulloblastoma, urothelial carcinoma, pancreatic adenocarcinoma, endometrial cancer, ovarian cancer, prostate adenocarcinoma, non-small cell lung cancer (squamous and adenocarcinoma), small cell lung cancer, melanoma, breast carcinoma, renal cell carcinoma, and hepatocellular carcinoma.

"Metastasis" refers to the spread of cancer from its primary site to neighboring tissues or distal locations in the body. Cancer cells can break away from a primary tumor, penetrate into lymphatic and blood vessels, circulate through the bloodstream, and grow in in normal tissues elsewhere in the body. Metastasis is a sequential process, contingent on tumor cells (or cancer stem cells) breaking off from the primary tumor, traveling through the bloodstream or lymphatics, and stopping at a distant site. Once at another site, cancer cells re-penetrate through the blood vessels or lymphatic walls, continue to multiply, and eventually form a new tumor (metastatic tumor). In some embodiments, this new tumor is referred to as a metastatic (or secondary) tumor.

"Immune response" refers to the action of one or more of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, etc. An immune response may include a cellular response, such as a T cell response that is an alteration (modulation, e.g., significant enhancement, stimulation, activation, impairment, or inhibition) of cellular function, i.e., a T cell function. A T cell response may include generation, proliferation or expansion, or stimulation of a particular type of T cell, or subset of T cells, for example, effector $CD4^+$, cytotoxic $CD8^+$, or natural killer (NK) cells. Such T cell subsets may be identified by detecting one or more cell receptors or cell surface molecules (e.g., CD or cluster of differentiation molecules). A T cell response may also include altered expression (statistically significant increase or decrease) of a cellular factor, such as a soluble mediator (e.g., a cytokine, lymphokine, cytokine binding protein, or interleukin) that influences the differentiation or proliferation of other cells. For example, Type I interferon (IFN-$\alpha/\beta$) is a critical regulator of the innate immunity [71]. Animal and human studies have shown a role for IFN-$\alpha/\beta$ in directly influencing the fate of both $CD4^+$ and $CD8^+$T cells during the initial phases of antigen recognition anti-tumor immune response. Type I IFN is induced in response to activation of dendritic cells, in turn a sentinel of the innate immune system.

"Tumor immunity" refers to the process by which tumors evade recognition and clearance by the immune system. Thus, as a therapeutic concept, tumor immunity is "treated" when such evasion is attenuated or eliminated, and the tumors are recognized and attacked by the immune system. An example of tumor recognition is tumor binding, and examples of tumor attack are tumor reduction (in number, size or both) and tumor clearance.

"T cell" refers to a thymus derived lymphocyte that participates in a variety of cell-mediated adaptive immune reactions.

"Helper T cell" refers to a $CD4^+$ T cell; helper T cells recognize antigen bound to MHC Class II molecules. There are at least two types of helper T cells, Th1 and Th2, which produce different cytokines.

"Cytotoxic T cell" refers to a T cell that usually bears CD8 molecular markers on its surface (CD8+) and that functions in cell-mediated immunity by destroying a target cell having a specific antigenic molecule on its surface. Cytotoxic T cells also release Granzyme, a serine protease that can enter target cells via the perforin-formed pore and induce apoptosis (cell death). Granzyme serves as a marker of Cytotoxic phenotype. Other names for cytotoxic T cell include CTL, cytolytic T cell, cytolytic T lymphocyte, killer T cell, or killer T lymphocyte. Targets of cytotoxic T cells may include virus-infected cells, cells infected with bacterial or protozoal parasites, or cancer cells. Most cytotoxic T cells have the protein CD8 present on their cell surfaces. CD8 is attracted to portions of the Class I MHC molecule. Typically, a cytotoxic T cell is a CD8+ cell.

"Tumor-infiltrating lymphocytes" refers to white blood cells of a subject afflicted with a cancer (such as melanoma), that are resident in or otherwise have left the circulation (blood or lymphatic fluid) and have migrated into a tumor.

"Immune checkpoint inhibitor(s)" or "immune checkpoint blocking agent" refers to molecules that completely or partially reduce, inhibit, interfere with or modulate the activity of one or more checkpoint proteins. Checkpoint proteins regulate T-cell activation or function. Checkpoint proteins include, but are not limited to CTLA-4 and its ligands CD80 and CD86; PD-1 and its ligands PDL1 and PDL2; LAG3, B7-H3, B7-H4, TIM3, ICOS, and BTLA [72].

"Parenteral" when used in the context of administration of a therapeutic substance includes any route of administration other than administration through the alimentary tract. Particularly relevant for the methods disclosed herein are intravenous (including for example through the hepatic portal vein), intratumoral or intrathecal administration.

"Antibody" refers to an immunoglobulin molecule which specifically binds to an antigen or to an antigen-binding fragment of such a molecule. Thus, antibodies can be intact immunoglobulins derived from natural sources or from recombinant sources and can be immunoreactive (antigen-binding) fragments or portions of intact immunoglobulins. The antibodies may exist in a variety of forms including, for example, polyclonal antibodies, monoclonal antibodies, Fv, Fab and F(ab)2, as well as single chain antibodies (scFv) humanized antibodies, chimeric antibodies, human recombinant antibodies and bi- and tri-specific antibodies.

"Oncolytic virus" refers to a virus that preferentially infects cancer cells, replicates in such cells, and induces lysis of the cancer cells through its replication process. Nonlimiting examples of naturally occurring oncolytic viruses include vesicular stomatitis virus, reovirus, as well as viruses engineered to be oncoselective such as adenovirus, Newcastle disease virus and herpes simplex virus [19, 73-75]. Vaccinia virus infects many types of cells but replicates preferentially in tumor cells due to the fact that tumor cells have a metabolism that favors replication, exhibit activation of certain pathways that also favor replication and create an environment that evades the innate immune system, which also favors viral replication. Heat-inactivated MVA does not fit the definition of oncolytic virus.

"MVA" means "modified vaccinia Ankara" and refers to a highly attenuated strain of vaccinia derived from the Ankara strain and developed for use as a vaccine and vaccine adjuvant. The original MVA was isolated from the wild-type Ankara strain by successive passage through chicken embryonic cells. Treated thus, it lost about 15% of the genome of wild-type vaccinia including its ability to replicate efficiently in primate (including human) cells [76]. The smallpox vaccination strain MVA: marker, genetic structure, experience gained with the parenteral vaccination and behavior in organisms with a debilitated defense mechanism. MVA is considered an appropriate candidate for development as a recombinant vector for gene or vaccination delivery against infectious diseases or tumors [77]. MVA has a genome of 178 kb in length and a sequence first disclosed in Antoine, G et al [78]. Sequences are also disclosed in Genbank U94848.1. Clinical grade MVA is commercially and publicly available from Bavarian Nordic A/S Kvistgaard, Denmark. Additionally, MVA is available from ATCC, Rockville, Md. and from CMCN (Institut Pasteur Collection Nationale des Microorganismes) Paris, France. Mutant MVA E3L knockout ($\Delta$E3L-MVA) and its preparation have been described for example in U.S. Pat. No. 7,049,145.

"Heat-inactivated MVA" or "heat MVA" means MVA which has been further treated by exposure to heat under conditions that do not destroy its immunogenicity or its ability to enter target cells (tumor cells) but remove residual replication ability of the virus as well as factors that inhibit the host's immune response (for example, such factors as inhibit the induction of IFN Type I in infected cells). An example of such conditions is exposure to a temperature within the range of about 50 to about 60° C. for a period of time of about an hour. Other times and temperatures can be determined with routine experimentation and IFN Type I induction in infected cDC's can be compared to the Heat-MVA used in experiments described herein and should be higher than that of MVA. In one experiment conducted by the present inventors, infection of cDCs by MVA treated with a combination of 65° C. and 1-hour exposure failed to induce IFN Type I. This combination of safety and strong immunogenicity makes Heat-MVA particularly attractive compared to WT vaccinia and even MVA.

"UV-inactivated MVA" or "UV-MVA" means MVA that has been inactivated by exposure to UV under conditions that do not destroy its immunogenicity or its ability to enter target cells (tumor cells) but remove residual replication ability of the virus. An example of such conditions, which can be useful in the present methods, is exposure to UV using for example a 365 nm UV bulb for a period of about 30 min to about 1 hour [56, 79]. Again, as explained for Heat-MVA above, the limits of these conditions of UV wavelength and exposure can be determined by routine experimentation by determining Type I IFN induced by UV-MVA having received a given exposure and comparing it to the Type I IFN induced by UV-MVA used in the experiments below and to untreated MVA. UV-MVA is similarly safe to Heat-MVA and also induces significant Type I IFN.

Accordingly, "inactivated MVA" shall be used as a generic term comprising heat-inactivated MVA and UV-inactivated MVA which are infective, nonreplicative and do not suppress IFN Type I production in infected DC cells. MVA inactivated by a combination of heat and UV radiation is also within the scope of the present disclosure.

"Subject" means any animal (mammalian, human or other) patient that can be afflicted with cancer.

"Therapeutically effective amount" or "effective amount" refers to a sufficient amount of an agent when administered at one or more dosages and for a period of time sufficient to provide a desired biological result in alleviating, curing or palliating a disease. In the present disclosure, an effective amount of the inactivated-MVA is an amount that (administered for a suitable period of time and at a suitable frequency) reduces the number of cancer cells; or reduces the tumor size or eradicates the tumor; or inhibits (i.e., slows down or stops) cancer cell infiltration into peripheral organs; inhibits (i.e., slows down or stops) metastatic growth; inhibits (i.e., stabilizes or arrests) tumor growth; allows for treatment of the tumor, and/or induces an immune response against the tumor. An appropriate therapeutic amount in any individual case may be determined by one of ordinary skill in the art using routine experimentation in light of the present disclosure. Such determination will begin with amounts found effective in vitro and amounts found effective in animals. The therapeutically effective amount will be initially determined based on the concentration or concentrations found to confer a benefit to cells in culture. Effective amounts can be extrapolated from data within the cell culture and can be adjusted up or down based on factors such as detailed herein. An example of an effective amount range is from $10^5$ viral particles to about $10^{12}$ viral particles per administration.

With particular reference to the viral-based immunostimulatory agents disclosed herein, "therapeutically effective amount" or "effective amount" refers to an amount of a composition comprising inactivated MVA sufficient to reduce, inhibit, or abrogate tumor cell growth, thereby reducing or eliminating the tumor, or sufficient to inhibit, reduce or abrogate metastatic spread either in vitro or in a subject or to elicit an immune response against the tumor that will eventually result in one or more of reduction, inhibition and/or abrogation as the case may be. The reduction, inhibition, or eradication of tumor cell growth may be the result of necrosis, apoptosis, or an immune response or a combination of two or more of the foregoing. The amount that is therapeutically effective may vary depending on such factors as the particular inactivated MVA used in the composition, the age and condition of the subject being treated, the extent of tumor formation, the presence or absence of other therapeutic modalities, and the like. Similarly, the dosage of the composition to be administered and the frequency of its administration will depend on a variety of factors, such as the potency of the active ingredient, the duration of its activity once administered, the route of administration, the size, age, sex and physical condition of the subject, the risk of adverse reactions and the judgment of the medical practitioner. The compositions are administered in a variety of dosage forms, such injectable solutions.

With particular reference to combination therapy with an immune checkpoint inhibitor, "therapeutically effective amount" for an immune checkpoint blocking agent" shall mean an amount of an immune checkpoint blocking agent sufficient to block an immune checkpoint from averting apoptosis response in tumor cells of the subject being treated. There are several immune checkpoint blocking agents approved, in clinical trials or still otherwise under development including CD28 inhibitors such as CTL4 inhibitors (e.g., ipilimumab), PD-1 inhibitors (e.g., nivolumab, pembrolizumab, pidilizumab, lambrolizumab) PD-L1 inhibitors (MPDL3280A, BMS-936559, MEDI4736, MSB 00107180) ICOS and BTLA or decoy molecules of them. Dosage ranges of the foregoing are known in or readily within the skill in the art as several dosing clinical trials have been completed, making extrapolation to other agents possible.

Preferably, the tumor expresses the particular checkpoint but this is not strictly necessary as immune checkpoint blocking agents block more generally immune suppressive mechanisms within the tumors, elicited by tumor cells, stromal cell, and tumor infiltrating immune cells.

For example, the CTLA4 inhibitor ipilimumab, when administered as adjuvant therapy after surgery in melanoma is administered at 1-2 mg/mL over 90 minutes for a total infusion amount of 3 mg/kg every three weeks for a total of 4 doses. This therapy is often accompanied by severe even life-threatening immune-mediated adverse reactions, which limits the tolerated dose as well as the cumulative amount that can be administered. It is anticipated that it will be possible to reduce the dose and/or cumulative amount of ipilimumab when it is administered conjointly with inactivated MVA. In particular, in light of the experimental results set forth below, it is anticipated that it will be further possible to reduce the CTLA4 inhibitor's dose if it is administered directly to the tumor simultaneously or sequentially with inactivated MVA. Accordingly, the amounts provided above for ipilimumab will be a starting point for determining the particular dosage and cumulative amount to be given to a patient in conjoint administration but dosing studies will be required to determine optimum amounts.

Pembrolizumab is prescribed for administration as adjuvant therapy in melanoma diluted to 25 mg/mL is administered at a dosage of 2 mg/kg over 30 minutes every three weeks.

Nivolumab is prescribed for administration at 3 mg/kg as an intravenous infusion over 60 minutes every two weeks.

"Pharmaceutically acceptable excipient" includes pharmaceutically acceptable carriers or diluents, such as any and all solvents, dispersion media, coatings, isotonic and absorption delaying agents and the like. It also includes preservatives and antibacterial and antifungal agents. The use of such media and agents for biologically active substances is well known in the art. Further details of excipients are provided below.

"Delivering" used in connection with depositing the inactivated-MVA of the present disclosure in the tumor microenvironment whether this is done by local administration to the tumor or by systemic administration, for example intravenous route. The term focuses on inactivated-MVA that reaches the tumor itself.

"Conjoint administration" herein refers to administration of a second therapeutic modality in combination with inactivated MVA for example an immune checkpoint blocking agent administered and in close temporal proximity with the inactivated MVA. For example, a PD-1/PDL-1 inhibitor and/or a CTLA4 inhibitor (in more specific embodiments, an antibody) can be administered simultaneously with the heat-inactivated MVA (by intravenous or intratumoral injection when the inactivated-MVA is administered intratumorally or systemically as stated above) or before or after the inactivated-MVA administration. If the inactivated MVA administration and the immune checkpoint blocking agent are administered 1-7 days apart or even up to three weeks apart, this would be within "close temporal proximity" as stated herein.

In one embodiment, the present disclosure relates to a method for eliciting an antitumor immune response in subjects with tumors comprising delivering to the tumor an amount of inactivated MVA effective to bring about one or more of the following:

increase cytotoxic CD8+ T cells within the tumor and/or in tumor-draining lymph nodes;

induce maturation of dendritic cells infiltrating said tumor through induction of type I IFN;

induce effector T cells in the subject recognizing tumor cells within the tumor and/or in tumor draining lymph nodes;

reduce immune suppressive (regulatory) CD4+ T cells within the tumor; and induce cells of the tumor to express MHC Class I on their surface and to produce one or more of Type I IFN or other inflammatory cytokines or chemokines.

The present inventors have explored the mechanism of the immune response and concluded that it is initiated by the cytosolic DNA-sensing pathway mediated by cGAS/STING which mediates production of Type 1 IFN. Further insights into the mechanism and the immune cells that are recruited are provided in the Examples. The conclusions presented therein are not confined to the specific experimental milieu where these mechanisms are being elucidated.

In one embodiment, the present disclosure provides a method of treating a subject diagnosed with a solid tumor comprising delivering to the tumor a therapeutic effective amount of the Heat-MVA described herein.

In one embodiment, the present disclosure provides a method for inducing anti-tumor immunity in a subject diagnosed with cancer comprising administering to the subject a therapeutically effective amount of inactivated MVA. The methods of the present disclosure include induction of anti-tumor immunity that can reduce the size of the tumor, eradicate the tumor, inhibit growth of the tumor, or inhibit metastasis or metastatic growth of the tumor.

In another embodiment, the present disclosure provides a method for enhancing, stimulating, or eliciting, in a subject diagnosed with a solid malignant tumor, an anti-tumor immune response that may include an innate immune response and/or an adaptive immune response such as a T cell response by exposing the tumor to inactivated MVA in a therapeutically effective amount.

In specific embodiments, the present disclosure provides methods of eliciting an immune response that mediates adaptive immune responses both in terms of T-cell cytotoxicity directed against tumor cells and in terms of eliciting T helper cells also directed against tumor cells. The methods comprise administering to a subject intratumorally or intravenously a composition comprising a nonreplicative heat- or UV-inactivated MVA wherein administration of said composition results in a tumor-specific immune response against the tumor and, eventually, in reduction, inhibition or abrogation of tumor growth and/or in inhibition of metastatic growth. Indeed, the present inventors have shown that cancer cells are being killed and that the immune response can migrate to remote locations, as would be the case with metastases.

In some embodiments, the present disclosure provides methods of eliciting an immune response that mediates adaptive immune responses both in terms of T-cell cytotoxicity directed against tumor cells and in terms of eliciting T helper cells also directed against tumor cells. The methods comprise administering to a subject parenterally a composition comprising an inactivated-MVA wherein administration of said composition results in a tumor-specific immune response against the tumor and, eventually, in reduction, inhibition or eradication of tumor growth and/or in inhibition of metastatic growth. Indeed, the present inventors have shown that cancer cells are being killed and that the immune response can migrate to remote locations, as would be the case with metastases.

Because inactivated MVA is not replication competent, it does not exert its effect on the immune system the same way as replication competent vaccines or vectors. Thus, while it is believed that stimulation of the immune system is a barrier to efficacy for oncolysis [19], inactivated MVA is able to harness the innate immune system to stimulate adaptive immunity, both in terms of cytotoxicity and more broadly of T effector cell activation against the tumor.

The present disclosure thus provides a method for treating a solid malignant tumor, delivering to a tumor of the subject an amount of inactivated-MVA effective to bring an increase of cytotoxic CD8+ cells and reduction of regulatory CD4+ cells in the tumor and inducing an immune response in a subject diagnosed with solid tumor.

The present disclosure also provides a method for generating antitumor systemic immunity by treating a solid malignant tumor, comprising delivering to a tumor of the subject an amount of inactivated-MVA effective to bring about a considerable even dramatic increase in immune cells in the non-injected tumors, including CD103$^+$ DCs, cytotoxic CD8$^+$ cells and CD4$^+$ effector cells, and thereby causing one or both of rejection of non-injected tumors in said subject and resistance to tumor metastasis (which the present inventors test by tumor rechallenge).

Modified Vaccinia Ankara (MVA)

Modified Vaccinia Ankara (MVA) virus is a member of the genera Orthopoxvirus in the family of Poxviridae. MVA was generated by approximately 570 serial passages on chicken embryo fibroblasts (CEF) of the Ankara strain of vaccinia virus (CVA) [80]. As a consequence of these long-term passages, the resulting MVA virus contains extensive genome deletions and is highly host cell restricted to avian cells [30]. It was shown in a variety of animal models that the resulting MVA is significantly avirulent [76].

The safety and immunogenicity of MVA has been extensively tested and documented in clinical trials, particularly against the human smallpox disease. These studies included over 120,000 individuals and have demonstrated excellent efficacy and safety in humans. Moreover, compared to other vaccinia based vaccines, MVA has weakened virulence (infectiousness) while it triggers a good specific immune response. Thus, MVA has been established as a safe vaccine vector, with the ability to induce a specific immune response.

Due to above mentioned characteristics, MVA became an attractive target for to the development of engineered MVA vectors, used for recombinant gene expression and vaccines. As a vaccine vector, MVA has been investigated against numerous pathological conditions, including HIV, tuberculosis and malaria, as well as cancer [33, 34].

It has been demonstrated that MVA infection of human monocyte-derived dendritic cells (DC) causes DC activation, characterized by the upregulation of co-stimulatory molecules and secretion of proinflammatory cytokines [56]. In this respect, MVA differs from standard wild type Vaccinia virus (WT-VAC), which fails to activate DCs. Dendritic cells can be classified into two main subtypes: conventional dendritic cells (cDCs) and plasmacytoid dendritic cells (pDCs). The former, especially the CD8+ subtype, are particularly adapted to presenting antigens to T cells; the latter are strong producers of Type I IFN.

Viral infection of human cells results in activation of an innate immune response (the first line of defense) mediated by type I interferons, notably interferon-alpha ($\alpha$). This normally leads to activation of an immunological "cascade," with recruitment and proliferation of activated T cells (both CTL and helper) and eventually with antibody production. However, viruses express factors that dampen immune responses of the host. MVA is a better immunogen than WT-VAC and replicates poorly in mammalian cells [81].

However, it is not entirely nonreplicative and, as the present inventors show, contains some immunosuppressive activity.

Immune Response

In addition to induction of the immune response by up-regulation of particular immune system activities (such as antibody and/or cytokine production, or activation of cell mediated immunity), immune responses may also include suppression, attenuation, or any other down-regulation of detectable immunity, so as to reestablish homeostasis and prevent excessive damage to the host's own organs and tissues. In some embodiments, an immune response that is induced according to the methods of the present disclosure generates cytotoxic CD8$^+$ T cells or activated T helper cells or both that can bring about directly or indirectly the death, or loss of the ability to propagate, of a tumor cell.

Induction of an immune response by the methods of the present disclosure may be determined by detecting any of a variety of well-known immunological parameters [82, 83]. Induction of an immune response may therefore be established by any of a number of well-known assays, including immunological assays, Such assays include, but need not be limited to, in vivo, ex vivo, or in vitro determination of soluble immunoglobulins or antibodies; soluble mediators such as cytokines, chemokines, hormones, growth factors and the like as well as other soluble small peptides, carbohydrate, nucleotide and/or lipid mediators; cellular activation state changes as determined by altered functional or structural properties of cells of the immune system, for example cell proliferation, altered motility, altered intracellular cation gradient or concentration (such as calcium); phosphorylation or dephosphorylation of cellular polypeptides; induction of specialized activities such as specific gene expression or cytolytic behavior; cellular differentiation by cells of the immune system, including altered surface antigen expression profiles, or the onset of apoptosis (programmed cell death); or any other criterion by which the presence of an immune response may be detected. For example, cell surface markers that distinguish immune cell types may be detected by specific antibodies that bind to CD4+, CD8+, or NK cells. Other markers and cellular components that can be detected include but are not limited to interferon $\gamma$ (IFN-$\gamma$), tumor necrosis factor (TNF), IFN-$\alpha$, IFN-β, IL-6, and CCL5. Common methods for detecting the immune response include, but are not limited to flow cytometry, ELISA, immunohistochemistry. Procedures for performing these and similar assays are widely known and may be found, for example in Letkovits (Immunology Methods Manual: The Comprehensive Sourcebook of Techniques, Current Protocols in Immunology, 1998).

Pharmaceutical Compositions and Preparations

Pharmaceutical compositions comprising inactivated-MVA may contain one or more pharmaceutically acceptable excipients, such as a carrier or diluent. These are ingredients which do not interfere with activity or effectiveness of the vaccine components of the present disclosure and that are not toxic A carrier or diluent can be a solvent or dispersion medium containing, for example, water, dextrose solution, polyol (for example, glycerol, propylene glycol, and liquid polyethylene glycol, and the like), serum albumin, Ringer's solution, suitable mixtures thereof, and vegetable oils. The proper fluidity can be maintained, for example, by the use of a coating such as lecithin, by the maintenance of the required particle size in the case of dispersion and by the use of surfactants and/or wetting agents such as sodium lauryl sulfate or ethanol. The prevention of the action of microorganisms can be effected by various preservatives, antibacterial and antifungal agents, for example, parabens, chlorobutanol, phenol, sorbic acid, thimerosal, benzalcomium chloride, benzethonium chloride and the like. In many cases, it will be preferable to include isotonic agents, for example, sugars like mannitol sorbitol, lactose or sodium or potassium chloride. Prolonged absorption of the injectable compositions can be brought about by the use in the compositions of agents delaying absorption, for example, aluminum monostearate and gelatin.

Pharmaceutical compositions and preparations comprising inactivated-MVA may be manufactured by means of conventional mixing, dissolving, emulsifying, or lyophilizing processes. Pharmaceutical viral compositions may be formulated in conventional manner using one or more physiologically acceptable carriers, diluents, excipients or auxiliaries that facilitate formulating virus preparations suitable for in vitro, in vivo, or ex vivo use. The compositions can be combined with one or more additional biologically active agents (for example parallel administration of GM-CSF) and may be formulated with a pharmaceutically acceptable carrier, diluent or excipient to generate pharmaceutical (including biologic) or veterinary compositions of the instant disclosure suitable for parenteral or intra-tumoral administration.

Many types of formulation are possible and well-known. The particular type chosen is dependent upon the route of administration chosen, as is well-recognized in the art. For example, systemic formulations will generally be designed for administration by injection, e.g., intravenous, as well as those designed for intratumoral administration Preferably, the systemic or intratumoral formulation is sterile.

Sterile injectable solutions are prepared by incorporating inactivated-MVA in the required amount of the appropriate solvent with various other ingredients enumerated herein, as required, followed by suitable sterilization means. Generally, dispersions are prepared by incorporating the active ingredients into a sterile vehicle that contains the basic dispersion medium and the required other ingredients from those enumerated above. In the case of sterile powders for the preparation of sterile injectable solutions, the preferred methods of preparation are vacuum drying and freeze-drying techniques, which yield a powder of the inactive-MVA plus any additional desired ingredient from a previously sterile-filtered solution thereof.

In some embodiments, the inactivated-MVA compositions of the present disclosure may be formulated in aqueous solutions, or in physiologically compatible solutions or buffers such as Hanks's solution, Ringer's solution, mannitol solutions or physiological saline buffer. In certain embodiments, any of the inactivated-MVA compositions may contain formulator agents, such as suspending, stabilizing penetrating or dispersing agents, buffers, lyoprotectants or preservatives such as polyethylene glycol, polysorbate 80, 1-dodecylhexahydro-2H-azepin-2-one (laurocapran), oleic acid, sodium citrate, Tris HCl, dextrose, propylene glycol, mannitol , polysorbate polyethylenesorbitan monolaurate (Tween®-20), isopropyl myristate, benzyl alcohol, isopropyl alcohol, ethanol sucrose, trehalose and other such generally known in the art may be used in any of the compositions of the instant disclosure [84].

The biologic or pharmaceutical compositions of the present disclosure can be formulated to allow the virus contained therein to be available to infect tumor cells upon administration of the composition to a subject. The level of virus in serum, tumors, and if desired other tissues after administration can be monitored by various well-established techniques, such as antibody-based assays (e.g., ELISA, immunohistochemistry, etc.).

Dosage of Inactivated-MVA

In general, the subject is administered a dosage of inactivated-MVA in the range of about $10^5$ to about $10^{10}$ plaque forming units (pfu), although a lower or higher dose may be administered as will be determined by a person of ordinary skill. In a preferred embodiment, dosage is about $10^6$-$10^9$ pfu. This dosage can be formulated in unit dosage forms of about 1 to about 10 ml. The equivalence of pfu to virus particles can differ according to the specific pfu titration method used. Generally, pfu is equal to about 5 to 100 virus particles. A therapeutically effective amount of inactivated-MVA can be administered in one or more divided doses for a prescribed period of time and at a prescribed frequency of administration. For example, therapeutically effective amount of inactivated MVA in accordance with the present disclosure may vary according to factors such as the disease state, age, sex, weight, and general condition of the subject, the size of the tumor, the ability of inactivated-MVA to elicit a desired immunological response to a degree sufficient to combat the tumor in the particular subject and the ability of the immune system of the subject to mount such a response.

As is apparent to persons working in the field of cancer therapy, variation in dosage will necessarily occur depending for example on the condition of the subject being treated, route of administration and the subject's responsiveness to the therapy and the maximum tolerated dose for the subject. In delivering inactivated-MVA to a subject, the dosage will also vary depending upon such factors as the general medical condition, previous medical history, disease progression, tumor burden and the like.

It may be advantageous to formulate compositions of present disclosure in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable carrier.

Administration and Therapeutic Regimen of Inactivated-MVA

Administration of inactivated-MVA can be achieved using a combination of routes, including parenteral, for example intratumoral, or intravenous administration. In one embodiment, inactivated-MVA is administered directly into the tumor, e.g. by intratumoral injection, where a direct local reaction is desired. Additionally, administration routes of inactivated-MVA can vary, e.g., first administration using an intratumoral injection, and subsequent administration via an intravenous injection, or any combination thereof. A therapeutically effective amount of inactivated-MVA injection can be administered for a prescribed period of time and at a prescribed frequency of administration. In certain embodiments, inactivated-MVA can be used in conjunction with other therapeutic treatments. For example, inactivated-MVA can be administered in a neoadjuvant (preoperative) or adjuvant (postoperative) setting for subjects inflicted with bulky primary tumors. It is anticipated that such optimized therapeutic regimen will induce an immune response against the tumor, and reduce the tumor burden in a subject before and/or after primary therapy, such as surgery. Furthermore, inactivated-MVA can be administered in conjunction with other therapeutic treatments such as chemotherapy or radiation.

In certain embodiments, the inactivated-MVA virus is administered repeatedly at spaced apart intervals, for example at least once weekly or monthly but can be administered more often if needed, such as two times weekly for several weeks, months, years or even indefinitely as long as s persist. More frequent administrations are contemplated if tolerated and if they result in sustained or increased benefits. Benefits of the present methods include but are not limited to the following: reduction of the number of cancer cells, reduction of the tumor size, eradication of tumor, inhibition of cancer cell infiltration into peripheral organs, inhibition or stabilization of metastatic growth, inhibition or stabilization of tumor growth, and stabilization or improvement of quality of life. Furthermore, the benefits may include induction of an immune response against the tumor, activation of T helper cells, an increase of cytotoxic $CD8^+$ T cells, or reduction of regulatory $CD4^+$ cells. For example, in the context of melanoma or, a benefit may be a lack of recurrences or metastasis within one, two, three, four, five or more years of the initial diagnosis of melanoma. Similar assessments can be made for colon cancer and other solid tumors.

In certain other embodiments, the tumor mass or tumor cells are treated with inactivated-MVA in vivo, ex vivo, or in vitro.

EXAMPLES

Materials and Methods

Generally, reagents employed herein are from commercial sources or I, not, counterparts thereof are available commercially or publicly.

Viruses and Cell Lines

MVA viruses were kindly provided by Gerd Sutter (University of Munich), propagated in BHK-21 (baby hamster kidney cell, ATCC CCL-10) cells, but both materials are commercially and/or publicly available. Viruses were purified through a 36% sucrose cushion. B SC40 cells were maintained in Dulbecco's modified Eagle's medium (DMEM, can be purchased from Life Technologies, Cat#11965-092) supplemented with 5% fetal bovine serum (FBS), penicillin (100 units/ml), and streptomycin (100 µg/ml). BHK-21 were cultured in Eagle's Minimal Essential Medium (Eagle's MEM, can be purchased from Life Technologies, Cat#11095-080) containing 10% FBS, 0.1 mM nonessential amino acids (NEAA), and 50 mg/ml gentamycin. The murine melanoma cell line B16-F10 was originally obtained from I. Fidler (MD Anderson Cancer Center). B16-F10 cells were maintained in RPMI 1640 medium supplemented with 10% FBS, 100 Units/ml penicillin, 100 µg/ml streptomycin, 0.1 mM NEAA, 2 mM L-glutamine, 1 mM sodium pyruvate, and 10 mM HEPES buffer.

All cells were grown at 37.0 in a 5% CO2 incubator.

Heat-MVA was generated by incubating purified MVA virus at 55° C. for 1 hour. For generation of UV-MVA, MVA was UV irradiated in a Stratalinker 1800 UV cross-linker (Stratagene) with a 365 nm UV lamp for 15 min. Mice Female C57BL/6J mice between 6 and 10 weeks of age were purchased from the Jackson Laboratory (Stock #000664) and were used for the preparation of bone marrow-derived dendritic cells and for in vivo experiments. These mice were maintained in the animal facility at the Sloan Kettering Institute. All procedures were performed in strict accordance with the recommendations in the Guide for the Care and Use of Laboratory Animals of the National Institute of Health. The protocol was approved by the Committee on the Ethics of Animal Experiments of Sloan-Kettering Cancer Institute. $cGAS^{-/-}$, $IRF7^{-/-}$, $IRF5^{-/-}$, $Batf3^{-/-}$, and $STING^{Gt/Gt}$ mice were generated in the laboratories of Drs. Zhijian Chen (University of Texas Southwestern Medical Center; $cGAS^{-/-}$), Tadatsugu Taniguchi (University of Tokyo; $IRF3^{-/-}$ and $IRF7^{-/-}$), Tak Mak (University of Toronto; $IRF5^{-/-}$); Kenneth Murphy (Washington University; $Batf3^{-/-}$), and Russell Vance (University of California, Berkeley; $STING^{Gt/Gt}$). $IFNAR1^{-/-}$ mice were provided by Dr. Eric Pamer (Sloan Kettering Institute); the mice were purchased from B&K Universal and were backcrossed with C57BL/6 mice for more than six generations. $IRF5^{-/-}$ mice were backcrossed to C57BL/6J mice for at least six generations in Dr. Paula M. Pitha's laboratory before they were transferred to Sloan Kettering Institute.

Commercial sources for the foregoing animals are as follows:

| Mice | Source | Commercial |
|---|---|---|
| $cGAS^{-/-}$ | Zhijian Chen | Jackson Stock# 026554 |
| $STING^{Gt/Gt}$ | Russell Vance | Jackson stock# 017537 |
| $IRF3^{-/-}$ | T. Taniguchi | Taniguchi lab www2.brc.riken.jp/lab/animal/detail.php?reg_no=RBRC00858 |
| $IRF7^{-/-}$ | T. Taniguchi | Taniguchi lab www2.brc.riken.jp/lab/animal/detail.php?brc_no=RBRC01420 |
| $IRF5^{-/-}$ | Tak Mak | Jackson stock# 017311 |
| $Batf3^{-/-}$ | Kenneth Murphy | Jackson stock# 013755 |

| Mice | Source | Commercial |
|---|---|---|
| IFNAR1$^{-/-}$ | Eric Pamer | Jackson stock# 010830 |

Generation of Bone Marrow-Derived Dendritic Cells

The bone marrow cells from the tibia and femur of mice were collected by first removing muscles from the bones, and then flushing the cells out using 0.5 cc U-100 insulin syringes (Becton Dickinson) with RPMI with 10% FCS. After centrifugation, cells were re-suspended in ACK Lysing Buffer (Lonza) for red blood cells lysis by incubating the cells on ice for 1-3 min. Cells were then collected, re-suspended in fresh medium, and filtered through a 40-µm cell strainer (BD Biosciences). The number of cells was counted. For the generation of GM-CSF-BMDCs, the bone marrow cells (5 million cells in each 15 cm cell culture dish) were cultured in CM in the presence of GM-CSF (30 ng/ml, produced by the Monoclonal Antibody Core facility at the Sloan Kettering Institute) for 10-12 days. CM is RPMI 1640 medium supplemented with 10% fetal bovine serum (FBS), 100 Units/ml penicillin, 100 µg/ml streptomycin, 0.1 mM essential and nonessential amino acids, 2 mM L-glutamine, 1 mM sodium pyruvate, and 10 mM HEPES buffer. Cells were fed every 2 days by replacing 50% of the old medium with fresh medium and re-plated every 3-4 days to remove adherent cells. Only non-adherent cells were used for experiments.

RNA Isolation and Real-Time PCR

RNA was extracted from whole-cell lysates with an RNeasy Mini kit (Qiagen) and was reverse transcribed with a First Strand cDNA synthesis kit (Fermentas). Quantitative real-time PCR was performed in triplicate with SYBR Green PCR Mater Mix (Life Technologies) and Applied Biosystems 7500 Real-time PCR Instrument (Life Technologies) using gene-specific primers. Relative expression was normalized to the levels of glyceraldehyde-3-phosphate dehydrogenase (GAPDH).

The following primers were used for real-time PCR:

```
                                        (SEQ ID NO: 1)
IFNA4 forward:      5'-CCTGTGTGATGCAGGAACC-3', (SEQ ID NO: 2)
IFNA4 reverse:      5'-TCACCTCCCAGGCACAGA-3';

(SEQ ID NO: 3)
IFNB forward:       5'-TGGAGATGACGGAGAAGATG-3', (SEQ ID NO: 4)
IFNB reverse:       5'-TTGGATGGCAAAGGCAGT-3';

(SEQ ID NO: 5)
GAPDH forward:      5'-ATCAAGAAGGTGGTGAAGCA-3', (SEQ ID NO: 6)
GAPDH reverse:      5'-AGACAACCTGGTCCTCAGTGT-3.
```

Relative expression was normalized to the levels of glyceraldehyde-3-phosphate dehydrogenase (GAPDH).

Cytokine Assays

Cells were infected with various viruses at a MOI of 10 for 1 h or mock infected. The inoculum was removed and the cells were washed with PBS twice and incubated with fresh medium. Supernatants were collected at various times post infection. Cytokine levels were measured by using enzyme-linked immunosorbent assay (ELISA) kits for IFN-α/β (PBL Biomedical Laboratories), IL-6, CCL4, and CCL5 (R & D systems).

Western Blot Analysis

BMDCs ($1 \times 10^6$) from WT and KO mice were infected with MVA at a MOI (multiplicity of infection) of 10 or an equivalent amount of Heat-MVA, or UV-MVA. At various times post-infection, the medium was removed and cells were collected. Whole-cell lysates were prepared. Equal amounts of proteins were subjected to sodium dodecyl sulfate-polyacrylamide gel electrophoresis and the polypeptides were transferred to a nitrocellulose membrane. Phosphorylation of IRF3 was determined using a rabbit polyclonal antibody specific for phosphoserine-396 of IRF3 (Cell Signaling). The level of IRF3 was determined using a rabbit polyclonal antibody against IRF3 (Cell Signaling). Anti-STING antibodies were purchased from Cell Signaling. Vaccinia E3 protein level was determined by using anti-E3 monoclonal antibody (MAb 3015B2) kindly provided by Dr. Stuart N. Isaacs (University of Pennsylvania) [85]. Anti-glyceraldehyde-3-phosphate dehydrogenase (GADPH) or anti-β-actin antibodies (Cell Signaling) were used as loading controls.

B16-F10 melanoma cells were infected with MVA at a MOI of 10 or with an equivalent amount of Heat-MVA. Cell lysates were collected at various times post infection. Western blot analysis was performed using anti-phospho-IRF3, anti-IRF3, and anti-GAPDH antibodies as described above.

Unilateral Intradermal Tumor implantation and Intratumoral Injection with Viruses in the Presence or Absence of Systemic Administration of Immune Checkpoint Blockade B16-F10 melanoma ($1 \times 10^5$ cells in a volume of 50 µl) were implanted intradermally into the shaved skin on the right flank of STING$^{Gt/Gt}$, or Batf3$^{-/-}$, or age-matched WT C57BL/6J mice. After 10 to 12 days post implantation, tumor sizes were measured and tumors that are 3 mm in diameter or larger will be injected with Heat-MVA (equivalent to $2 \times 10^7$ pfu of MVA in a volume of 50 µl) or PBS when the mice were under anesthesia. Viruses were injected weekly or twice weekly as specified in each experiment. Mice were monitored daily and tumor sizes were measured twice a week. Tumor volumes were calculated according the following formula: 1 (length)×w (width)×h(height)/2. Mice were euthanized for signs of distress or when the diameter of the tumor reached 10 mm. Serum were collected when the mice were euthanized.

To evaluate the combination of Heat-MVA with immune checkpoint blockade, we treated the mice either with intratumoral injection of Heat-MVA or PBS in the presence or absence of anti-CTLA-4 antibody (100 µg in a volume of 100 µl) delivered intraperitoneally. The mice received virus and antibodies every 3-4 days (twice per week). The animals were monitored daily, and measured for tumor size every 3 days. Tumor volumes were calculated according the following formula: 1 (length)×w (width)×h(height)/2. Mice were euthanized for signs of distress or when the diameter of the tumor reached 10 mm.

In some cases, $1 \times 10^5$ MC38 colon adenocarcinoma cells were implanted intradermally on the right flank of shave mice. After 7 days, tumors were injected with either PBS, Heat-MVA, or UV-MVA at the same dose as described above twice weekly. The animals were monitored daily, and measured for tumor size every 3 days. Tumor volumes were calculated according the following formula: l (length)×w (width)×h(height)/2. Mice were euthanized for signs of distress or when the diameter of the tumor reached 10 mm.

Tumor Challenge to Assess the Development of Systemic Antitumor Immunity

For the B16-F10 murine melanoma model, tumors were implanted by injection of $1\times10^5$ cells (in a volume of 50 µl) on the right flank intradermally and treated with intratumoral delivery of PBS or Heat-MVA (an equivalent of heat-inactivated $2\times10^7$ pfu of MVA in a volume of 50 µl). The mice were monitored for tumor growth and survival for 30-80 days. The survived mice were rechallenged with either intradermally delivery of a lethal dose of B16-F10 ($1\times10^5$ cells) at the contralateral side. Mice were monitored for 30-80 days for tumor growth. Alternatively, they were challenged by intravenous delivery of a lethal dose of B16-F10 ($1\times10^5$ cells) and then euthanized at 3 weeks post rechallenge to evaluate the presence of tumors on the surface of lungs.

For the MC38 murine colon adenocarcinoma model, tumors were implanted by injection of $1\times10^5$ cells in the right flank intradermally and treated with intratumoral delivery of PBS, Heat-MVA, or UV-MVA (an equivalent of heat- or UV-inactivated $2\times10^7$ pfu of MVA). The mice were monitored for tumor growth and survival for 60 days. The survived mice were rechallenged with either intradermally delivery of a lethal dose of B16-F10 ($1\times10^5$ cells) at the contralateral side. Mice were monitored for 60 days for tumor growth.

T Cell Depletion Experiment

B16-F10 murine melanoma cells ($1\times10^5$ cells in a volume of 50 µl) were implanted intradermally into the right flank of shaved WT C57B/6 mice at 6-8 weeks of age. At 8 days post tumor implantation, the tumors were injected with either Heat-MVA (an equivalent dose of $2\times10^7$ pfu of MVA) or PBS twice weekly. Depletion antibodies for $CD4^+$, $CD8^+$ and NK cells (200 µg of GK1.5, 2.43, and PK136) (Monoclonal Antibody Core Facility, MSKCC) (ref, Avogadri et al., PloS One 2010) were injected intraperitoneally twice weekly starting one day prior to viral injection, and they were used until the animals either died, or were euthanized, or were completely clear of tumors. Mice were monitored daily and tumor sizes were measured. The depletion of targeted immune cells was validated by FACS of peripheral blood of mice after 4 doses of antibodies.

Bilateral Tumor Implantation Model and Intratumoral Injection with Viruses in the Presence or Absence of Systemic or Intratumoral Administration of Immune Checkpoint Blockade Briefly, B16-F10 melanoma cells were implanted intradermally to the left and right flanks of C57B/6 mice ($5\times10^5$ to the right flank and $1\times10^5$ to the left flank). 8 days after tumor implantation, we intratumorally inject $2\times10^7$ pfu of MVA or an equivalent amount of Heat-MVA to the larger tumors on the right flank. The tumor sizes were measured and the tumors were injected twice a week. The survival of mice was monitored.

In some experiments, MC38 colon adenocarcinoma cells were implanted intradermally to the left and right flanks of C57B/6 mice ($5\times10^5$ to the right flank and $1\times10^5$ to the left flank).

In some experiments, $STING^{Gt/Gt}$, $Batf3^{-/-}$ mice and WT age-matched controls were used for bilateral B16-F10 melanoma implantation, and treated with PBS or Heat-MVA to the larger tumors on the right flank of the mice.

In some experiments, the mice with bilateral tumors were treated with intratumoral injection of Heat-MVA to the larger tumors on the right flank and intraperitoneal delivery of immune checkpoint blockade antibodies, including anti-CTLA-4, anti-PD-1, or anti-PD-L1.

In some experiments, the mice with bilateral tumors were treated with intratumoral injection of both Heat-MVA and anti-CTLA-4 antibody (with one tenth of dose of as used for intraperitoneal delivery) to the larger tumors on the right flank. The sizes of both injected and non-injected tumors were measured and the survival of the mice was monitored.

Flow Cytometry Analysis of DC Maturation

For DC maturation analysis, BMDCs were generated from WT and $STING^{Gt/Gt}$ mice and infected with MVA at a MOI of 10 or with an equivalent amount of Heat-MVA. Cell were collected at 14 h post infection and were then fixed with Fix Buffer I (BD Biosciences) for 15 min at 37° C. Cells were washed, permeabilized with PermBuffer (BD Biosciences) for 30 min on ice, and stained with antibodies against MHC Class I, CD40, CD86, and CD80 for 30 min. Cells were analyzed using the LSRII Flow cytometer (BD Biosciences). Data were analyzed with FlowJo software (Treestar).

Flow Cytometry Analysis of Tumor Infiltrating Immune Cells

To analyze immune cell phenotypes and characteristics in the tumors or tumor draining lymph nodes, we generated cell suspensions prior to FACS analysis according to the following protocol (Zamarin et al., 2014). First we isolated injected and/or non-injected tumors using forceps and surgical scissors three days post second treatment and 7 days post first treatment with PBS, MVA or Heat-MVA. The tumors were then weighed. Tumors or tumor draining lymph nodes were minced prior to incubation with Liberase (1.67 Wunsch U/ml) and DNase (0.2 mg/ml) for 30 minutes at 37° C. Cell suspensions were generated by repeated pipetting, filtered through a 70-µm nylon filter, and then washed with complete RPMI prior to Ficoll purification to remove dead cells. Cells were processed for surface labeling with anti-CD3, CD45, CD4, and CD8 antibodies. Live cells are distinguished from dead cells by using fixable dye eFluor506 (eBioscience). They were further permeabilized using FoxP3 fixation and permeabilization kit (eBioscience), and stained for Ki-67, FoxP3, and Granzyme B. Data were acquired using the LSRII Flow cytometer (BD Biosciences). Data were analyzed with FlowJo software (Treestar).

Anti-Melanoma and Anti-Viral Antibody Measurement by ELISA

To determine anti-B16 melanoma antibody concentrations in the serum of the mice, $5\times10^4$ B16-F10 cells in 100 µl medium/well were add to 96 well culture plate and incubated overnight at 37° C. The plates were washed twice with PBST. Cells were treated with 10% buffered formalin (125 µl) and fixed for 15 min at room temperature. The plates were then washed three times with PBS. After blocking with PBS with 1% BSA (250 µl) at room temperature for 1 h, mouse serum diluted in PBS with 1% BSA (1:500) was added at 100 µl/well. The plate was washed with PBST five times. Incubate for 1 hr at 37° C. Then horseradish peroxidase (HRP)-conjugated anti-mouse IgG diluted in PBS with 1% BSA (1:2000) was added to the plate and incubated for 1 hr at 37° C. The plate was washed with PBS five times and incubated with substrate 3,3',5,5'-Tetramethylbenzidine TMB (100 µl/well) at room temperature for 10 min. The reaction was terminated by adding sulfuric acid (2N, 50

µl/well). The optical density of each well was determined by using a microplate reader set to 450 nm.

To determine anti-vaccinia viral antibody concentrations in the serum of the mice, Heat-MVA (10 µg/ml) in 100 µl PBS/well were added to 96 well culture plate and incubated overnight at 37° C. The plates were washed twice with PBST. After blocking with PBS with 1% BSA (250 µl) at room temperature for 1 h, mouse serum diluted in PBS with 1% BSA (1:200) was added at 100 µl/well. The rest of the detection protocol is the same as stated above.

Reagents

The commercial sources for reagents were as follows: CpG oligodeoxynucleotide ODN2216 (Invitrogen); We used the following antibodies. Therapeutic anti-CTLA4 (clone 9H10 and 9D9), anti-PD1 (clone RMP1-14) were purchased from BioXcell; Antibodies used for flow cytometry were purchased from eBioscience (CD45.2 Alexa Fluor 700, CD3 PE-Cy7, CD4 APC-efluor780, CD8 PerCP-efluor710, FOXP3 Alexa Fluor 700, MHC Class I APC, CD40 APC, CD80 APC, CD86 APC), Invitrogen (CD4 QDot 605, Granzyme B PE-Texas Red, Granzyme B APC), BD Pharmingen (Ki-67-Alexa Fluor 488).

Statistics

Two-tailed unpaired Student's t test was used for comparisons of two groups in the studies. Survival data were analyzed by log-rank (Mantel-Cox) test. The p values deemed significant are indicated in the figures as follows: *, $p<0.05$; , $p<0.01$; *, $p<0.001$; ****, $p<0.0001$.

Example 1

Heat-Inactivated MVA Induces Higher Levels of type I IFN Production in Murine cDCs than MVA To test whether heat-inactivation of MVA (Heat-MVA) would result in higher levels of type I IFN induction than MVA, MVA was incubated at 55° C. for 1 h, which resulted in the reduction of infectivity by 1000-fold. Bone marrow-derived dendritic cells were cultured in the presence of GM-CSF (GM-CSF-BMDCs or cDCs) and infected with either MVA at a multiplicity of infection (MOI) of 10 or with an equivalent amount of Heat-MVA. Cells were harvested at 6 h post infection and quantitative real-time PCR analysis of RNA isolated from infected cells and mock-infected cells was performed. It was found that MVA infection of cDCs increased IFNA4 and IFNB mRNA levels by 4.8-fold and 148-fold, respectively, compared mock-infected cells. By contrast, infection of Heat-MVA dramatically increased IFNA4 and IFNB mRNA levels by 22.4-fold and 607-fold, respectively (FIG. 1A). These results indicate that Heat-MVA is a stronger inducer of IFNA4 and IFNB gene expression than MVA (***, $p<0.001$).

Figure 1B:
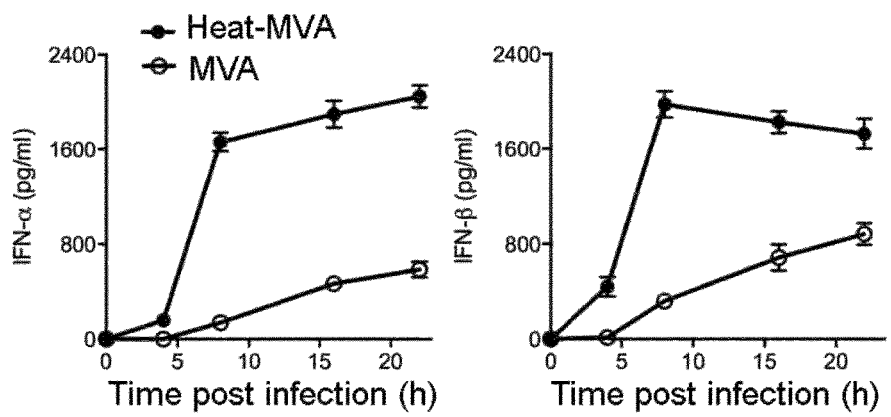
Figure 1C:
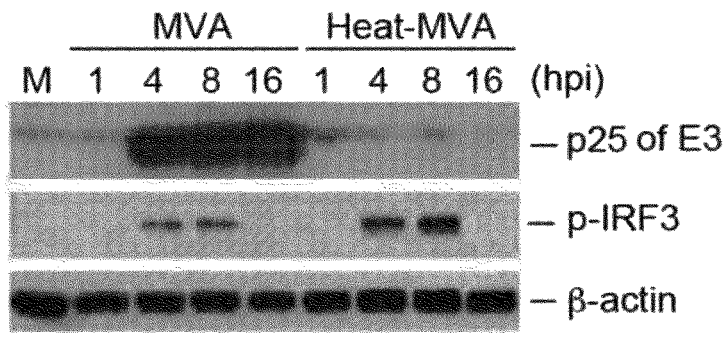

To assess the kinetics of induction of type I IFN secretion by Heat-MVA or MVA-infected cDCs, supernatants were collected at various times (0, 4, 8, 16, and 22 hours) post Heat-MVA or MVA infection, and the levels of secreted IFN-α and IFN-β were determined by ELISA. Heat-MVA strongly induced both IFN-α (1650 pg/ml) and IFN-β (1975 pg/ml) at 8 h post-infection, which were 10-fold and 6-fold higher than those induced by MVA at the same time point. Whereas MVA-induced IFN-α and IFN-β continued to rise between 8 h and 22 h post infection, Heat-MVA induced IFN-α levels increased modestly during this time frame, while Heat-MVA induced IFN-β peaked at 8 h post infection and leveled off thereafter (FIG. 1B). Western blot analysis showed that E3 protein, which attenuates innate immune responses, was not produced in Heat-MVA infected cDCs, but was expressed in MVA-infected cells (FIG. 1C). Furthermore, Heat-MVA triggered higher levels of IRF3 phosphorylation than MVA at 4 and 8 h post infection (FIG. 1C). Taken together, these results demonstrate that Heat-MVA is a stronger inducer of type I IFN production in cDCs than MVA.

Example 2

Heat-MVA-Induced Type I IFN Production is Dependent on the Cytosolic DNA-Sensing Pathway Mediated by cGAS/STING, and Transcription Factors IRF3/IRF7, and IFNAR1

To test whether Heat-MVA infection of cDCs triggers type I IFN induction via the cytosolic DNA-sensing pathway mediated by the cytosolic DNA sensor cGAS (cyclic GMP-AMP synthase) [62, 63], and its adaptor STING [59, 69], cDCs were generated from cGAS$^{-/-}$ [86] mice and age-matched WT controls and infected with Heat-MVA. Using quantitative real-time PCR analysis, it was found that Heat-MVA-induced IFNA4 and IFNB gene expression at 6 h post infection were both diminished in cGAS-deficient cells (FIGS. 2A, 2B). Analysis of supernatants collected at 22 h post infection also showed that Heat-MVA-induced IFN-α/β secretion was abolished in cGAS-deficient cells (FIGS. 2A, 2B).

STING is a critical adaptor for the cytosolic DNA-sensing pathway [59, 69, 87, 88]. cDCs were also generated from STING$^{Gt/Gt}$ mice, which lack functional STING [89]. It was found that Heat-MVA induced type I IFN gene expression and that IFN-α/β secretion from the cDCs is also dependent on STING (FIG. 2C, D). Western blot analysis demonstrated that Heat-MVA induced phosphorylation of IRF3 at ser-396 at 4 and 8 h post infection, which was abolished in cGAS or STING-deficient cells (FIG. 2E, F). To test whether heat-MVA infection triggers DC maturation via the cytosolic DNA-sensing pathway, cDCs from STING$^{Gt/Gt}$ mice and age-matched WT controls were infected with Heat-MVA. Cells were collected at 14 h post infection and stained for DC activation marker, including MEW class I (MHO) CD40, CD86, and CD80. Heat-MVA infection markedly induced the expression of CD40 and CD86, and mildly increased the expression of MHC I and CD80 in WT cells (FIG. 2G). However, the expression of the activation markers was significantly reduced in STING-deficient cells (FIG. 2G). These results indicate that Heat-MVA induction of DC maturation is largely mediated through the cytosolic DNA-sensing pathway. Our results imply that the viral DNAs from MVA and Heat-MVA are released to the cytosol of infected cDCs and are detected by the cytosolic DNA sensor cGAS, which in turn generates the second messenger cGAMP, resulting in the activation of STING and downstream signaling pathways.

To test whether Heat-MVA-induction of type I IFN requires IRF3, IRF5 and IRF7, in addition to cGAS and STING, cDC were generated from IRF3$^{-/-}$, IRF7$^{-/-}$ and age-matched WT mice, and infected with Heat-MVA. Heat-MVA-induced IFNA4 gene expression, and IFN-a protein production was dependent on IRF3 and IRF7, but independent of IRF5 (FIG. 3A, B). In addition, Heat-MVA-induced IFNB gene expression, and similarly to IFN-α secretion, IFN-β protein secretion was dependent on IRF3 and IRF7 but not IRF5 (FIG. 3A, B). Heat-MVA-induced IFNB gene expression and IFN-β production were reduced by 74% and 67%, respectively, in IRF7-deficient cells (FIG. 3A, B). Heat-MVA-induced IFNA4 gene expression and IFN-α protein secretion were dependent on IFNAR1, whereas Heat-MVA-induced IFNB gene expression and IFN-β secretion were reduced by 82% and 62%, respectively, in IFNAR1-deficient cells (FIG. 3C, D). These results indicate that Heat-MVA-induced type I IFN induction requires transcriptional factors IRF3 and IRF7, as well as the Type I IFN positive feedback loop mediated by IFNAR1.

Example 3

Heat MVA Induces Higher Levels of Type I IFN than MVA In Vivo

Figure 4A:
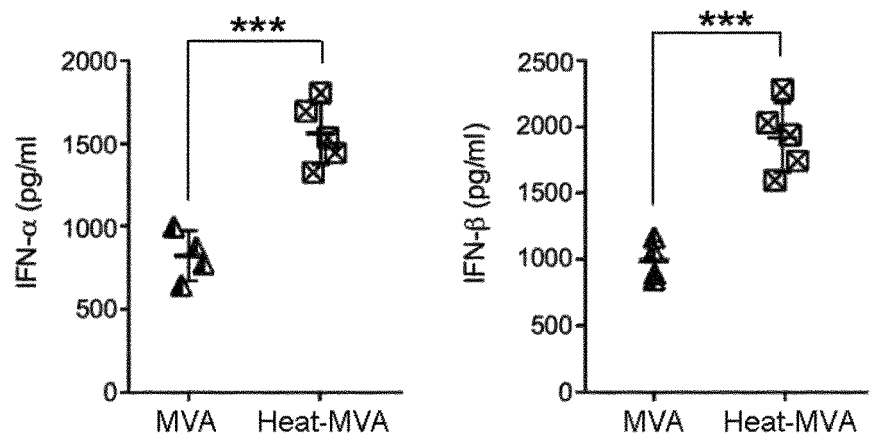
FIGS. 4A-C are a series of scatterplots showing that Heat-MVA induces higher levels of type I IFN than MVA in vivo and it does so in a STING/IRF3/IRF7-dependent manner.

To test whether Heat-MVA induces higher levels of type I IFN than MVA in vivo, Heat-MVA or MVA were inoculated into C57B/6 mice via tail vein injection, and serum was collected at 6 h post-infection. The levels of both IFN-α and IFN-β in the serum were significantly higher in Heat-MVA-treated mice than in MVA-treated mice (FIG. 4A) (***, p<0.001). These results indicate that heat-MVA not only induces higher levels of type I IFN than MVA in cultured cDCs, but it also induces higher levels of type I IFN than MVA in vivo.

Example 4

Figure 4B:
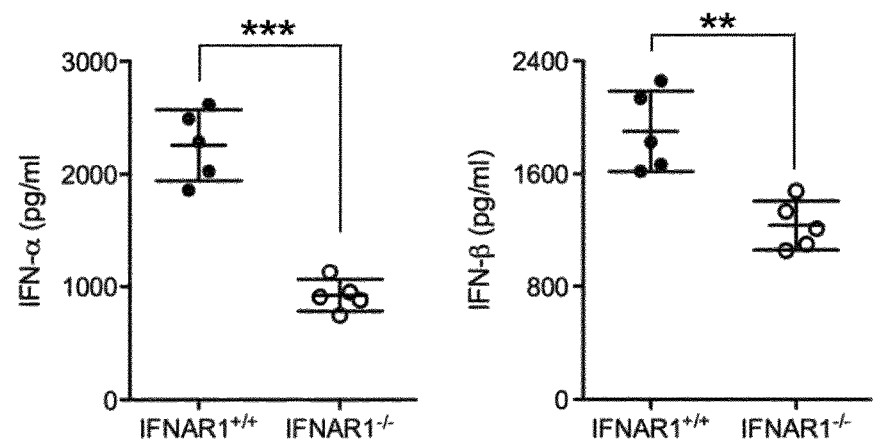

Heat MVA Triggers Type I IFN Production In Vivo in a STING/IRF3/IRF7-Dependent Manner To test whether Heat-MVA in vivo induction of type I IFN requires IFNAR1, intravenous (IV) inoculation of purified Heat-MVA via tail vein injection of IFNAR1$^{-/-}$ and WT age-matched control mice was performed. Heat-MVA infection of WT mice induced IFN-α and IFN-β production to the levels of 2256 pg/ml and 1901 pg/ml, which was reduced by 60% and 35%, respectively, in IFNAR1$^{-/-}$ mice (FIG. 4B) (,p<0.01; *, p<0.001).

Figure 4C:
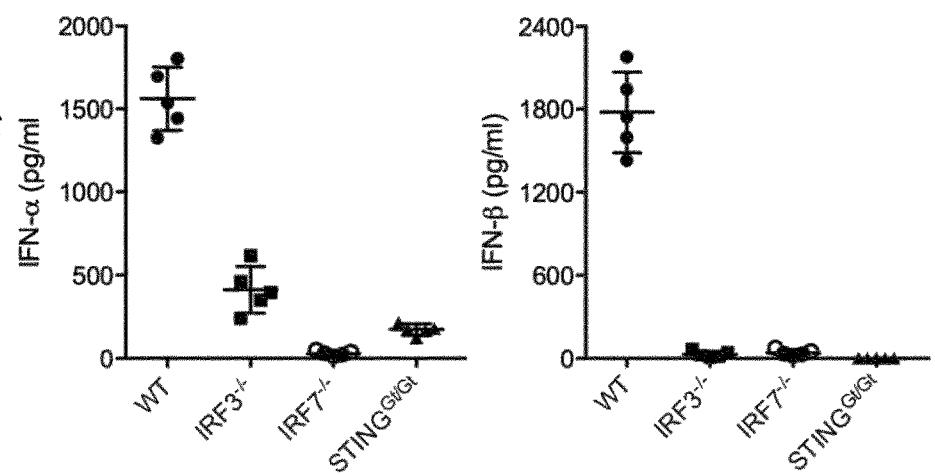

Heat-MVA-induced IFN-α secretion was reduced by 89% in STING$^{Gt/Gt}$ mice compared with WT controls, whereas Heat-MVA-induced IFN-β secretion was abolished in STING$^{Gt/Gt}$ mice (FIG. 4C), indicating that Heat-MVA-induced type I IFN production in vivo is also dependent on STING. Furthermore, it was found that Heat-MVA-induced IFN-α was reduced by 74% in IRF3$^{-/-}$ mice compared with WT controls, whereas Heat-MVA-induced IFN-β was reduced by 98% in IRF3$^{-/-}$ mice. Heat-MVA-induced IFN-α and IFN-β secretions were diminished in IRF7$^{-/-}$ mice (FIG. 4C). These results indicate that Heat-MVA-induced type I IFN in vivo requires STING and IRF3/IRF7.

Example 5

Figures 5A, 5B, 5C, 5D:
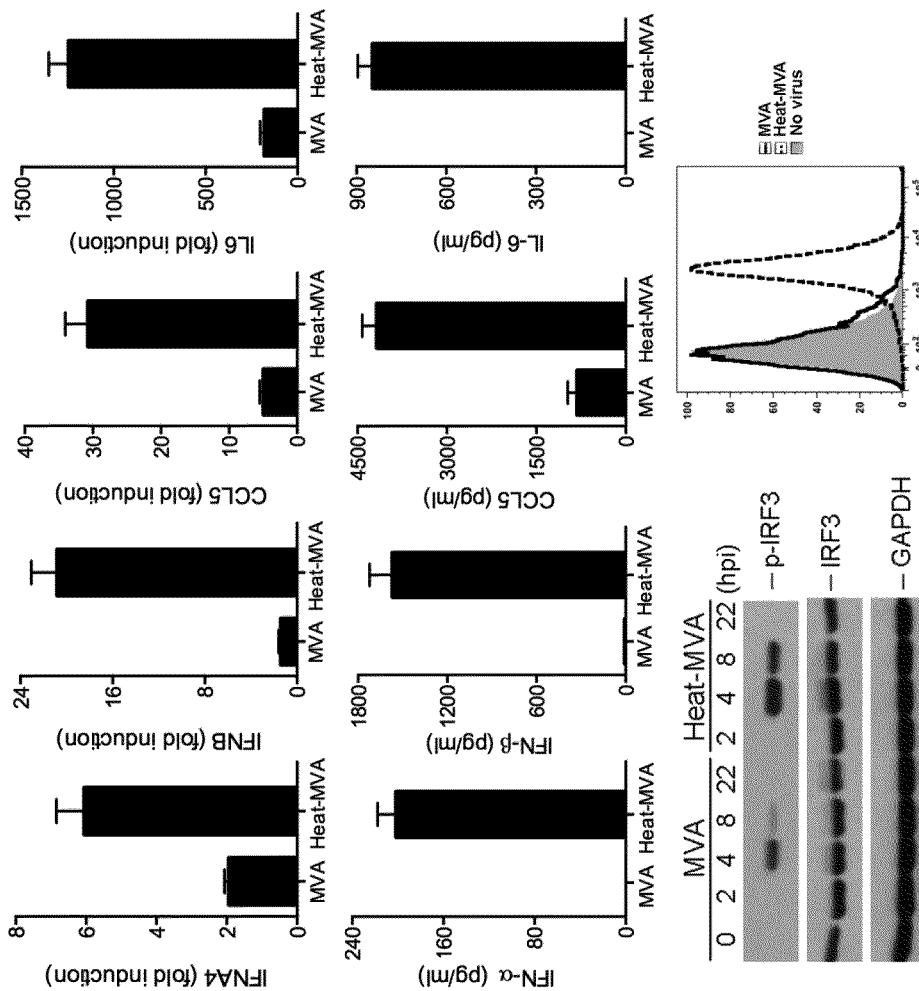
FIGS. 5A-D are a series of graphical representations of data showing that Heat-MVA infection of B16-F10 melanoma cells induces the production of type I IFN and proinflammatory cytokines and chemokines.

Heat MVA infection of B16-F10 Melanoma Cells Induces the Production of Type I IFN and Proinflammatory Cytokines and Chemokines To test whether Heat-MVA infection of tumor cells triggers innate immune responses, B16-F10 melanoma cells were infected with MVA at an MOI of 10, or with equivalent amounts of Heat-MVA, and cells were collected at 6 h post infection and supernatants were collected at 22 h post infection. Quantitative real-time PCR analysis showed that Heat-MVA infection of B16-F10 cells induced higher levels of Ifna4, Ifnb, Ccl5, and Il6 gene expression than MVA (FIG. 5A). ELISA analysis showed that Heat-MVA induced higher levels of IFN-α, IFN-β, CCL5, and IL-6 protein secretion in B16-F10 cells than MVA (FIG. 5B). Western blot analysis demonstrated that Heat-MVA infection induces higher levels of phosphorylation of IRF3 in B16-F10 melanoma cells than MVA (FIG. 5C). Furthermore, Heat-MVA infection induced the expression of MHC Class I molecule expression on B16 cells, whereas MVA infection failed to do so. These results suggest that Heat-MVA infection of B16 cells not only induces innate immune responses against tumor cells through the release of type I IFN and proinflammatory cytokines and chemokines, but also changes (enhances) the immunogenicity of the tumors through the induction of MHC Class I molecules on the tumor cells.

Example 6

55° C. for 1 h is an Optimal Condition to Inactivate MVA

To evaluate whether 55° C. is the optimal temperature for inactivating MVA, we incubated MVA at various different temperatures, including, 45° C., 50° C., 55° C., 60° C., and 65° C., for one hour. cDCs from WT mice were infected with these virus preparations and supernatants were collected at 22 h post infection. The concentrations of secreted IFN-α and IFN-β were measured by ELISA. We found that infection with MVA inactivated at 55° C. for one hour induced the highest levels of IFN-α and IFN-β secretion from cDCs (FIG. 6A, B).

Example 7

Figure 7A:
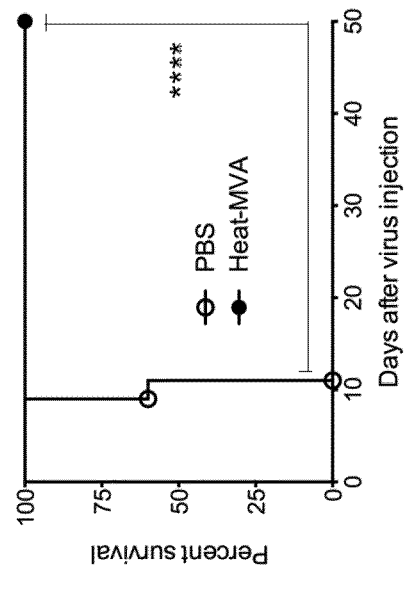
FIGS. 7A-D are a series of graphical representations of data showing that Heat-MVA injection leads to tumor eradication and systemic anti-tumoral immunity.
Figure 7B:
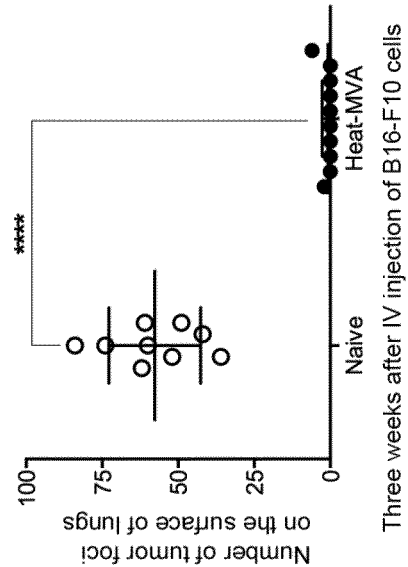

Intratumoral Injection of Heat MVA Leads to Tumor Eradication and Systemic Anti-Tumoral Immunity in a Murine Transplantable B16-F 10 Melanoma Model The transplantable in vivo B16-F10 melanoma model involves the intradermal implantation of murine B16-F10 melanoma cells ($1 \times 10^5$) on one side of the flank of C57B/6 mice. Ten days following tumor implantation, when the tumors were approximately 3 mm in diameter, Heat-MVA (with an equivalent of $2 \times 10^7$ pfu of MVA) or PBS were injected to the tumors weekly. Intratumoral injection of Heat-MVA resulted in tumor eradication and 100% survival of mice (FIG. 7A, B), demonstrating excellent therapeutic efficacy. By contrast, all of the mice with intratumoral injection of PBS had continued tumor growth and were euthanized at 19 and 21 days post tumor implantation (FIG. 7A, B).

Figure 7C:
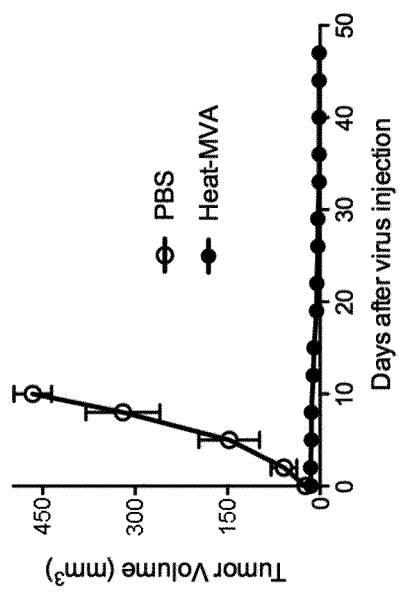
Figure 7D:
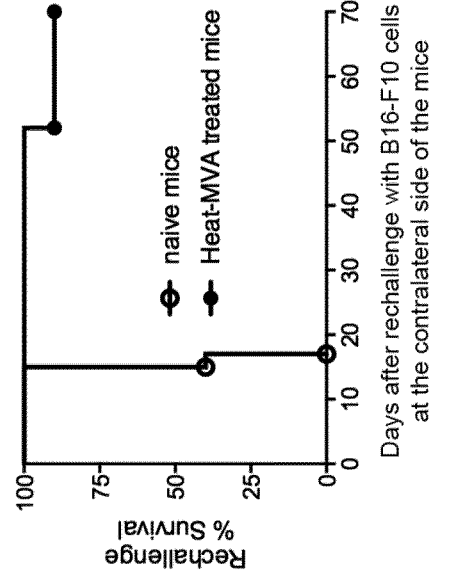

To test whether mice whose tumors were eradicated after intratumoral injection of Heat-MVA developed systemic anti-tumoral immunity, animals were challenged by intradermal implantation of a lethal dose of B16 melanoma cells ($1 \times 10^5$) to the contralateral side 8 weeks after the eradication of initial tumors. Naïve mice that were never exposed to B16 melanoma cells or heat-MVA were used as a control. Animals were followed for 70 days after tumor challenge. 90% of heat-MVA-treated mice survived the tumor challenge, whereas all of the naïve mice developed growing tumors and were eventually euthanized (FIG. 7C). To test whether Heat-MVA-treated mice developed systemic anti-tumor immunity at a different organ, analogous to metastasis, we tested whether Heat-MVA-treated mice can reject tumor challenge via intravenous delivery of B16-F10 melanoma cells. Both naïve mice and Heat-MVA-treated mice received $1 \times 10^5$ B16-F10 cells through intravenous delivery. Mice were euthanized at 3-week post tumor challenge. The lungs of the mice were collected and fixed in formalin containing solutions. The tumors on the surface of the lungs were visualized under a dissecting microscope and counted. We found that whereas all of the naïve mice developed tumors with an average of 58 visualized on the surface of the lungs, only one out of 10 Heat-MVA-treated mouse developed 2 tumor foci visible under the microscope (FIG. 7D, ****, p<0.0001). Collectively, these results indicate that intratumoral injection of Heat-MVA leads both to eradication of injected tumors and to the development of systemic antitumoral immunity. These results imply that intratumoral injection of Heat-MVA can elicit a strong tumor vaccine effect, possibly through enhanced tumor antigen presentation and the activation of tumor-specific T cells.

Example 8

Heat MVA Leads to Immunological Changes in the Tumor Microenvironment

To investigate the immunologic changes within the tumors induced by intratumoral injection of Heat-MVA, tumors were harvested at 3 days post intratumoral injection of Heat-MVA or PBS and the immune cell infiltrates were analyzed by FACS. The percentage of $CD3^+CD45^+$ T cells of live cells within the tumors increased from 6.5% in the PBS-treated tumors to 19.5% in the Heat-MVA-treated tumors (P=0.0002; FIG. 8A, G). An increase in the percentage of $CD8^+$ T cells that express Granzyme B (i.e. expressing the cytotoxic phenotype) was also observed within the tumors, and it ranged from 47.9% in PBS-treated tumors to 92.8% in Heat-MVA-treated tumors (P<0.0001; FIG. 8B, H). The percentage of $Ki-67^+CD8^+$ T cells (i.e., proliferating $CD8^+$ T cells) increased from 51.2% to 71.7% (P=0.0008; FIG. 8C, I). Similar changes were observed for $CD4^+$ T cells within the tumors treated with Heat-MVA compared with those treated with PBS; the percentage of Granzyme $B^+CD4^+$ T cells (i.e., activated T helper cells) rose dramatically from 3% in PBS-treated tumors to 57% in Heat-MVA-treated tumors (P=0.0002; FIG. 8D, J). Additionally, there was an increase in the percentage of $Ki-67^+CD4^+$ T cells (i.e. proliferating $CD4^+$ T cells) from 37.5% in PBS-treated tumors to 79% in Heat-MVA-treated tumors (P<0.0001; FIG. 8E and K). By contrast, the percentage of $Foxp3^+CD4^+$ T cells (i.e., regulatory $CD4^+$ T cells) decreased from 34.7% in PBS-treated tumors to 9.1% in Heat-MVA-treated tumors (P<0.0001; FIG. 8F, N). These results indicate that intratumoral injection of Heat-MVA dramatically upregulates immune responses in the tumor microenvironment, including proliferation and activation of helper $CD4^+$, cytotoxic $CD4^+$ (collectively, "effector T cells") and cytotoxic $CD8^+$ T cells and a concomitant reduction of $CD4^+$ regulatory T cells within the tumors. Taken together with the results of Example 8, these results indicate that intratumoral injection of Heat-MVA profoundly alters the tumor immune suppressive microenvironment to facilitate the development of antitumor immunity.

Example 9

Heat MVA Also Induces Immunological Changes in the Tumor-Draining Lymph Nodes (TDLNs)

To test whether intratumoral injection of Heat-MVA causes immunological changes in TDLNs, TDLNs were isolated from Heat-MVA-treated or PBS-treated mice and analyzed by FACS. The percentage of Granzyme $B^+CD8^+$ T cells in TDLNs increased from 0.15% in mice treated with PBS to 3.04% in mice treated with Heat-MVA (P<0.0001; FIG. 9A and E). In addition, the percentage of $Ki-67^+CD8^+$ T cells increased from 7.2% in mice treated with PBS to 17% in mice treated with Heat-MVA (P=0.0003; FIG. 9C, F). These results indicate that there are more activated and replicating $CD8^+$ T cells in the TDLNs in Heat-MVA-treated mice than in PBS-treated mice. Similar increase of activated and replicating $CD4^+$ T cells was also observed in Heat-MVA-treated mice compared with PBS-treated mice. The percentage of Granzyme $B^+CD4^+$ T cells in TDLNs increased from 0.25% in PBS-treated mice to 0.77% in Heat-MVA-treated mice (P=0.002; FIG. 9B, G), and the percentage of $Ki-67^+CD4^+$ T cells in TDLNs increased from 10.6% in PBS-treated mice to 18.4% in Heat-MVA-treated mice (P=0.002; FIG. 9D, H). Taken together, these results indicate that intratumoral injection of Heat-MVA leads to the activation and proliferation of both $CD8^+$ and $CD4^+$ T cells not only within the tumor but also in the circulation.

Example 10

Figures 10A, 10B:
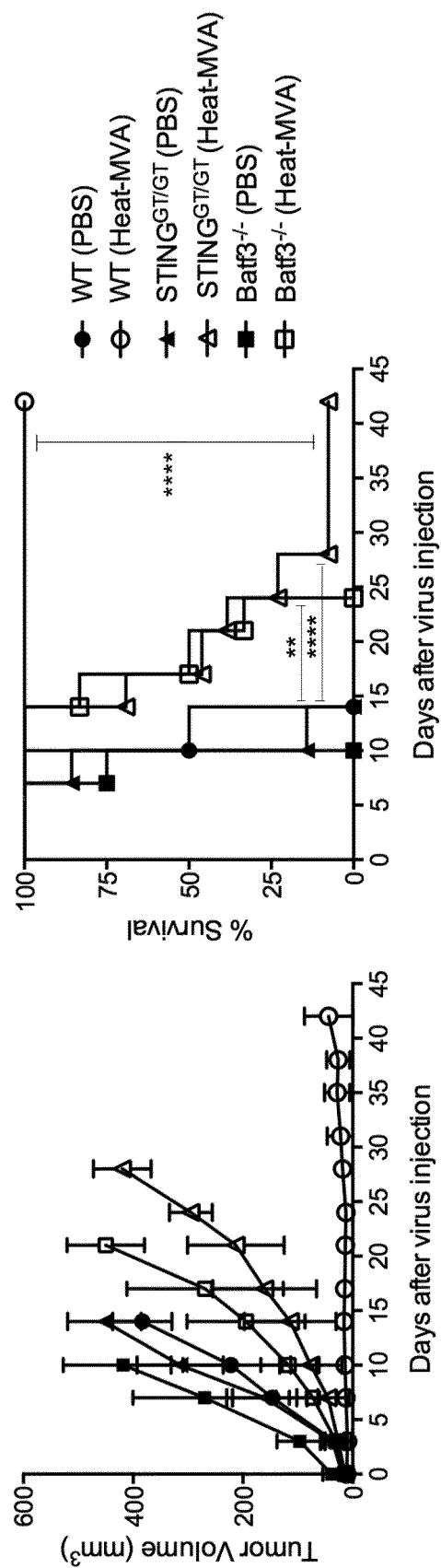
FIGS. 10A-B are a series of graphical representations of data showing that Heat-MVA is less effective in eradicating B16-F10 melanomas in STING-deficient mice or Batf3-deficient mice compared with wild-type controls.

Intratumoral Injection of Heat-MVA is Less Effective in Eradicating B16 Melanomas in STING-Deficient Mice or Batf3-Deficient Mice Compared with Wild-Type Controls Recent studies have shown that the STING-mediated cytosolic DNA-sensing pathway plays a role in spontaneous T cell responses against tumors as well as in radiation-induced antitumoral immunity [7, 8, 90]. BATF3 is a transcription factor that is critical for the development of $CD8\alpha^+$ lineage DCs, which play an important role in cross-presentation of viral and tumor antigens [91, 92]. Batf3-deficient mice were unable to reject highly immunogenic tumors [91]. To test whether STING or Batf3 plays a role in Heat-MVA-mediated tumor clearance, we implanted B16-F10 melanoma cells intradermally into the right flank of WT C57B/6, $STING^{Gt/Gt}$, or $Batf3^{-/-}$ mice. At 11 days post tumor implantation, the tumors were injected with either Heat-MVA (an equivalent dose of $2\times10^7$ pfu) or PBS on a weekly basis as indicated (FIGS. 10A and B). We found that 100% of the WT mice that had tumors treated with Heat-MVA survived with very little if any residual tumor, whereas all of the WT mice treated with PBS died (median survival of 24 days) (FIGS. 10A and B). We also observed that while only 7.7% of STING-deficient mice treated with Heat-MVA survived, all of the STING-deficient mice treated with PBS died. The differences in survival between WT and $STING^{Gt/Gt}$ mice after Heat-MVA treatment were statistically significant (P<0.0001) (FIGS. 10A and B). Heat-MVA treatment in $STING^{Gt/Gt}$ mice extended median survival from 21 days to 28 days (P<0.0001) (FIGS. 10A and B). More strikingly, all of the $Batf3^{-/-}$ mice died regardless of whether they were treated with Heat-MVA or PBS. However, Heat-MVA treatment in $Batf3^{-/-}$ mice extended the median survival days from 21 to 30 days (P=0.0025) (FIGS. 10A and B). These results demonstrate that both the STING-mediated cytosolic DNA-sensing pathway and $CD8\alpha^+DCs$ are required for Heat-MVA-induced antitumor effect.

Example 11

CD8+ T Cells are Required for Heat-MVA-Induced Antitumor Effects

To determine which immune cell type is required for the therapeutic effect of Heat-MVA, we performed an antibody depletion experiment. Briefly, we implanted B16-F10 melanoma cells ($2\times10^5$) intradermally into the right flank of WT C57B/6 mice. At 8 days post tumor implantation, the tumors were injected with either Heat-MVA (an equivalent dose of $2\times10^7$ pfu) or PBS twice weekly basis as indicated (FIG. 10A). Depletion antibodies for CD4+, CD8+ and NK cells (200 μg of GK1.5, 2.43, and PK136) were injected intraperitoneally twice a week, starting one day prior to viral injection (FIG. 11A). We found that whereas intratumoral delivery of Heat-MVA leads to efficient tumor eradication, depletion of CD8+ T cells leads to the dramatic loss of therapeutic efficacy of Heat-MVA (****, $P<0.0001$) (FIG. 11B, C, D, E). Depletion of CD4+ and NK/NKT cells results in only partial loss of therapeutic efficacy of Heat-MVA (FIG. 11F, G). These results indicate that CD8+ T cells are required for the antitumor effects elicited by Heat-MVA, whereas CD4+ and NK/NKT cells also contribute to the antitumor effects. The role of CD4+ T cells in antitumor effect was further demonstrated by the lack of protection against tumor challenge in mice successfully treated with Heat-MVA in the presence of CD4-depleting antibody (FIG. 11H-I). By contrast, mice successfully treated with Heat-MVA in the presence or absence of NK/NKT-depleting antibody efficiently rejected tumor challenge (FIG. 11H-I). We conclude that although CD4+ T cells are not absolutely required for eradicating Heat-MVA-injected tumor, but they are critical for the development of anti-tumor adaptive immunity, possibly for the generation of antitumor antibodies. Taken together with Example 8, 9, 10, and 11, we surmise that intratumoral delivery of Heat-MVA leads to induction of type I IFN in immune cells and tumor cells, which leads to the activation of CD103+ dendritic cells, resulting in tumor antigen cross-presentation to CD8+ T cells within the tumors and in the circulation, as well as the generation of adaptive antitumor immunity.

Example 12

Both STING-Mediated Cytosolic DNA-Sensing Pathway and CD103+DCs are Required for the Induction of Anti-Melanoma Antibody by Heat MVA Anti-tumor antibody production is an important aspect of adaptive immunity. To test whether Heat-MVA induces anti-melanoma antibody production, we performed ELISA to determine the serum concentration of anti-B16 melanoma antibodies in mice treated with Heat-MVA or mock-treated. We found that only Heat-MVA treated mice produced anti-melanoma antibodies (FIG. 12A). This induction is abolished in STING or Batf3-deficient mice (FIG. 12A). By contrast, the production of antiviral antibodies is not dependent on either STING or Batf3 (FIG. 12B). These results suggest that the processes that facilitate tumor and viral antigen recognition in this animal model are probably different. From example 11, we know that CD8+ T cells are critical for tumor killing at the injected tumors, and therefore are important for the release of tumor antigens, which can be processed by B cells to generate antigen-specific antibodies in the presence of helper CD4+ T cells. We therefore hypothesize that in the Batf3-deficient mice, both anti-tumor CD4+ and CD8+ T cells are lacking, which contribute to the failure of production of anti-melanoma antibodies.

Example 13

The Combination of Intratumoral Injection of Heat MVA with Intraperitoneal Delivery of Anti-CTLA-4 Antibody Leads to Synergistic Antitumor Effects in a Unilateral Melanoma Implantation Model To investigate whether intratumoral injection of Heat-MVA has the ability to enhance therapeutic effects of current immunotherapies, such as the blockade of immune checkpoints (for example anti-CTLA-4 antibody), tumor-bearing mice were treated with intratumoral injection of Heat-MVA in combination with intraperitoneal delivery of anti-CTLA-4 antibody. Briefly, we implanted B16-F10 melanoma cells ($2\times10^5$) intradermally into the right flank of WT C57B/6 mice. Ten days following tumor implantation, when the tumors have grown larger than those in Example 7, 10 or 11, mice were treated with the following combinations: PBS+ isotype control, PBS+anti-CTLA-4 antibody, Heat-MVA+ isotype control, and Heat-MVA+anti-CTLA-4. As shown in FIG. 11E, tumor volume was consistent among tested groups at the start of the virus injections. Mice treated with PBS+ isotype control, or with PBS+anti-CTLA-4 died quickly due to tumor growth (FIG. 13A, B). However, following the Heat-MVA treatment, tumors that received Heat-MVA injection were significantly reduced or eradicated, with 30% of mice free of tumors at the end of the experiment (day 73 post virus injection) (FIG. 13C). Treatment with Heat-MVA and anti-CTLA-4 antibody led to superior therapeutic efficacy compared to Heat-MVA treatment alone, with 78% of mice free of tumors at the end of the experiment (FIG. 13D). We observed the synergistic effects of intratumoral injection of Heat-MVA and intraperitoneal delivery of anti-CTLA-4 antibody, which lead to the dramatic increase in cure rates and survival (FIG. 13F, *, $P<0.05$; , $P<0.01$; **, $P<0.0001$). These results indicate that intratumoral delivery of Heat-MVA leads to the alteration of tumor immune suppressive microenvironment with the generation of anti-tumor CD8+ and CD4+ T cell responses, which are enhanced or unleashed in the presence of anti-CTLA-4 antibody.

Example 14

Heat MVA is a Stronger Inducer of Antitumor Immunity than MVA

Figure 14A:
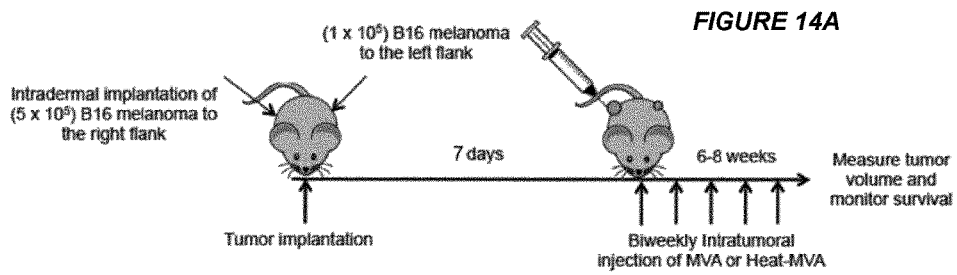
FIGS. 14A-E are a series of graphical representations of data showing that intratumoral injection of Heat-MVA is more effective than MVA in eradicating the injected tumors as well as controlling the growth of non-injected tumors.
Figure 14B:
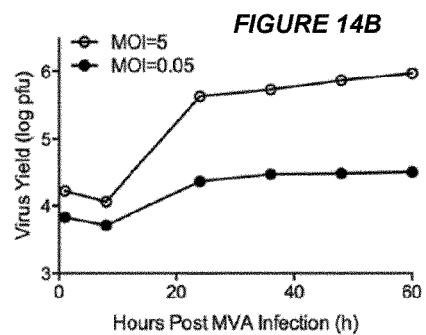
Figure 14C:
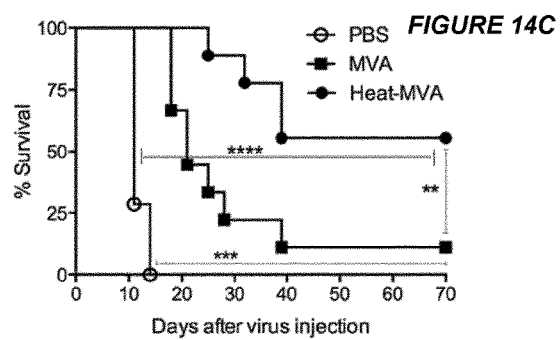
Figure 14D:
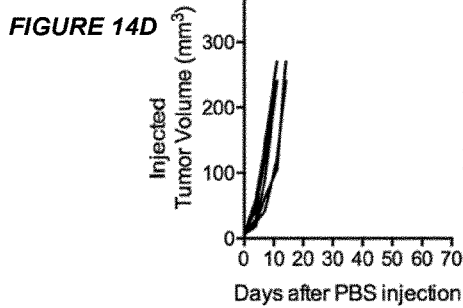
Figure 14F:
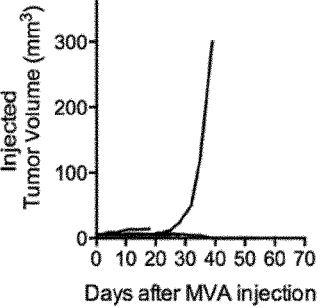
FIG. 14F-G are graphs of injected (F) and non-injected (G) tumor volume plotted against time (days) after MVA injection.
Figure 14H:
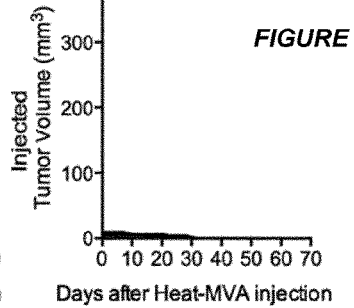
FIG. 14H-I are graphs of injected (H) and non-injected (I) tumor volume over days after Heat-MVA injection. A representative experiment is shown, repeated twice.
Figure 14E:
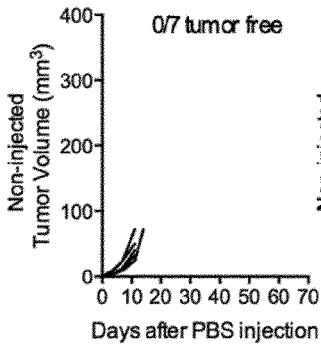
Figure 14G:
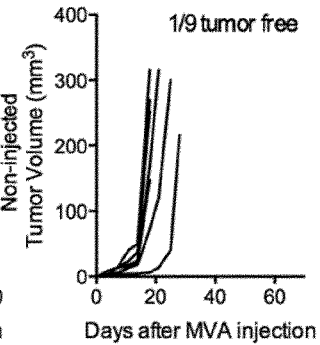
Figure 14I:
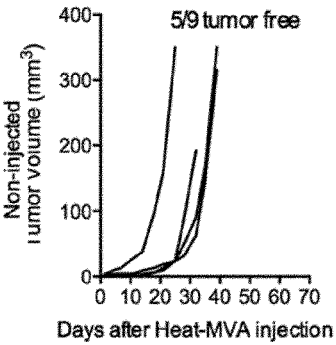

MVA is an attenuated vaccinia virus that is non-replicative in most mammalian cells. We found that MVA modestly replicates in B16 melanoma cells (FIG. 12A). Heat-MVA has reduced infectivity by 1000-fold and does not replicate in B16 melanoma cells (data not shown). We hypothesized that Heat-MVA might be a stronger activator of antitumor immunity than MVA, given that Heat-MVA induces higher levels of type I IFN than MVA in infected cDCs and tumor cells in vitro (Examples 1 and 5) as well as in vivo (Example 4). We performed the following experiment to directly compare the efficacies of tumor eradication and the generation of systemic immunity between intratumoral injection of Heat-MVA vs. MVA in a bilateral B16-F10 melanoma implantation model. Briefly, B16-F10 melanoma cells were implanted intradermally to the left and right flanks of C57B/6 mice ($5\times10^5$ to the right flank and $1\times10^5$ to the left flank). 8 days after tumor implantation, we intratumorally inject $2\times10^7$ pfu of MVA or an equivalent amount of Heat-MVA to the larger tumors on the right flank. The tumor sizes were measured and the tumors were injected twice a week. Mouse survival was monitored as well. We found that in mice treated with PBS, tumors grow rapidly at the right flank, which resulted in early death (FIGS. 12C, D and B). Intratumoral injection of either Heat-MVA or MVA resulted in delaying of tumor growth and improved survival compared with PBS (FIG. 14B, *, P<0.001 for MVA vs. PBS, , P<0.0001 for Heat-MVA vs. PBS). Intratumoral injection of Heat-MVA is more efficacious than MVA in eradicating injected tumors (9/9 tumor free for Heat-MVA vs. 6/9 tumor free for MVA) and delaying or inhibiting the growth of non-injected tumors at the contralateral side (5/9 tumor free for Heat-MVA vs. 1/9 tumor free for MVA) (FIG. 14E-H). We observed improved survival in Heat-MVA-treated mice compared with MVA-treated mice (FIG. 14B, , P<0.01). These results indicate that (i) viral replication is not necessary for achieving antitumor effects; and (ii) antitumor effects of Heat-MVA correlate with its ability to strongly induce Type I IFN.

Example 15

Heat MVA Induces More Immune Activating Cells in Non-Injected Tumors than MVA

Figures 15A, 15B:
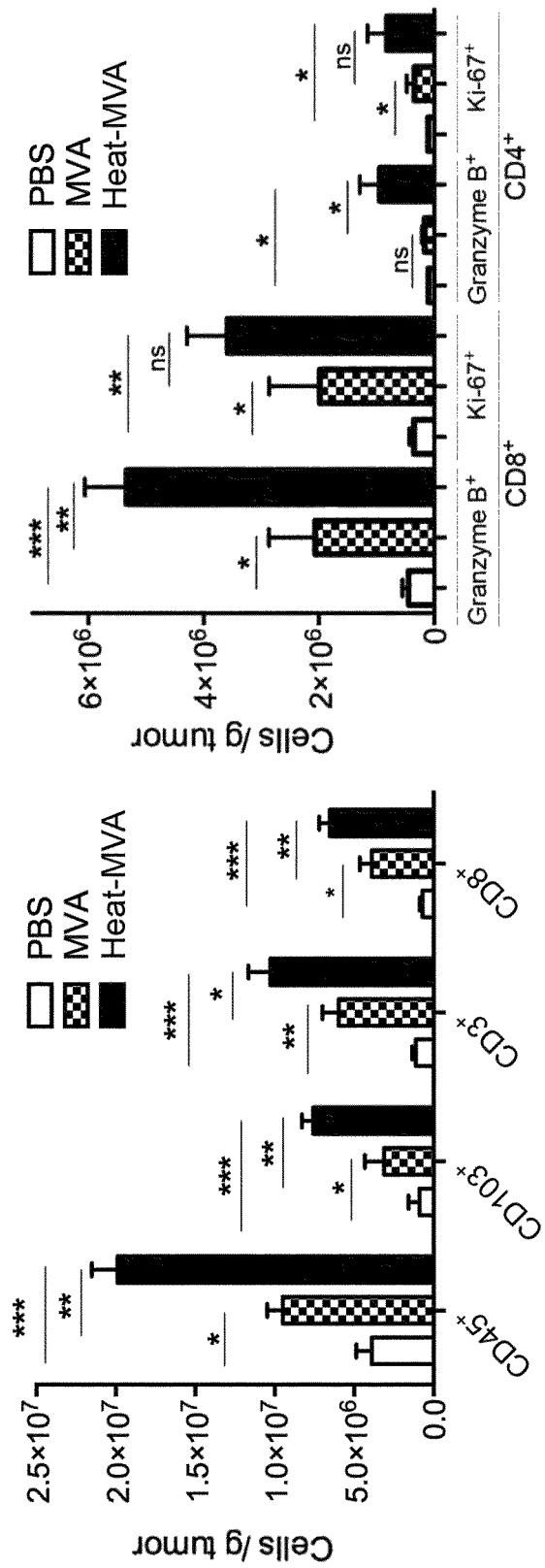
FIGS. 15A-B are a series of graphical representations of data showing that intratumoral injection of Heat-MVA is more effective than MVA or PBS in recruiting and activating immune cells in the non-injected tumors in a bilateral B16-F10 melanoma model. Tumor-bearing mice were treated with intratumoral injections of PBS, MVA or Heat-MVA as described for FIG. 14A. The non-injected tumors were harvested at day 7 post first treatment after a total of two treatments. Tumor infiltrating immune cells were analyzed by FACS.

To understand the immune mechanisms underlying the superiority of Heat-MVA over MVA in the induction of systemic antitumor immunity, we investigated the immune cell infiltrates in the non-injected tumors in Heat-MVA or MVA-treated mice. Briefly, we intradermally implanted $2.5 \times 10^5$ B16-F10 melanoma cells to the left flank and $5 \times 10^5$ B16-F10 melanoma cells to the right flank of the mice. 7 days post implantation, we injected $2 \times 10^7$ pfu of MVA, or an equivalent amount of Heat-MVA, or PBS into the larger tumors on the right flank. The injection was repeated three days later. The non-injected tumors were harvested and cell suspensions were generated. The live immune cell infiltrates in the tumors were analyzed by FACS. We observed a dramatic increase of $CD45^+$, $CD103^+$, $CD3^+$ and $CD8^+$ immune cells in the non-injected tumors of mice treated with Heat-MVA compared with those in mice treated with MVA or PBS. Although MVA-treatment also resulted in the increase of these immune cells in the non-injected tumors compared with those in PBS-treated mice, MVA is less potent than Heat-MVA in the induction of immune cells in the non-injected tumors (FIG. 15A). Heat-MVA-treatment resulted in the recruitment and proliferation of cytotoxic Granzyme B expressing $CD8^+$ and $CD4^+$ T cells in the non-injected tumors (FIG. 15B). MVA is less potent than Heat-MVA in inducing Granzyme $B^+CD8^+$ in the non-injected tumors (FIG. 15B). These results indicate that Heat-MVA is more capable than MVA in the recruitment and activation of a variety of immune cells, especially with Granzyme $B^+CD8^+$ T cells, in the non-injected tumors. This correlates with its enhanced efficacy in eradicating or delaying the growth of non-injected tumors and prolongation of survival compared with MVA.

Example 16

Intratumoral Delivery of Heat-MVA Fails to Cure B16-F 10 Melanoma in a Bilateral Tumor Implantation Model in STING or Batf3-Deficient Mice In example 10, we showed that intratumoral delivery of Heat-MVA is ineffective in eradicating B16-F10 melanoma in a unilateral implantation model. To further extend this study, we tested the efficacy of intratumoral delivery of Heat-MVA in a bilateral tumor implantation model. In PBS-treated group, all of the mice died with a median survival of 16 days due to rapid growth of the larger tumors on the right flank (FIG. 16 A, B, I). Intratumoral injection of Heat-MVA leads to eradication of all of the injected tumors, but only cleared the non-injected tumors in 3 out of 10 WT mice (FIG. 16 C, D, I, **, P<0.0001 for Heat-MVA vs. PBS). We found that although Heat-MVA-treatment leads to 30% cure of melanoma in WT mice, it failed to have therapeutic benefits in Batf3 KO mice (FIG. 16 G, H, I). In STING-deficient mice, intratumoral injection of Heat-MVA led to the delay of tumor growth and extension of median survival (FIG. 16 E, F, I,  , P<0.01). Together with example 10, we conclude that Batf3-dependent $CD103^+$ DCs are critical for the induction of antitumor immunity by intratumoral delivery of Heat-MVA. The cytosolic DNA-sensing pathway mediated by STING also plays an important role in Heat-MVA-induced adaptive antitumor immunity.

Example 17

Batf3 KO Mice are Deficient in Developing Antitumor $CD8^+$ and $CD4^+$ T Cells in Response to Intratumoral Delivery of Heat MVA Given the importance of $CD103^+$ DCs in Heat-MVA-induced antitumor immunity shown in Example 10 and 16, and the critical role of $CD8^+$ and $CD4^+$ T cells in Heat-MVA-mediated antitumor effects, we investigated whether there is a deficiency in the generation of antitumor $CD4^+$ and $CD8^+$ T cells in Batf3 KO mice in response to intratumoral injection of Heat-MVA using a bilateral tumor implantation model. Briefly, we intradermally implanted $2.5 \times 10^5$ B16-F10 melanoma cells to the left flank and $5 \times 10^5$ B16-F10 melanoma cells to the right flank of $Batf3^{-/-}$ mice and WT age-matched controls. 7 days post implantation, we injected either Heat-MVA or PBS into the larger tumors on the right flank. The injection was repeated three days later. The non-injected tumors were harvested on day 7 after first injection, and cell suspensions were generated. The live immune cell infiltrates in the injected and non-injected tumors were analyzed by FACS. Similar to Example 15, we observed a dramatic increase of $CD3^+$ and $CD8^+$ immune cells in both injected and non-injected tumors of mice treated with Heat-MVA compared with those in mice treated with PBS (FIG. 17 A-B, ,P<0.01; *,P<0.001). We also observed a significant increase of $Ki-67^+CD8^+$ and $Ki-67^+CD4^+$ T cells in both injected and non-injected tumors (FIG. 17 C-D, , P<0.01; *, P<0.001; ****, P<0.0001). By contrast, in Batf3 KO mice, the recruitment and proliferation of $CD8^+$ and $CD4^+$ T cells to the injected and non-injected tumors was diminished (FIG. 17A-D). These results indicate that $CD103^+$ DCs are crucial in cross-presenting tumor antigens and generating antitumor $CD8^+$ T cells in response to Heat-MVA treatment. Many cell type other than $CD103^+$ DCs are capable of presenting tumor antigen on MEW Class II to naïve $CD4^+$ T cells. Here we found that the number of tumor-reactive $CD4^+$ T cells in the non-injected tumors was much lower in $Batf3^{-/-}$ mice than in WT mice (FIG. 17D). It is possible that the lack of $CD8^+$ T cells in the tumors in the $Batf3^{-/-}$ mice leads to defective tumor killing and poor release of tumor antigen, which affects the generation of tumor-reactive $CD4^+$ T cells. Together with Example 10, 12 and 16, we conclude that Batf3-dependent $CD103^+/CD8\alpha$ DCs play important roles in Heat-MVA-induced antitumor effects, including the generation of tumor-reactive CD8+, CD4+ T cells, as well as anti-tumor antibodies.

Example 18

The Combination of Intratumoral Injection of Heat MVA with Intraperitoneal Delivery of Immune Checkpoint Blockade Leads to Synergistic Therapeutic Effects in a Bilateral Melanoma Implantation Model We then investigated whether intratumoral injection of Heat-MVA enhances therapeutic effects of immune checkpoint blockade therapy such as anti-CTLA-4, anti-PD-1, or anti-PD-L1 antibodies in a bilateral B16-F10 melanoma model, which simulates an individual with metastatic disease. Briefly, B16-F10 melanoma cells were implanted intradermally to the left and right flanks of C57B/6 mice ($5\times10^5$ to the right flank and $1\times10^5$ to the left flank). 8 days after tumor implantation, we intratumorally injected Heat-MVA (heat-inactivated $2\times10^7$ pfu of MVA) or PBS to the larger tumors on the right flank twice weekly. Four groups of mice were treated with Heat-MVA, with each group receiving intraperitoneal delivery of either isotype control, or anti-CTLA-4, or anti-PD-1, or anti-PD-L1 antibodies (FIG. 18A).

Whereas the PBS-treated mice died quickly with increasing tumor growth over the next 20 days (FIG. 18B, C, D), the mice treated with Heat-MVA+isotype control eradicated the injected tumors and delayed the growth of non-injected tumors at the contralateral side (FIG. 18E, F). As a result, treatment with Heat-MVA+isotype significantly extended the survival compared with PBS group (FIG. 18B, ****, P<0.0001). The combination of intratumoral injection of Heat-MVA and systemic delivery of anti-CTLA-4, anti-PD-1 and anti-PD-L1 antibodies further delayed or eliminated the non-injected tumors. As a result, 50% of mice treated with Heat-MVA+anti-CTLA-4, 50% of mice treated Heat-MVA+anti-PD-1 and 70% of mice treated with Heat-MVA+anti-PD-L1 were tumor free at the end of the experiment (day 57 post virus injection) compared with 10% of tumor-free mice treated with Heat-MVA+isotype (FIG. 18E-L).

The ability to control the growth of non-injected distant tumors correlated with the improved survival in the combination group with Heat-MVA+immune checkpoint blockade compared with Heat-MVA+isotype control (FIG. 18B, **, P<0.0001). Intraperitoneal delivery of anti-CTLA-4, anti-PD-1, or anti-PD-L1 alone has minimum therapeutic benefits in the B16-F10 melanoma model (FIG. 13B and data not shown). These results indicate that intratumoral delivery of Heat-MVA overcomes treatment resistance to immune checkpoint blockade in a metastatic B16 melanoma model which portends well for transferring this approach to human therapy with beneficial results.

This experiment will be repeated to assess the longer term benefit of conjoint immune checkpoint blockade and inactivated MVA therapy.

Example 19

UV-MVA Induces Type I Interferon in cDCs in a STING-Dependent Manner

Figure 19A:
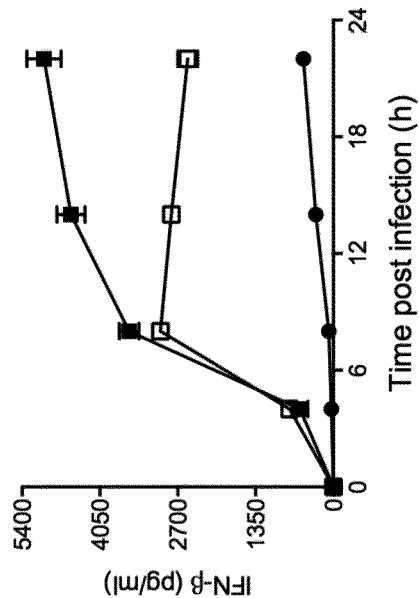
FIGS. 19A-E are a series of graphical representations of data showing that UV-inactivated MVA (UV-MVA) induces type I IFN in cDCs via a STING/IRF3-dependent cytosolic DNA-sensing pathway.
Figures 19B, 19C, 19D:
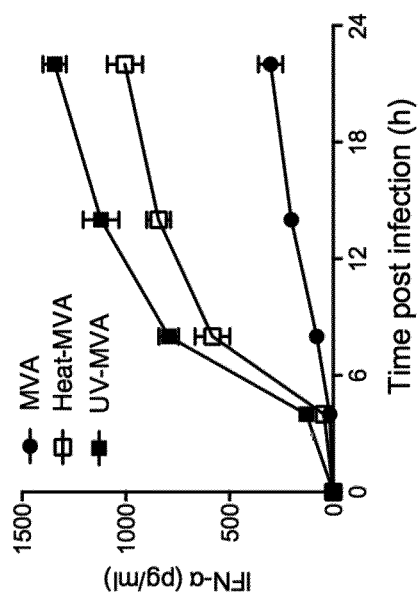
Figure 19E:
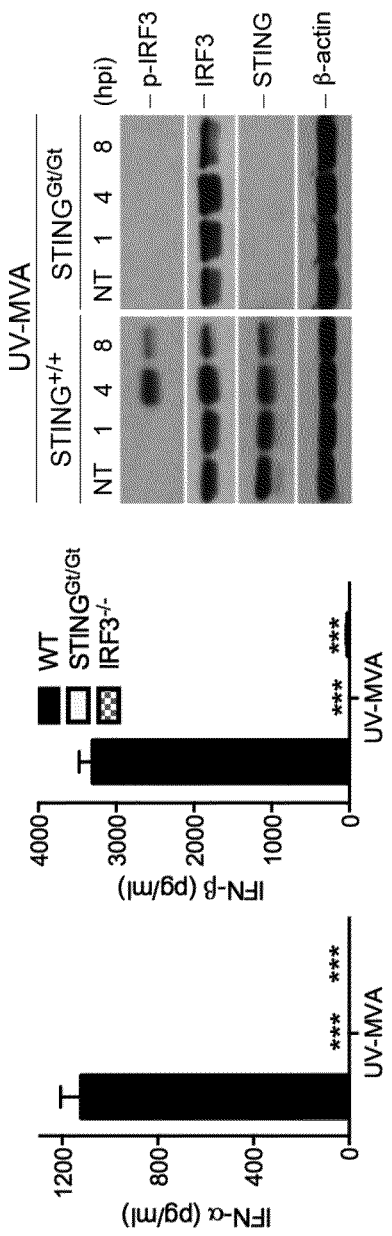

We hypothesized that ultraviolet light inactivation of MVA may also result in an immune activating virus through activation of the STING-mediated cytosolic DNA-sensing pathway. To test this hypothesis, we infected cDCs from STING$^{Gt/Gt}$ and their age-matched WT control mice. Cells ($1\times10^6$) were infected with MVA at a MOI of 10, or an equivalent amount of Heat-MVA, or UV-MVA. Supernatants were collected at 22 h post infection, and the concentrations of secreted IFN-α and IFN-β were determined by ELISA. Similar to Heat-MVA, UV-inactivated MVA also induces higher levels of type I IFN than MVA in WT cDCs (FIG. 19A, B). UV-MVA-induced type I IFN is completely abolished in STING-deficient cells (FIG. 19A, B, ***, p<0.001). These results indicate that both Heat-MVA and UV-MVA-mediated induction of IFN-α and IFN-β is dependent on the STING pathway, further corroborating that Heat-MVA and UV-MVA exert their tumor suppressive effects via similar mechanisms.

Example 20

Intratumoral Injection of UV-MVA and Heat MVA Leads to Eradication of Injected Tumors and Development of Systemic Antitumor Immunity in a Unilateral Colon Adenocarcinoma Model Experimental studies disclosed in Example 7 and 14 showed that intratumoral injection of Heat-MVA leads to tumor eradication and systemic anti-tumoral immunity in a murine transplantable B16-F10 melanoma model. To test whether Heat-MVA or UV-MVA is capable of eradicating other solid tumors, we tested the anti-tumor effects of Heat-MVA or UV-MVA in a murine MC38 colon adenocarcinoma implantation model. Colon adenocarcinoma is representative of a solid tumor not related to melanoma but was otherwise an arbitrary choice. $5\times10^5$ MC38 colon carcinoma cells were intradermally implanted into the right flank of C57B/6 mice. Tumors were allowed to grow for 7 days, after which Heat-MVA or UV-MVA (through either heat or UV-inactivation of $2\times10^7$ pfu of MVA) or PBS control were intratumorally injected twice a week. Tumors were measured twice a week and tumor volumes were calculated according the following formula: 1 (length)×w (width)×h (height)/2. We found that all of the mice treated with PBS died due to tumor growth (FIG. 20D, G). 70% of Heat-MVA-treated mice and 71% of UV-MVA-treated mice survived at the end of the experiment (around 60 days after virus injection) (FIG. 20E, F). Therefore, intratumoral injection of Heat- or UV-MVA significantly prolonged the survival of the mice compared with PBS control (FIG. 20G, ****, p<0.0001).

To test whether survived mice have developed systemic antitumor immunity, we challenged the mice with a lethal dose of MC38 cells ($1\times10^5$) at the contralateral side and monitored survival. We found that whereas all of the naïve mice developed tumors and died, 100% of the Heat- or UV-MVA-treated mice rejected tumor challenge (FIG. 20H). We also tested whether infection of MC38 cells with Heat-MVA or UV-MVA induces higher levels of inflammatory cytokines and chemokines than MVA, we infected MC38 cells with MVA at a MOI of 10, or with an equivalent amount of Heat-MVA or UV-MVA. Supernatants were collected at 22 h post infection. The concentrations of secreted IL-6, CCL4 and CCL5 in the supernatants were measured by ELISA. We also found that Heat-MVA and UV-MVA induced higher levels of IL-6, CC14 and CCL5 from MC38 cells than MVA (FIG. 20A, B, C). Collectively, results observed in Example 7, 14, and Example 20, demonstrate that Heat-MVA and UV-MVA are efficient in promoting anti-tumor effects in various solid tumors and that the findings described in this disclosure are not limited to melanoma but can be extrapolated to other solid tumors of diverse origins.

Example 21

Combination of Intratumoral Injection of Heat MVA with Intraperitoneal Delivery of Immune Checkpoint Blockade Leads to Synergistic Therapeutic Effects in a Bilateral MC38 Colon Adenocarcinoma Implantation Model We further investigated whether intratumoral injection of Heat-MVA enhances therapeutic effects of immune checkpoint blockade therapy such as anti-CTLA-4, anti- or anti-PD-L1 antibodies in other bilateral tumor implantation model, which simulates an individual with metastatic disease. Briefly, MC38 colon adenocarcinoma cells were implanted intradermally to the left and right flanks of C57B/6 mice ($5 \times 10^5$ to the right flank and $1 \times 10^5$ to the left flank). 8 days after tumor implantation, we intratumorally inject Heat-MVA (heat-inactivated $2 \times 10^7$ pfu of MVA) or PBS to the larger tumors on the right flank twice weekly. There are three groups of mice that were treated with PBS, with each group received intraperitoneal delivery of either PBS, or anti-CTLA-4, or anti-PD-L1 antibodies (FIG. 21A-F). There are three groups of mice that were treated with Heat-MVA, with each group received intraperitoneal delivery of either isotype control, or anti-CTLA-4, or anti-PD-L1 antibodies (FIG. 21G-L). PBS-treated mice died quickly with increasing tumor growth over the next 14 days (FIG. 21B, C, D), all of the mice treated with PBS+anti-CTLA-4, or PBS+anti-PD-L1, died although intraperitoneal injection of immune checkpoint blockade leads to prolonged survival compared with PBS group (FIG. 21A-F, M, *, p<0.001). Similar to what we observed in the B16-F10 bilateral implantation model (see example 14), intratumoral injection of Heat-MVA leads to eradication of injected MC38 tumors (FIG. 21G, 8/10 tumor free), however, it delayed the growth of contralateral non-injected tumors but only eradicated 1/10 of them (FIG. 21H, **, p<0.0001 Heat-MVA vs. PBS). By contrast, the combination of intratumoral delivery of Heat-MVA with intraperitoneal delivery of anti-CTLA-4 antibody or Heat-MVA+anti-PD-L 1 lead to eradication of non-injected distant tumors at a much higher efficiency than Heat-MVA alone (FIG. 21G-L), which correlated with improved survival with the combination therapy compared with Heat-MVA alone (FIG. 21N, *, p<0.05, **, p<0.01). These results have implications for treatment of metastatic solid tumors using a combination of inactivated MVA and immune checkpoint blockade.

Example 22

Combination of Intratumoral Injection of Heat-WA with Intratumoral Delivery of Immune Checkpoint Blockade Anti-CTLA-4 Antibody Leads to Synergistic Therapeutic Effects in a Bilateral B16-F10 Implantation Model In Examples 13, 18, and 21, we showed that the combination of intratumoral injection of Heat-MVA with systemic (intraperitoneal) delivery of immune checkpoint blockade led to synergistic antitumor effects in both melanoma and colon adenocarcinoma models. Here we test whether the co-administration of Heat-MVA and anti-CTLA-4 antibody (at 1/10 of dose used for intraperitoneal delivery) would achieve antitumor effects in a stringent bilateral tumor implantation model. Briefly, B16-F10 melanoma cells were implanted intradermally to the left and right flanks of C57B/6 mice ($5 \times 10^5$ to the right flank and $1 \times 10^5$ to the left flank). 8 days after tumor implantation, we intratumorally injected Heat-MVA (heat-inactivated $2 \times 10^7$ pfu of MVA) or PBS to the larger tumors on the right flank twice weekly. Three groups of mice were treated with Heat-MVA, with each group receiving: (i) intraperitoneal delivery of anti-CTLA-4 (100 µg/mouse) (ii) intratumoral delivery of isotype antibody (10 µg/mouse), or (iii) intratumoral delivery of anti-CTLA-4 antibody (10 µg/mouse) (FIG. 22). All of the PBS-treated mice died early due to the rapid growth of the injected and non-injected tumors (FIG. 22A-B). Intratumoral co-injection of Heat-MVA and isotype antibody eradicated 7 out of 10 injected tumors, but only cleared 1 out of 10 non-injected tumors (FIG. 22C-D). By contrast, intratumoral co-injection of Heat-MVA and anti-CTLA-4 antibody (10 µg/mouse) eradicated 10 out of 10 injected tumors, and cleared 7 out of 10 non-injected tumors (FIG. 22E-F), which is comparable to the therapeutic effects of the combination of intratumoral injection of Heat-MVA and intraperitoneal delivery of anti-CTLA-4 antibody (100 µg/mouse) (FIG. 22G-H). These results indicate that co-administration of Heat-MVA and an immune checkpoint blockade, anti-CTLA-4 antibody, at a much lower dose can achieve similar systemic antitumor effects to the combination of intratumoral delivery of Heat-MVA with systemic delivery of anti-CTLA-4 antibody at a higher dose. This innovative approach has several advantages: (i) this provides "in situ therapeutic vaccine" through the activation of innate immunity via the STING-dependent cytosolic DNA-sensing mechanism and the activation of adaptive immunity via the Batf3-dependent CD103$^+$/CD8α cross-presenting DCs; (ii) this allows robust activation of CDS$^+$ and CD4$^+$ cytotoxic T cells in the presence of anti-CTLA-4 antibody; (iii) this combination results in further depletion of CD4$^+$ regulatory T cells; (iv) this results in massive tumor killing via the action of CDS$^+$ and CD4$^+$ cytotoxic T cells, release of tumor antigens, and optimal generation of anti-tumor adaptive immunity, including anti-tumor antibodies; and (v) this approach also lower the systemic toxicity of anti-CTLA-4 antibody by delivering intratumorally at one tenth of the dosage used in a intraperitoneal delivery.

Given that the combination of anti-CTLA-4 and anti-PD-1 antibodies is more efficacious than either agent alone in PD-L1-negative tumors in a phase III clinical trials (Larkin et al., 2015), the inventors will deliver combined inactivated MVA and both anti-CTLA-4 and anti-PD-1/anti-PD-L1 (the blocking agents typically delivered at lower doses than monotherapy and lower doses than conjoint administration by different routes (intratumoral v. intravenous for example) will be delivered intratumorally. It is anticipated that this will result in additional augmentation of antitumor immunity and further improved survival with lower incidence of side effects. In addition, more recently developed immune checkpoint blockade antibodies will be included in such conjoint delivery such as anti-LAG-3, anti-TIM-3, and anti-TIGIT antibodies fin or the treatment of various solid tumors in pre-clinical models such as those described above.

The foregoing Examples are illustrative of the methods and features described herein and are not intended to be limiting. Moreover, they contain statements of general applicability to the present disclosure and such statements are not confined to the particular Example they appear in but The contents of all cited references are incorporated by reference in their entirety as if fully transcribed herein for all purposes.

REFERENCES

1. Jochems, C. and J. Schlom. (2011). Tumor-infiltrating immune cells and prognosis: the potential link between conventional cancer therapy and immunity. *Exp Biol Med* (Maywood) 236(5): 567-579.
2. Mlecnik, B., G. Bindea, F. Pages, and J. Galon. (2011). Tumor immunosurveillance in human cancers. *Cancer Metastasis Rev* 30(1): 5-12.
3. Angell, H. and J. Galon. (2013). From the immune contexture to the Immunoscore: the role of prognostic and predictive immune markers in cancer. *Curr Opin Immunol* 25(2): 261-267.
4. Fuertes, M. B., S. R. Woo, B. Burnett, Y. X. Fu, and T. F. Gajewski. (2013). Type I interferon response and innate immune sensing of cancer. *Trends Immunol* 34(2): 67-73.
5. Fuertes, M. B., A. K. Kacha, J. Kline, S. R. Woo, D. M. Kranz, K. M. Murphy, and T. F. Gajewski. (2011). Host type I IFN signals are required for antitumor CD8+ T cell responses through CD8{alpha}+ dendritic cells. *J Exp Med* 208(10): 2005-2016.
6. Diamond, M. S., M. Kinder, H. Matsushita, M. Mashayekhi, G. P. Dunn, J. M. Archambault, H. Lee, C. D. Arthur, J. M. White, U. Kalinke, K. M. Murphy, and R. D. Schreiber. (2011). Type I interferon is selectively required by dendritic cells for immune rejection of tumors. *J Exp Med* 208(10): 1989-2003.
7. Woo, S. R., M. B. Fuertes, L. Corrales, S. Spranger, M. J. Furdyna, M. Y. Leung, R. Duggan, Y. Wang, G. N. Barber, K. A. Fitzgerald, M. L. Alegre, and T. F. Gajewski. (2014). STING-dependent cytosolic DNA sensing mediates innate immune recognition of immunogenic tumors. *Immunity* 41(5): 830-842.
8. Deng, L., H. Liang, M. Xu, X. Yang, B. Burnette, A. Arina, X. D. Li, H. Mauceri, M. Beckett, T. Darga, X. Huang, T. F. Gajewski, Z. J. Chen, Y. X. Fu, and R. R. Weichselbaum. (2014). STING-Dependent Cytosolic DNA Sensing Promotes Radiation-Induced Type I Interferon-Dependent Antitumor Immunity in Immunogenic Tumors. *Immunity* 41(5): 843-852.
9. Oble, D. A., R. Loewe, P. Yu, and M. C. Mihm, Jr. (2009). Focus on TILs: prognostic significance of tumor infiltrating lymphocytes in human melanoma. *Cancer Immun* 9: 3.
10. Lacy, K. E., S. N. Karagiannis, and F. O. Nestle. (2012). Immunotherapy for Melanoma. *Expert Rev Dermatol* 7(1): 51-68.
11. Sharma, P. and J.P. Allison. (2015). The future of immune checkpoint therapy. *Science* 348(6230): 56-61.
12. Hodi, F. S., S. J. O'Day, D. F. McDermott, R. W. Weber, J. A. Sosman, J. B. Haanen, R. Gonzalez, C. Robert, D. Schadendorf, J. C. Hassel, W. Akerley, A. J. van den Eertwegh, J. Lutzky, P. Lorigan, J. M. Vaubel, G. P. Linette, D. Hogg, C. H. Ottensmeier, C. Lebbe, C. Peschel, I. Quirt, J. I. Clark, J. D. Wolchok, J. S. Weber, J. Tian, et al. (2010). Improved survival with ipilimumab in patients with metastatic melanoma. *N Engl J Med* 363(8): 711-723.
13. Wolchok, J. D., B. Neyns, G. Linette, S. Negrier, J. Lutzky, L. Thomas, W. Waterfield, D. Schadendorf, M. Smylie, T. Guthrie, Jr., J. J. Grob, J. Chesney, K. Chin, K. Chen, A. Hoos, S. J. O'Day, and C. Lebbe. (2010). Ipilimumab monotherapy in patients with pretreated advanced melanoma: a randomised, double-blind, multicentre, phase 2, dose-ranging study. *Lancet Oncol* 11(2): 155-164.
14. Topalian, S. L., F. S. Hodi, J. R. Brahmer, S. N. Gettinger, D. C. Smith, D. F. McDermott, J. D. Powderly, R. D. Carvajal, J. A. Sosman, M. B. Atkins, P. D. Leming, D. R. Spigel, S. J. Antonia, L. Horn, C. G. Drake, D. M. Pardoll, L. Chen, W. H. Sharfman, R. A. Anders, J. M. Taube, T. L. McMiller, H. Xu, A. J. Korman, M. Jure-Kunkel, S. Agrawal, et al. (2012). Safety, activity, and immune correlates of anti-PD-1 antibody in cancer. *N Engl J Med* 366(26): 2443-2454.
15. Wolchok, J. D., H. Kluger, M. K. Callahan, M. A. Postow, N. A. Rizvi, A. M. Lesokhin, N. H. Segal, C. E. Ariyan, R. A. Gordon, K. Reed, M. M. Burke, A. Caldwell, S. A. Kronenberg, B. U. Agunwamba, X. Zhang, I. Lowy, H. D. Inzunza, W. Feely, C. E. Horak, Q. Hong, A. J. Korman, J. M. Wigginton, A. Gupta, and M. Sznol. (2013). Nivolumab plus ipilimumab in advanced melanoma. *N Engl J Med* 369(2): 122-133.
16. Hamid, O., C. Robert, A. Daud, F. S. Hodi, W. J. Hwu, R. Kefford, J. D. Wolchok, P. Hersey, R. W. Joseph, J. S. Weber, R. Dronca, T. C. Gangadhar, A. Patnaik, H. Zarour, A. M. Joshua, K. Gergich, J. Elassaiss-Schaap, A. Algazi, C. Mateus, P. Boasberg, P. C. Tumeh, B. Chmielowski, S. W. Ebbinghaus, X. N. Li, S. P. Kang, et al. (2013). Safety and Tumor Responses with Lambrolizumab (Anti-PD-1) in Melanoma. *N Engl J Med*.
17. Tumeh, P. C., C. L. Harview, J. H. Yearley, I. P. Shintaku, E. J. Taylor, L. Robert, B. Chmielowski, M. Spasic, G. Henry, V. Ciobanu, A. N. West, M. Carmona, C. Kivork, E. Seja, G. Cherry, A. J. Gutierrez, T. R. Grogan, C. Mateus, G. Tomasic, J. A. Glaspy, R. O. Emerson, H. Robins, R. H. Pierce, D. A. Elashoff, C. Robert, et al. (2014). PD-1 blockade induces responses by inhibiting adaptive immune resistance. *Nature* 515(7528): 568-571.
18. Zamarin, D., R. B. Holmgaard, S. K. Subudhi, J. S. Park, M. Mansour, P. Palese, T. Merghoub, J. D. Wolchok, and J. P. Allison. (2014). Localized oncolytic virotherapy overcomes systemic tumor resistance to immune checkpoint blockade immunotherapy. *Sci Transl Med* 6(226): 226ra232.
19. Kirn, D. H. and S. H. Thorne. (2009). Targeted and armed oncolytic poxviruses: a novel multi-mechanistic therapeutic class for cancer. *Nat Rev Cancer* 9(1): 64-71.
20. Moss, B., *Poxviridae: The viruses and their replication*. In Fields Virology, ed. e. D. M. Knipe 2007: Lippincott Williams & Wilkins. pp. 2905-2946.
21. Breitbach, C. J., S. H. Thorne, J. C. Bell, and D. H. Kirn. (2012). Targeted and armed oncolytic poxviruses for cancer: the lead example of JX-594. *Curr Pharm Biotechnol* 13(9): 1768-1772.
22. Park, B. H., T. Hwang, T. C. Liu, D. Y. Sze, J. S. Kim, H. C. Kwon, S. Y. Oh, S. Y. Han, J. H. Yoon, S. H. Hong, A. Moon, K. Speth, C. Park, Y. J. Ahn, M. Daneshmand, B. G. Rhee, H. M. Pinedo, J. C. Bell, and D. H. Kirn. (2008). Use of a targeted oncolytic poxvirus, JX-594, in patients with refractory primary or metastatic liver cancer: a phase I trial. *Lancet Oncol* 9(6): 533-542.
23. Kirn, D. H., Y. Wang, F. Le Boeuf, J. Bell, and S. H. Thorne. (2007). Targeting of interferon-beta to produce a specific, multi-mechanistic oncolytic vaccinia virus. *PLoS Med* 4(12): e353.

24. Thorne, S. H., T. H. Hwang, W. E. O'Gorman, D. L. Bartlett, S. Sei, F. Kanji, C. Brown, J. Werier, J. H. Cho, D. E. Lee, Y. Wang, J. Bell, and D. H. Kirn. (2007). Rational strain selection and engineering creates a broad-spectrum, systemically effective oncolytic poxvirus, JX-963. *J Clin Invest* 117(11): 3350-3358.

25. Engelmayer, J., M. Larsson, M. Subklewe, A. Chahroudi, W. I. Cox, R. M. Steinman, and N. Bhardwaj. (1999). Vaccinia virus inhibits the maturation of human dendritic cells: a novel mechanism of immune evasion. *J Immunol* 163(12): 6762-6768.

26. Jenne, L., C. Hauser, J. F. Arrighi, J. H. Saurat, and A. W. Hugin. (2000). Poxvirus as a vector to transduce human dendritic cells for immunotherapy: abortive infection but reduced APC function. *Gene Ther* 7(18): 1575-1583.

27. Deng, L., P. Dai, W. Ding, R. D. Granstein, and S. Shuman. (2006). Vaccinia virus infection attenuates innate immune responses and antigen presentation by epidermal dendritic cells. *J Virol* 80(20): 9977-9987.

28. Li, P., N. Wang, D. Zhou, C. S. Yee, C. H. Chang, R. R. Brutkiewicz, and J. S. Blum. (2005). Disruption of MHC class II-restricted antigen presentation by vaccinia virus. *J Immunol* 175(10): 6481-6488.

29. Seet, B. T., J. B. Johnston, C. R. Brunetti, J. W. Barrett, H. Everett, C. Cameron, J. Sypula, S. H. Nazarian, A. Lucas, and G. McFadden. (2003). Poxviruses and immune evasion. *Annu Rev Immunol* 21: 377-423.

30. Meyer, H., G. Sutter, and A. Mayr. (1991). Mapping of deletions in the genome of the highly attenuated vaccinia virus MVA and their influence on virulence. *J Gen Virol* 72 (Pt 5): 1031-1038.

31. McCurdy, L. H., B. D. Larkin, J. E. Martin, and B. S. Graham. (2004). Modified vaccinia Ankara: potential as an alternative smallpox vaccine. *Clin Infect Dis* 38(12): 1749-1753.

32. Vollmar, J., N. Arndtz, K. M. Eckl, T. Thomsen, B. Petzold, L. Mateo, B. Schlereth, A. Handley, L. King, V. Hulsemann, M. Tzatzaris, K. Merkl, N. Wulff, and P. Chaplin. (2006). Safety and immunogenicity of IMVAMUNE, a promising candidate as a third generation smallpox vaccine. *Vaccine* 24(12): 2065-2070.

33. Sutter, G. and C. Staib. (2003). Vaccinia vectors as candidate vaccines: the development of modified vaccinia virus Ankara for antigen delivery. *Curr Drug Targets Infect Disord* 3(3): 263-271.

34. Gomez, C. E., J. L. Najera, M. Krupa, and M. Esteban. (2008). The poxvirus vectors MVA and NYVAC as gene delivery systems for vaccination against infectious diseases and cancer. *Curr Gene Ther* 8(2): 97-120.

35. Gomez, C. E., J. L. Najera, M. Krupa, B. Perdiguero, and M. Esteban. (2011). MVA and NYVAC as vaccines against emergent infectious diseases and cancer. *Curr Gene Ther* 11(3): 189-217.

36. Goepfert, P. A., M. L. Elizaga, A. Sato, L. Qin, M. Cardinali, C. M. Hay, J. Hural, S. C. DeRosa, O. D. DeFawe, G. D. Tomaras, D. C. Montefiori, Y. Xu, L. Lai, S. A. Kalams, L. R. Baden, S. E. Frey, W. A. Blattner, L. S. Wyatt, B. Moss, and H. L. Robinson. (2011). Phase 1 safety and immunogenicity testing of DNA and recombinant modified vaccinia Ankara vaccines expressing HIV-1 virus-like particles. *J Infect Dis* 203(5): 610-619.

37. Wyatt, L. S., I. M. Belyakov, P. L. Earl, J. A. Berzofsky, and B. Moss. (2008). Enhanced cell surface expression, immunogenicity and genetic stability resulting from a spontaneous truncation of HIV Env expressed by a recombinant MVA. *Virology* 372(2): 260-272.

38. Garcia, F., J. C. Bernaldo de Quiros, C. E. Gomez, B. Perdiguero, J. L. Najera, V. Jimenez, J. Garcia-Arriaza, A. C. Guardo, I. Perez, V. Diaz-Brito, M. S. Conde, N. Gonzalez, A. Alvarez, J. Alcami, J. L. Jimenez, J. Pich, J. A. Arnaiz, M. J. Maleno, A. Leon, M. A. Munoz-Fernandez, P. Liljestrom, J. Weber, G. Pantaleo, J. M. Gatell, M. Plana, et al. (2011). Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02). *Vaccine* 29(46): 8309-8316.

39. Bowie, A., E. Kiss-Toth, J. A. Symons, G. L. Smith, S. K. Dower, and L. A. O'Neill. (2000). A46R and A52R from vaccinia virus are antagonists of host IL-1 and toll-like receptor signaling. *Proc Natl Acad Sci USA* 97(18): 10162-10167.

40. Harte, M. T., I. R. Haga, G. Maloney, P. Gray, P. C. Reading, N. W. Bartlett, G. L. Smith, A. Bowie, and L. A. O'Neill. (2003). The poxvirus protein A52R targets Toll-like receptor signaling complexes to suppress host defense. *J Exp Med* 197(3): 343-351.

41. DiPerna, G., J. Stack, A. G. Bowie, A. Boyd, G. Kotwal, Z. Zhang, S. Arvikar, E. Latz, K. A. Fitzgerald, and W. L. Marshall. (2004). Poxvirus protein N1L targets the 1-kappaB kinase complex, inhibits signaling to NF-kappaB by the tumor necrosis factor superfamily of receptors, and inhibits NF-kappaB and IRF3 signaling by toll-like receptors. *J Biol Chem* 279(35): 36570-36578.

42. Graham, S. C., M. W. Bahar, S. Cooray, R. A. Chen, D. M. Whalen, N. G. Abrescia, D. Alderton, R. J. Owens, D. I. Stuart, G. L. Smith, and J. M. Grimes. (2008). Vaccinia virus proteins A52 and B14 Share a Bcl-2-like fold but have evolved to inhibit NF-kappaB rather than apoptosis. *PLoS Pathog* 4(8): e1000128.

43. Lynch, H. E., C. A. Ray, K. L. Oie, J. J. Pollara, I. T. Petty, A. J. Sadler, B. R. Williams, and D. J. Pickup. (2009). Modified vaccinia virus Ankara can activate NF-kappaB transcription factors through a double-stranded RNA-activated protein kinase (PKR)-dependent pathway during the early phase of virus replication. *Virology* 391(2): 177-186.

44. Willis, K. L., S. Patel, Y. Xiang, and J. L. Shisler. (2009). The effect of the vaccinia K1 protein on the PKR-eIF2alpha pathway in RK13 and HeLa cells. *Virology* 394(1): 73-81.

45. Kotwal, G. J., A. W. Hugin, and B. Moss. (1989). Mapping and insertional mutagenesis of a vaccinia virus gene encoding a 13,800-Da secreted protein. *Virology* 171(2): 579-587.

46. Bartlett, N., J. A. Symons, D. C. Tscharke, and G. L. Smith. (2002). The vaccinia virus N1L protein is an intracellular homodimer that promotes virulence. *J Gen Virol* 83(Pt 8): 1965-1976.

47. Brandt, T., M. C. Heck, S. Vijaysri, G. M. Jentarra, J. M. Cameron, and B. L. Jacobs. (2005). The N-terminal domain of the vaccinia virus E3L-protein is required for neurovirulence, but not induction of a protective immune response. *Virology* 333(2): 263-270.

48. Chang, H. W., J. C. Watson, and B. L. Jacobs. (1992). The E3L gene of vaccinia virus encodes an inhibitor of the interferon-induced, double-stranded RNA-dependent protein kinase. *Proc Natl Acad Sci USA* 89(11): 4825-4829.

49. Xiang, Y., R. C. Condit, S. Vijaysri, B. Jacobs, B. R. Williams, and R. H. Silverman. (2002). Blockade of 50. Beattie, E., E. B. Kauffman, H. Martinez, M. E. Perkus, B. L. Jacobs, E. Paoletti, and J. Tartaglia. (1996). Host-range restriction of vaccinia virus E3L-specific deletion mutants. *Virus Genes* 12(1): 89-94.
51. Brandt, T. A. and B. L. Jacobs. (2001). Both carboxy- and amino-terminal domains of the vaccinia virus interferon resistance gene, E3L, are required for pathogenesis in a mouse model. *J Virol* 75(2): 850-856.
52. Langland, J. O., J. C. Kash, V. Carter, M. J. Thomas, M. G. Katze, and B. L. Jacobs. (2006). Suppression of proinflammatory signal transduction and gene expression by the dual nucleic acid binding domains of the vaccinia virus E3L proteins. *J Virol* 80(20): 10083-10095.
53. Smith, E. J., I. Marie, A. Prakash, A. Garcia-Sastre, and D. E. Levy. (2001). IRF3 and IRF7 phosphorylation in virus-infected cells does not require double-stranded RNA-dependent protein kinase R or Ikappa B kinase but is blocked by Vaccinia virus E3L protein. *J Biol Chem* 276(12): 8951-8957.
54. Guerra, S., A. Caceres, K. P. Knobeloch, I. Horak, and M. Esteban. (2008). Vaccinia virus E3 protein prevents the antiviral action of ISG15. *PLoS Pathog* 4(7): e1000096.
55. Deng, L., P. Dai, T. Parikh, H. Cao, V. Bhoj, Q. Sun, Z. Chen, T. Merghoub, A. Houghton, and S. Shuman. (2008). Vaccinia virus subverts a mitochondrial antiviral signaling protein-dependent innate immune response in keratinocytes through its double-stranded RNA binding protein, E3. *J Virol* 82(21): 10735-10746.
56. Drillien, R., D. Spehner, and D. Hanau. (2004). Modified vaccinia virus Ankara induces moderate activation of human dendritic cells. *J Gen Virol* 85(Pt 8): 2167-2175.
57. Waibler, Z., M. Anzaghe, H. Ludwig, S. Akira, S. Weiss, G. Sutter, and U. Kalinke. (2007). Modified vaccinia virus Ankara induces Toll-like receptor-independent type I interferon responses. *J Virol* 81(22): 12102-12110.
58. Delaloye, J., T. Roger, Q. G. Steiner-Tardivel, D. Le Roy, M. Knaup Reymond, S. Akira, V. Petrilli, C. E. Gomez, B. Perdiguero, J. Tschopp, G. Pantaleo, M. Esteban, and T. Calandra. (2009). Innate immune sensing of modified vaccinia virus Ankara (MVA) is mediated by TLR2-TLR6, MDA-5 and the NALP3 inflammasome. *PLoS Pathog* 5(6): e1000480.
59. Ishikawa, H. and G. N. Barber. (2008). STING is an endoplasmic reticulum adaptor that facilitates innate immune signalling. *Nature* 455(7213): 674-678.
60. Zhong, B., Y. Yang, S. Li, Y. Y. Wang, Y. Li, F. Diao, C. Lei, X. He, L. Zhang, P. Tien, and H. B. Shu. (2008). The adaptor protein MITA links virus-sensing receptors to IRF3 transcription factor activation. *Immunity* 29(4): 538-550.
61. Ishikawa, H., Z. Ma, and G. N. Barber. (2009). STING regulates intracellular DNA-mediated, type I interferon-dependent innate immunity. *Nature* 461(7265): 788-792.
62. Wu, J., L. Sun, X. Chen, F. Du, H. Shi, C. Chen, and Z. J. Chen. (2013). Cyclic GMP-AMP is an endogenous second messenger in innate immune signaling by cytosolic DNA. *Science* 339(6121): 826-830.
63. Sun, L., J. Wu, F. Du, X. Chen, and Z. J. Chen. (2013). Cyclic GMP-AMP synthase is a cytosolic DNA sensor that activates the type I interferon pathway. *Science* 339(6121): 786-791.
64. Gao, P., M. Ascano, Y. Wu, W. Barchet, B. L. Gaffney, T. Zillinger, A. A. Serganov, Y. Liu, R. A. Jones, G. Hartmann, T. Tuschl, and D. J. Patel. (2013). Cyclic [G(2',5')pA(3',5')p] is the metazoan second messenger produced by DNA-activated cyclic GMP-AMP synthase. *Cell* 153(5): 1094-1107.
65. Civril, F., T. Deimling, C. C. de Oliveira Mann, A. Ablasser, M. Moldt, G. Witte, V. Hornung, and K. P. Hopfner. (2013). Structural mechanism of cytosolic DNA sensing by cGAS. *Nature* 498(7454): 332-337.
66. Ablasser, A., M. Goldeck, T. Caviar, T. Deimling, G. Witte, I. Rohl, K. P. Hopfner, J. Ludwig, and V. Hornung. (2013). cGAS produces a 2'-5'-linked cyclic dinucleotide second messenger that activates STING. *Nature* 498 (7454): 380-384.
67. Li, X., C. Shu, G. Yi, C. T. Chaton, C. L. Shelton, J. Diao, X. Zuo, C. C. Kao, A. B. Herr, and P. Li. (2013). Cyclic GMP-AMP synthase is activated by double-stranded DNA-induced oligomerization. *Immunity* 39(6): 1019-1031.
68. Zhang, X., H. Shi, J. Wu, X. Zhang, L. Sun, C. Chen, and Z. J. Chen. (2013). Cyclic GMP-AMP containing mixed phosphodiester linkages is an endogenous high-affinity ligand for STING. *Mol Cell* 51(2): 226-235.
69. Gao, P., M. Ascano, T. Zillinger, W. Wang, P. Dai, A. A. Serganov, B. L. Gaffney, S. Shuman, R. A. Jones, L. Deng, G. Hartmann, W. Barchet, T. Tuschl, and D. J. Patel. (2013). Structure-function analysis of STING activation by c[G(2',5')pA(3',5')p] and targeting by antiviral DMXAA. *Cell* 154(4): 748-762.
70. Dai, P., W. Wang, H. Cao, F. Avogadri, L. Dai, I. Drexler, J. A. Joyce, X. D. Li, Z. Chen, T. Merghoub, S. Shuman, and L. Deng. (2014). Modified vaccinia virus Ankara triggers type I IFN production in murine conventional dendritic cells via a cGAS/STING-mediated cytosolic DNA-sensing pathway. *PLoS Pathog* 10(4): e1003989.
71. Huber, J. P. and J. D. Farrar. (2011). Regulation of effector and memory T-cell functions by type I interferon. *Immunology* 132(4): 466-474.
72. Pardoll, D. M. (2012). The blockade of immune checkpoints in cancer immunotherapy. *Nat Rev Cancer* 12(4): 252-264.
73. Nemunaitis, J. (1999). Oncolytic viruses. *Invest New Drugs* 17(4): 375-386.
74. Kirn, D., R. L. Martuza, and J. Zwiebel. (2001). Replication-selective virotherapy for cancer: Biological principles, risk management and future directions. *Nat Med* 7(7): 781-787.
75. Coffey, M. C., J. E. Strong, P. A. Forsyth, and P. W. Lee. (1998). Reovirus therapy of tumors with activated Ras pathway. *Science* 282(5392): 1332-1334.
76. Mayr, A., H. Stickl, H. K. Muller, K. Danner, and H. Singer. (1978). [The smallpox vaccination strain MVA: marker, genetic structure, experience gained with the parenteral vaccination and behavior in organisms with a debilitated defence mechanism (author's transl)]. *Zentralbl Bakteriol B* 167(5-6): 375-390.
77. Verheust, C., M. Goossens, K. Pauwels, and D. Breyer. (2012). Biosafety aspects of modified vaccinia virus Ankara (MVA)-based vectors used for gene therapy or vaccination. *Vaccine* 30(16): 2623-2632.
78. Antoine, G., F. Scheiflinger, F. Dorner, and F. G. Falkner. (1998). The complete genomic sequence of the modified vaccinia Ankara strain: comparison with other orthopoxviruses. *Virology* 244(2): 365-396.
79. Tsung, K., J. H. Yim, W. Marti, R. M. Buller, and J. A. Norton. (1996). Gene expression and cytopathic effect of vaccinia virus inactivated by psoralen and long-wave UV light. *J Virol* 70(1): 165-171.

80. Mayr, A., Hochstein-Mintzel V, Stickl H. (1975). Passage history, properties, and applicability of the attenuated vaccinia virus strain MVA [in German]. *Infection* 3: 6-14.
81. Brandler, S., A. Lepelley, M. Desdouits, F. Guivel-Benhassine, P. E. Ceccaldi, Y. Levy, O. Schwartz, and A. Moris. (2010). Preclinical studies of a modified vaccinia virus Ankara-based HIV candidate vaccine: antigen presentation and antiviral effect. *J Virol* 84(10): 5314-5328.
82. Takaoka, A. and T. Taniguchi. (2003). New aspects of IFN-alpha/beta signalling in immunity, oncogenesis and bone metabolism. *Cancer Sci* 94(5): 405-411.
83. Nagorsen, D., E. Wang, F. M. Marincola, and J. Even. (2002). Transcriptional analysis of tumor-specific T-cell responses in cancer patients. *Crit Rev Immunol* 22(5-6): 449-462.
84. Pramanick, S., Singodia, D., and Chandel, V. (2013). Excipient selection in parenteral formulation development. *Pharma Times* 45(3): 65-77.
85. Weaver, J. R., M. Shamim, E. Alexander, D. H. Davies, P. L. Feigner, and S. N. Isaacs. (2007). The identification and characterization of a monoclonal antibody to the vaccinia virus E3 protein. *Virus Res* 130(1-2): 269-274.
86. Li, X. D., J. Wu, D. Gao, H. Wang, L. Sun, and Z. J. Chen. (2013). Pivotal roles of cGAS-cGAMP signaling in antiviral defense and immune adjuvant effects. *Science* 341(6152): 1390-1394.
87. Tanaka, Y. and Z. J. Chen. (2012). STING specifies IRF3 phosphorylation by TBK1 in the cytosolic DNA signaling pathway. *Sci Signal* 5(214): ra20.
88. Xiao, T. S. and K. A. Fitzgerald. (2013). The cGAS-STING pathway for DNA sensing. *Mol Cell* 51(2): 135-139.
89. Sauer, J. D., K. Sotelo-Troha, J. von Moltke, K. M. Monroe, C. S. Rae, S. W. Brubaker, M. Hyodo, Y. Hayakawa, J. J. Woodward, D. A. Portnoy, and R. E. Vance. (2011). The N-ethyl-N-nitrosourea-induced Goldenticket mouse mutant reveals an essential function of Sting in the in vivo interferon response to Listeria monocytogenes and cyclic dinucleotides. *Infect Immun* 79(2): 688-694.
90. Corrales, L., L. H. Glickman, S. M. McWhirter, D. B. Kanne, K. E. Sivick, G. E. Katibah, S. R. Woo, E. Lemmens, T. Banda, J. J. Leong, K. Metchette, T. W. Dubensky, Jr., and T. F. Gajewski. (2015). Direct Activation of STING in the Tumor Microenvironment Leads to Potent and Systemic Tumor Regression and Immunity. *Cell Rep* 11(7): 1018-1030.
91. Hildner, K., B. T. Edelson, W. E. Purtha, M. Diamond, H. Matsushita, M. Kohyama, B. Calderon, B. U. Schraml, E. R. Unanue, M. S. Diamond, R. D. Schreiber, T. L. Murphy, and K. M. Murphy. (2008). Batf3 deficiency reveals a critical role for CD8alpha+ dendritic cells in cytotoxic T cell immunity. *Science* 322(5904): 1097-1100.
92. Edelson, B. T., W. Kc, R. Juang, M. Kohyama, L. A. Benoit, P. A. Klekotka, C. Moon, J. C. Albring, W. Ise, D. G. Michael, D. Bhattacharya, T. S. Stappenbeck, M. J. Holtzman, S. S. Sung, T. L. Murphy, K. Hildner, and K. M. Murphy. (2010). Peripheral CD103+ dendritic cells form a unified subset developmentally related to CD8alpha+ conventional dendritic cells. *J Exp Med* 207 (4): 823-836.

The invention claimed is:

1. A method for treating a solid malignant tumor in a subject in need thereof, the method comprising delivering to tumor cells of the subject a therapeutically effective amount of inactivated modified vaccinia Ankara (inactivated MVA) virus, thereby resulting in treatment of the tumor, wherein the tumor is a carcinoma.

2. The method of claim 1, wherein the treatment comprises one or more of the following:
   inducing the immune system of the subject to mount an immune response against the tumor;
   reducing the size of the tumor;
   eradicating the tumor;
   inhibiting growth of the tumor;
   inhibiting metastasis of the tumor;
   reducing or eradicating metastatic tumor;
   inducing apoptosis of the tumor cells; and
   prolonging survival of the subject as compared to an untreated control subject.

3. The method of claim 1, wherein the tumor includes tumor located at the site of inactivated MVA delivery, or tumor located both at the site and elsewhere in the body of the subject.

4. The method of claim 1, wherein the inactivated MVA does not comprise a heterologous nucleic acid encoding or expressing a tumor antigen.

5. The method of claim 1, further comprising conjointly administering to the subject a therapeutically effective amount of an immune checkpoint blocking agent.

6. The method of claim 5, wherein the inactivated MVA is delivered parenterally, intratumorally, intravenously, and/or intraperitoneally to the subject, and wherein the immune checkpoint blocking agent is administered parenterally, intratumorally, intravenously, and/or intraperitoneally to the subject.

7. The method of claim 5, wherein the immune checkpoint blocking agent modulates the activity of one or more checkpoint proteins selected from the group consisting of: CTLA-4, CD80, CD86, PD-1, PD-L1, PD-L2, TIGIT, LAG3, B7-H3, B7-H4, TIM3, ICOS, BTLA, and CD28.

8. The method of claim 5, wherein the inactivated MVA is delivered to the subject separately, sequentially, or simultaneously with the immune checkpoint blocking agent.

9. The method of claim 5, wherein one or both of the inactivated MVA and the immune checkpoint blocking agent are respectively delivered and administered during a period of time of several weeks, months, or years, or indefinitely as long as benefits persist or a maximum tolerated dose is reached.

10. The method of claim 5, wherein the inactivated MVA is delivered at a dosage per administration of about 105 to about 1010 plaque-forming units (pfu).

11. The method of claim 5, wherein the combination of the inactivated MVA and the immune checkpoint blocking agent has a synergistic effect in the treatment of the tumor, wherein the immune checkpoint blocking agent is selected from an anti-CTLA-4 antibody, an anti-PD-1 antibody, or an anti-PD-L1 antibody.

12. The method of claim 1, wherein the inactivated MVA is heat-inactivated MVA or UV-inactivated MVA.

13. A method of eliciting an immune response in a subject in need thereof, the method comprising delivering to the subject a therapeutically effective amount of an inactivated modified vaccinia Ankara (inactivated MVA) virus, thereby inducing at least one or more of the following:

increasing at least one of cytotoxic CD8+ T cells and effector CD4+ T cells;

inducing maturation of dendritic cells through induction of type I IFN;

reducing immune suppressive (regulatory) CD4+ T cells; and inducing type I IFN, inflammatory cytokine and chemokine production in immune cells and stromal fibroblasts as compared to untreated control cells.

14. The method of claim 13, wherein the inactivated MVA delivered to the subject is effective to recruit and activate CD4+ effector T cells accompanied by a reduction of regulatory CD4+ T cells.

15. The method of claim 13, wherein the inactivated MVA is delivered parenterally, intratumorally, intravenously, or intraperitoneally.

16. The method of claim 13, wherein the inactivated MVA is delivered at a dosage per administration of about $10^5$ to about $10^{10}$ plaque-forming units (pfu).

17. The method of claim 13, wherein the delivery is repeated with a frequency within the range from once per month to once per week or more, and continues for several weeks, months, years, or indefinitely until a maximum tolerated dose is reached.

18. The method of claim 13, wherein the inactivated MVA induces type I interferon (type I IFN) in infected cells and/or activates type I IFN gene expression by inducing higher levels of IFNA4 and IFNB mRNA and/or increasing phospho-IRF3 compared to MVA.

19. The method of claim 13, wherein delivery of inactivated MVA induces higher levels of production of at least one of IFN-β, IL-6, CCL4, and CCL5, and/or higher levels of gene expression of IFN-β, IL6, CCL4, and CCL5 than MVA.

20. The method of claim 13, wherein the inactivated MVA is heat-inactivated MVA or UV-inactivated MVA.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctgtgtgat gcaggaacc                                                19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcacctccca ggcacaga                                                 18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
tggagatgac ggagaagatg                                                    20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttggatggca aaggcagt                                                      18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atcaagaagg tggtgaagca                                                    20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agacaacctg gtcctcagtg t                                                  21
```